(12) United States Patent
Tokito et al.

(10) Patent No.: US 9,290,516 B2
(45) Date of Patent: Mar. 22, 2016

(54) BENZOBIS(THIADIAZOLE) DERIVATIVE AND ORGANIC ELECTRONICS DEVICE COMPRISING SAME

(71) Applicant: Ube Industries, Ltd., Ube-shi (JP)

(72) Inventors: Shizuo Tokito, Yonezawa (JP); Daisuke Kumaki, Yonezawa (JP); Hidetaka Shima, Ube (JP); Hiroyuki Oda, Ube (JP); Yasuhiro Tanaka, Ichihara (JP); Kazuaki Kakita, Ichihara (JP); Toshikazu Machida, Ichihara (JP); Yasuhiro Yoneda, Ube (JP); Youji Omata, Ube (JP); Tetsuro Shimano, Ube (JP)

(73) Assignee: UBE INDUSTRIES, LTD., Ube-Shi (JP)

( * ) Notice: Subject to any disclaimer, the term of this patent is extended or adjusted under 35 U.S.C. 154(b) by 0 days.

(21) Appl. No.: 14/386,984

(22) PCT Filed: Mar. 15, 2013

(86) PCT No.: PCT/JP2013/057567
§ 371 (c)(1),
(2) Date: Sep. 22, 2014

(87) PCT Pub. No.: WO2013/141182
PCT Pub. Date: Sep. 26, 2013

(65) Prior Publication Data
US 2015/0059853 A1 Mar. 5, 2015

(30) Foreign Application Priority Data
Mar. 23, 2012 (JP) .................. 2012-067773

(51) Int. Cl.
C07D 513/04 (2006.01)
H01L 51/00 (2006.01)
H01L 51/05 (2006.01)
C09D 11/52 (2014.01)
H01L 27/32 (2006.01)
H01L 51/42 (2006.01)
C08G 61/12 (2006.01)
H01L 51/50 (2006.01)

(52) U.S. Cl.
CPC ............ *C07D 513/04* (2013.01); *C08G 61/123* (2013.01); *C08G 61/126* (2013.01); *C09D 11/52* (2013.01); *H01L 27/3274* (2013.01); *H01L 51/0071* (2013.01); *H01L 51/0097* (2013.01); *H01L 51/0545* (2013.01); *H01L 51/42* (2013.01); *H01L 51/5012* (2013.01); C08G 2261/1642 (2013.01); C08G 2261/1644 (2013.01); C08G 2261/3223 (2013.01); C08G 2261/3246 (2013.01); C08G 2261/364 (2013.01); C08G 2261/414 (2013.01); C08G 2261/51 (2013.01); C08G 2261/91 (2013.01); C08G 2261/92 (2013.01); C08G 2261/95 (2013.01); H01L 51/5056 (2013.01); H01L 51/5072 (2013.01); H01L 2251/5338 (2013.01); Y02E 10/549 (2013.01)

(58) Field of Classification Search
CPC .................................................... C07D 513/04
See application file for complete search history.

(56) References Cited

U.S. PATENT DOCUMENTS
2009/0292130 A1   11/2009   Shi et al.

FOREIGN PATENT DOCUMENTS
JP   2009-280515   12/2009
JP   2011-121886   6/2011

OTHER PUBLICATIONS
Kono et al. Chem. Commun. 2010, 46, 3265-3267.*
Kono et al., "Dithienylbenzobis(thiadiazole) Based Organic Semiconductors With Low LUMO Levels and Narrow Energy Gaps," Chem. Commun., vol. 46, No. 19, pp. 3265-3267, Apr. 13, 2010.
Fujisaki et al., "Air-Stable n-Type Organic Thin-Film Transistor Array and High Gain Complementary Inverter on Flexible Substrate," Applied Physics Letters, vol. 97, No. 13, pp. 133303-1-133303-3, Sep. 27, 2010.
Facchetti et al., "Synthesis and Characterization of Diperfluoroocytl-Substituted Phenylene-Thiophene Oligomers as N-Type Semiconductors, Molecular Structure-Film Microstructure-Mobility Relationships, Organic Field-Effect Transistors, and Transistor Nonvolatile Memory Elements," Chem. Mater., vol. 16, No. 23, pp. 4715-4727, Sep. 4, 2004.

(Continued)

*Primary Examiner* — Matthew Coughlin
(74) *Attorney, Agent, or Firm* — Knobbe Martens Olson & Bear LLP

(57) ABSTRACT

A benzobis(thiadiazole) derivative represented by the formula (1):

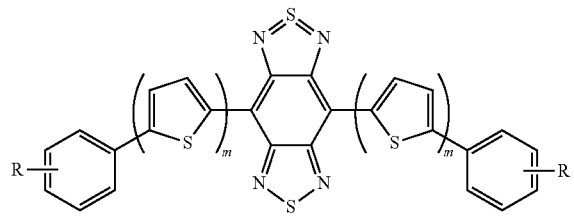

in which R represents a group containing at least one fluorine atom (with the proviso that fluorine atom (F) and trifluoromethyl group (—CF$_3$) are excluded), and
m represents an integer of from 1 to 10.

23 Claims, 12 Drawing Sheets

(56) References Cited

OTHER PUBLICATIONS

Usta et al., "N-Channel Semiconductor Materials Design for Organic Complementary Circuits," Accounts of Chemical Research, Vo. 44, No. 7, pp. 501-510, May 26, 2011.

International Preliminary Report on Patentability issued in PCT/JP2013/057567 dated Oct. 2, 2014.

Chengliang Wang et al, "Semiconducting π-Conjugated Systems in Field-Effect Transistors: A Material Odyssey of Organic Electronics," Chem. Rev., 2012, 112 (4), pp. 2208-2267.

* cited by examiner

BENZOBIS(THIADIAZOLE) DERIVATIVE AND ORGANIC ELECTRONICS DEVICE COMPRISING SAME

This application is the U.S. National Phase under 35 U.S.C. §371 of International Application No. PCT/JP2013/057567, filed Mar. 15, 2013, designating the U.S., and published in Japanese as WO 2013/141182 on Sep. 26, 2013, which claims priority to Japanese Patent Application No. 2012-067773, filed Mar. 23, 2012.

TECHNICAL FIELD

The present invention relates to a benzobis(thiadiazole) derivative, and organic electronic devices comprising the same, including an organic thin film transistor, an organic electroluminescence device, a display device, a display, and a photovoltaic cell (solar cell).

BACKGROUND ART

Benzobisthiazole compounds hitherto attract attention as compounds used for organic thin film transistors (organic TFTs), organic electroluminescence devices (organic EL devices), or organic thin film photovoltaic cells, and various derivatives, in which the main skeleton is benzobis(thiadiazole), are synthesized vigorously.

There is proposed a benzobisthiazole compound into which a strong electron-withdrawing group is introduced, in particular, in order to improve the hole-electron mobility or the stability in the atmosphere. For example, Non Patent Literature 1 and Non Patent Literature 2 disclose a compound in which trifluoromethylphenyl group is bound to benzobis(thiadiazole) via thienylene group (hereinafter, also referred to as "FPTBBT"). The compound has a mobility improved by the introduction of trifluoromethylphenyl group which is a strong electron-withdrawing group.

In addition, it is generally known that a compound having a strong electron-withdrawing group introduced into thiophene ring has an improved stability or mobility of electron, although the compound is not a compound in which the main skeleton is benzobis(thiadiazole). (See, for example, Patent Literature 1.)

CITATION LIST

Patent Literature

Patent Literature 1: JP-A-2009-280515

Non Patent Literature

Non Patent Literature 1: Chem. Commun., 46, 3265 (2010)
Non Patent Literature 2: Applied Physics Lett., 97, 133303 (2011)

SUMMARY OF INVENTION

Technical Problem

However, various derivatives in which the main skeleton is benzobis(thiadiazole) generally have very low solubility in organic solvents, and therefore it is very difficult to form a thin film from any of the derivatives by a coating method. In addition, any of the derivatives still has an inadequate mobility from a practical viewpoint.

Accordingly, an object of the present invention is to solve the above-mentioned problems, and to provide a benzobis(thiadiazole) derivative, which is soluble in an organic solvent and allows the formation of a thin film by a coating method, and has an excellent hole-electron mobility (field-effect mobility) and an excellent stability in the atmosphere. Another object of the present invention is to provide organic electronic devices comprising the benzobis(thiadiazole) derivative, including an organic thin film transistor, an organic electroluminescence device, a display device, a display, and a photovoltaic cell.

Solution to Problem

The present invention relates to the following items.

[1] A benzobis(thiadiazole) derivative represented by the formula (1):

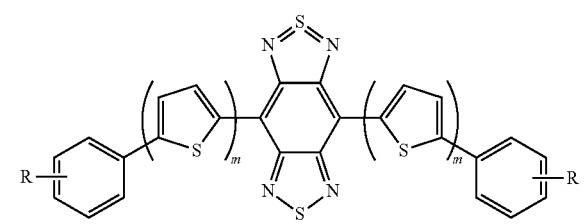

wherein

R represents a group containing at least one fluorine atom (with the proviso that fluorine atom (F) and trifluoromethyl group (—$CF_3$) are excluded), and m represents an integer of from 1 to 10.

[2] The benzobis(thiadiazole) derivative as described in [1], wherein the R group comprises a structure represented by any one of the formulae (A-1) to (A-3):

wherein $R^1$ represents hydrogen atom, fluorine atom, linear or branched alkyl group, or linear or branched alkyl group substituted with at least one fluorine atom.

[3] The benzobis(thiadiazole) derivative as described in [2], wherein the R group comprises a structure represented by any one of the formulae (B-1) to (B-6):

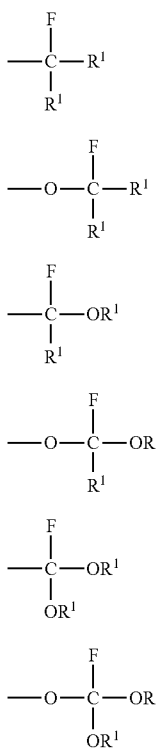

(B-1)

(B-2)

(B-3)

(B-4)

(B-5)

(B-6)

wherein $R^1$ represents hydrogen atom, fluorine atom, linear or branched alkyl group, or linear or branched alkyl group substituted with at least one fluorine atom, with the proviso that two $R^1$ groups may be the same as, or different from each other.

[4] The benzobis(thiadiazole) derivative as described in [3], wherein the R group comprises a structure represented by any one of the formulae (C-1) to (C-4):

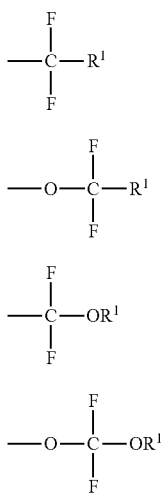

(C-1)

(C-2)

(C-3)

(C-4)

wherein $R^1$ represents hydrogen atom, fluorine atom, linear or branched alkyl group, or linear or branched alkyl group substituted with at least one fluorine atom.

[5] The benzobis(thiadiazole) derivative as described in [2], wherein the R group comprises a structure represented by any one of the formulae (D-1) to (D-6):

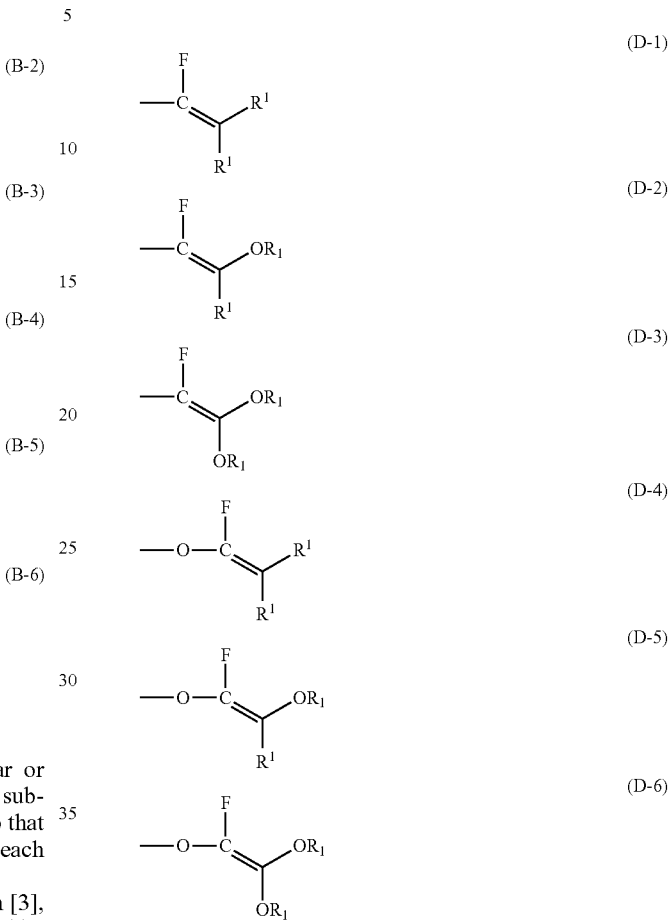

(D-1)

(D-2)

(D-3)

(D-4)

(D-5)

(D-6)

wherein $R^1$ represents hydrogen atom, fluorine atom, linear or branched alkyl group, or linear or branched alkyl group substituted with at least one fluorine atom, with the proviso that two $R^1$ groups may be the same as, or different from each other, and the double bond structure may be a cis-form, a trans-form, or any mixture thereof.

[6] The benzobis(thiadiazole) derivative as described in any one of [2] to [5], wherein the $R^1$ group is hydrogen atom, fluorine atom, linear or branched alkyl group containing 1 to 30 carbon atoms, or linear or branched alkyl group containing 1 to 30 carbon atoms and substituted with at least one fluorine atom.

[7] The benzobis(thiadiazole) derivative as described in [6], wherein the $R^1$ group is hydrogen atom, fluorine atom, linear or branched alkyl group containing 1 to 10 carbon atoms, or linear or branched alkyl group containing 1 to 10 carbon atoms and substituted with at least one fluorine atom.

[8] The benzobis(thiadiazole) derivative as described in any one of [2] to [7], wherein the $R^1$ group is hydrogen atom, fluorine atom, alkyl group, 1-fluoroalkyl group, 1,1-difluoroalkyl group, 1,1,2-trifluoroalkyl group, 1,1,2,2-tetrafluoroalkyl group, 1,1,2,2,3,3-hexafluoroalkyl group, 1,1,2,2,3,3,4,4-octafluoroalkyl group, 1,1,2,2,3,3,4,4,5,5- decafluoroalkyl group, 1,1,2,2,3,3,4,4,5,5,6,6-dodecafluoroalkyl group, 1,1,2,2,3,3,4,4,5,5,6,6,7,7-tetradecafluoroalkyl group, 1,1,2,2,3,3,4,4,5,5,6,6,7,7,8,8-hexadecafluoroalkyl group, 1,1,2,2,3,3,4,4,5,5,6,6,7,7,8,8,9,9-octadecafluoroalkyl group, or perfluoroalkyl group.

[9] The benzobis(thiadiazole) derivative as described in any one of [1] to [8], wherein the m is an integer of from 1 to 3.

[10] The benzobis(thiadiazole) derivative as described in any one of [1] to [9], wherein the benzobis(thiadiazole) derivative is soluble in an organic solvent.

[11] An organic semiconductor ink comprising the benzobis(thiadiazole) derivative as described in any one of [1] to [10].

[12] An organic semiconductor ink comprising two or more of organic semiconductors, wherein one or more of the organic semiconductors is the benzobis(thiadiazole) derivative as described in any one of [1] to [10].

[13] An organic electronic device comprising an organic layer, which comprises the benzobis(thiadiazole) derivative as described in any one of [1] to [10].

[14] An organic thin film transistor, comprising a gate electrode, a gate insulating layer, an organic semiconductor layer, a source electrode, and a drain electrode on a substrate, wherein
the organic semiconductor layer comprises the benzobis(thiadiazole) derivative as described in any one of [1] to [10].

[15] An organic electroluminescence device, comprising an anode, a luminescent layer, a hole transport layer and/or an electron transport layer, and a cathode on a substrate, wherein
the hole transport layer and/or the electron transport layer comprise the benzobis(thiadiazole) derivative as described in any one of [1] to [10].

[16] A display device, in which an organic electroluminescence device is driven/lighted using an organic thin film transistor, wherein
the organic thin film transistor is the organic thin film transistor as described in [14].

[17] An active-matrix display device, wherein
pixels are arranged in a matrix form, the pixel comprising the organic thin film transistor as described in [14] and an organic electroluminescence device.

[18] The display device as described in any one of [16] to [17], wherein the organic electroluminescence device is the organic electroluminescence device as described in [15].

[19] A display device, in which an organic electroluminescence device is driven/lighted using an organic thin film transistor, wherein
the organic electroluminescence device is the organic electroluminescence device as described in [15].

[20] An organic thin film photovoltaic cell, comprising an anode, a charge separation layer comprising a hole transport material and an electron transport material, and a cathode on a substrate, wherein
the charge separation layer comprises the benzobis(thiadiazole) derivative as described in any one of [1] to [10].

[21] An organic thin film photovoltaic cell, comprising an anode, a charge separation layer comprising a hole transport material and an electron transport material, a hole transport layer and/or an electron transport layer, and a cathode on a substrate, wherein
the hole transport layer and/or the electron transport layer comprise the benzobis(thiadiazole) derivative as described in any one of [1] to [10].

[22] The organic electronic device as described in [13], the organic thin film transistor as described in [14], the organic electroluminescence device as described in [15], the display device as described in any one of [16] to [19], or the organic thin film photovoltaic cell as described in [20] or [21], wherein
the substrate is a flexible substrate.

Advantageous Effects of Invention

According to the present invention, there may be provided a benzobis(thiadiazole) derivative (hereinafter, also referred to as "benzobis(thiadiazole) compound"), which is soluble in an organic solvent and allows the formation of a thin film by a coating method, and has an excellent hole-electron mobility (field-effect mobility) and an excellent stability in the atmosphere. It is industrially advantageous to be capable of forming a thin film (layer) by a coating method (or printing). The benzobis(thiadiazole) derivative of the present invention has an excellent hole-electron mobility (field-effect mobility) and an excellent stability in the atmosphere, and therefore may be suitably used for, for example, organic electronic devices including an organic thin film transistor, an organic electroluminescence device, a display device, a display, and a photovoltaic cell.

DESCRIPTION OF EMBODIMENTS

<Benzobis(thiadiazole) Compound>

Figure 1:
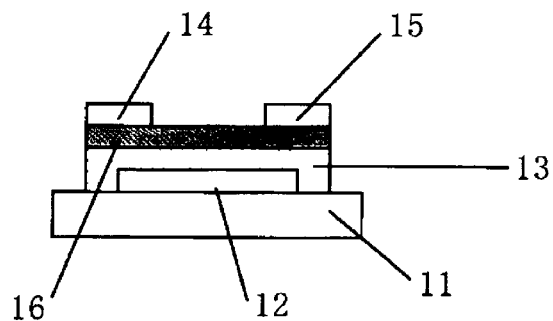
FIG. 1 is a longitudinal sectional view illustrating the layer configuration of one example of the organic thin film transistor (organic TFT) of the present invention.

The benzobis(thiadiazole) compound of the present invention is represented by the formula (1).

In the formula (1), R represents a group containing at least one fluorine atom (with the proviso that fluorine atom (F) and trifluoromethyl group ($-CF_3$) are excluded). It should be noted that, except for trifluoromethyl group ($-CF_3$), groups comprising trifluoromethyl group(s) such as $-OCF_3$ are not excluded.

Specifically, the R group preferably comprises a structure represented by the formula (A-1), or a structure represented by the formula (A-2), or a structure represented by the formula (A-3), and more preferably comprises a structure represented by any one of the formulae (B-1) to (B-6), or a structure represented by any one of the formulae (D-1) to (D-6).

In the formulae (A-1) to (A-3), the formulae (B-1) to (B-6), and the formulae (D-1) to (D-6), $R^1$ represents hydrogen atom, fluorine atom, linear or branched alkyl group, or linear or branched alkyl group substituted with at least one fluorine atom. In the formulae (B-1) to (B-6) and the formulae (D-1) to (D-6), however, two $R^1$ groups may be the same as, or different from each other.

The R group preferably comprises difluoromethylene group ($-CF_2-$), and preferably comprises a structure represented by any one of the formulae (C-1) to (C-4). In the formulae (C-1) to (C-4), $R^1$ represents hydrogen atom, fluorine atom, linear or branched alkyl group, or linear or branched alkyl group substituted with at least one fluorine atom, also.

The alkyl group, and the alkyl group substituted with at least one fluorine atom preferably contain 1 to 30 carbon atoms, and more preferably contain 1 to 10 carbon atoms. The alkyl group, and the alkyl group substituted with at least one fluorine atom may be linear or branched. In other words, the $R^1$ group is preferably hydrogen atom, fluorine atom, linear or branched alkyl group containing 1 to 30 carbon atoms, or linear or branched alkyl group containing 1 to 30 carbon atoms and substituted with at least one fluorine atom, and the $R^1$ group is more preferably hydrogen atom, fluorine atom, linear or branched alkyl group containing 1 to 10 carbon atoms, or linear or branched alkyl group containing 1 to 10 carbon atoms and substituted with at least one fluorine atom.

Specific examples of the alkyl group containing 1 to 30 carbon atoms include methyl group, ethyl group, propyl group, isopropyl group, butyl group, t-butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, and octadecyl group. Specific examples of the alkyl group containing 1 to 30 carbon atoms and substituted with at least one fluorine atom include trifluoromethyl group, difluoromethyl group, fluoromethyl group, pentafluoroethyl group, tetrafluoroethyl group, trifluoroethyl group, difluoroethyl group, monofluoroethyl group, heptafluoropropyl group, hexafluoropropyl group, pentafluoropropyl group, tetrafluoropropyl group, trifluoropropyl group, difluoropropyl group, monofluoropropyl group, nonafluorobutyl group, octafluorobutyl group, heptafluorobutyl group, hexafluorobutyl group, pentafluorobutyl group, tetrafluorobutyl group, trifluorobutyl group, difluorobutyl group, monofluorobutyl group, undecafluoropentyl group, decafluoropentyl group, nonafluoropentyl group, octafluoropentyl group, heptafluoropentyl group, hexafluoropentyl group, pentafluoropentyl group, tetrafluoropentyl group, trifluoropentyl group, difluoropentyl group, and monofluoropentyl group.

The number of fluorine atoms and the substitution position of fluorine atom are not particularly limited. In the formulae (A-1) to (A-3), the formulae (B-1) to (B-6), the formulae (C-1) to (C-4), and the formulae (D-1) to (D-6), the $R^1$ group is preferably fluorine atom, alkyl group, 1-fluoroalkyl group, 1,1-difluoroalkyl group, 1,1,2-trifluoroalkyl group, 1,1,2,2-tetrafluoroalkyl group, 1,1,2,2,3,3-hexafluoroalkyl group, 1,1,2,2,3,3,4,4-octafluoroalkyl group, 1,1,2,2,3,3,4,4,5,5-decafluoroalkyl group, 1,1,2,2,3,3,4,4,5,5,6,6-dodecafluoroalkyl group, 1,1,2,2,3,3,4,4,5,5,6,6,7,7-tetradecafluoroalkyl group, 1,1,2,2,3,3,4,4,5,5,6,6,7,7,8,8-hexadecafluoroalkyl group, 1,1,2,2,3,3,4,4,5,5,6,6,7,7,8,9,9-octadecafluoroalkyl group, or perfluoroalkyl group. Among them, groups containing 1 to 30 carbon atoms are preferred, and groups containing 1 to 10 carbon atoms are more preferred. In addition, in the formulae (B-1) to (B-6), and the formulae (D-1) to (D-6), two $R^1$ groups may be the same as, or different from each other.

It is also preferred that one of the two $R^1$ groups be hydrogen atom in the formulae (B-1) to (B-2). It is also preferred that the $R^1$ group be hydrogen atom in the formulae (C-1) to (C-2). It is also preferred that the $R^1$ group be hydrogen atom in the formulae (D-1) and (D-4).

The substitution position of the R group is not particularly limited, and the substitution position may be position 2 (ortho position) or position 3 (meta position) with respect to thienylene group, but may be preferably position 4 (para position) with respect to thienylene group.

In the formula (1), m, which represents the number of thienylene groups, represents an integer of from 1 to 10, and is preferably an integer of from 1 to 5, more preferably 1 to 3.

Examples of the benzobis(thiadiazole) compound of the present invention include compounds represented by the formulae (1-1) to (1-36).

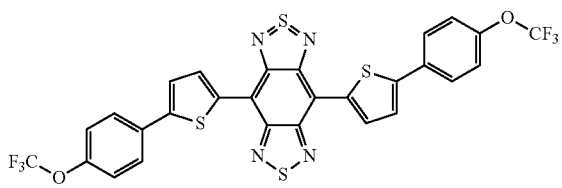

1-1 (BBT-(1))

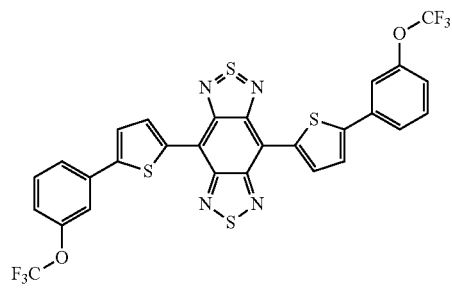

1-2 (BBT-(2))

-continued
1-3 (BBT-(3))
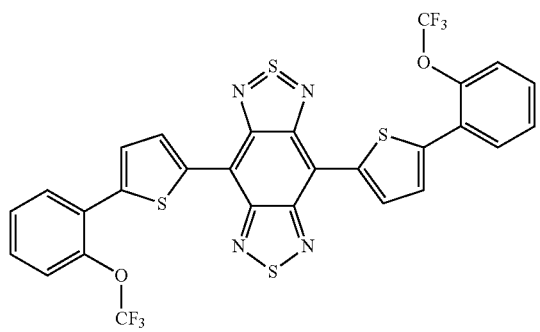
1-4 (BBT-(6))
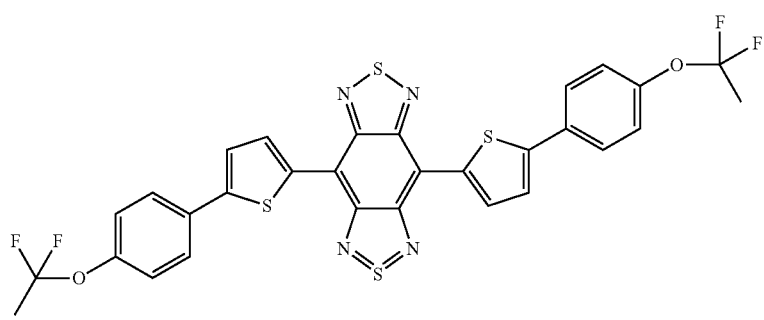
1-5
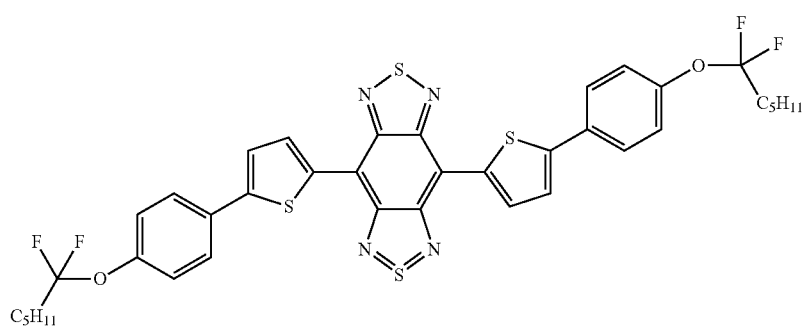
1-6 (BBT-(7))
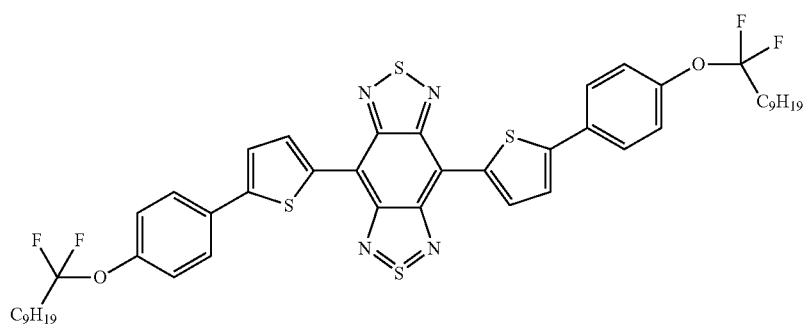
1-7 (BBT-(4))
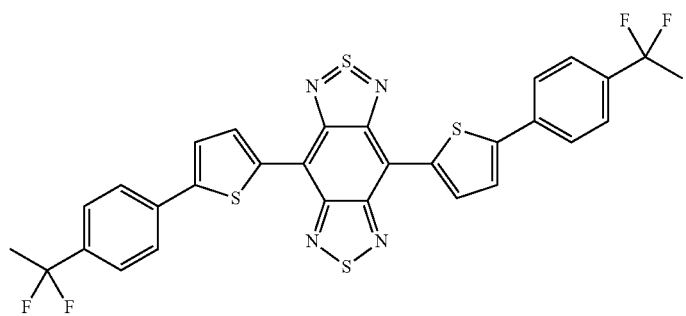

1-8
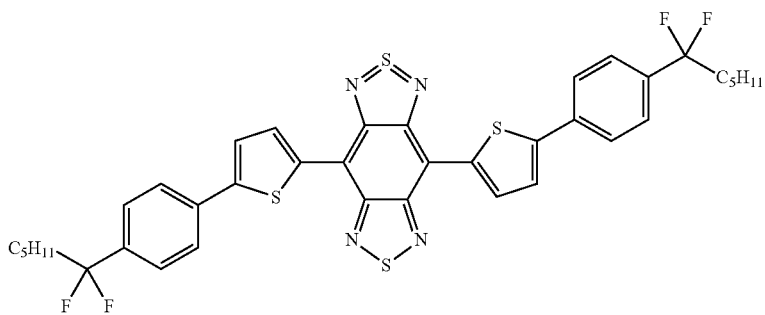
1-9 (BBT-(5))
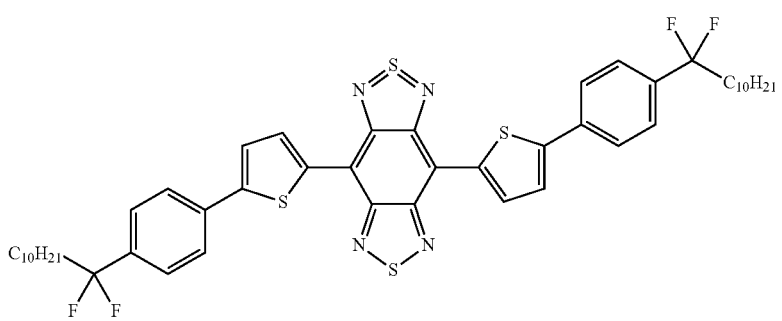
1-10
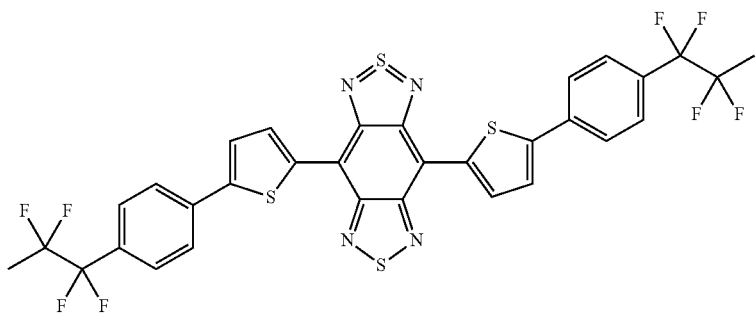
1-11
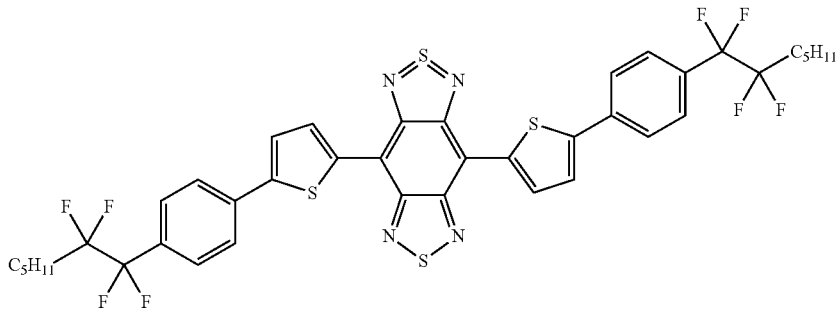
1-12
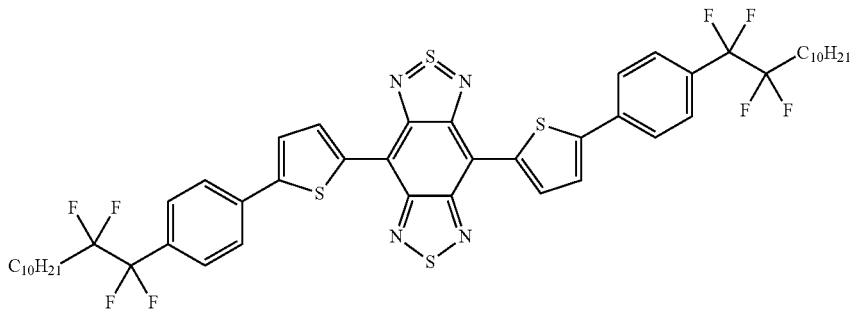

-continued
1-13 (BBT-(8))
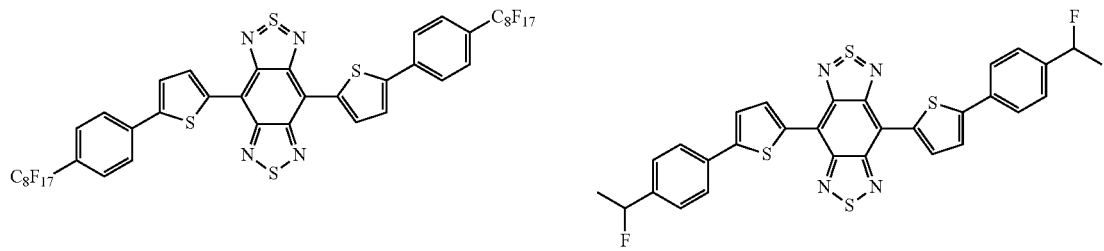
1-14
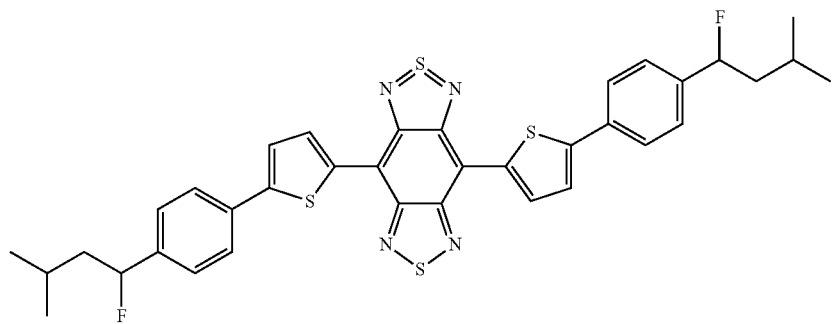
1-15 (BBT-(9))
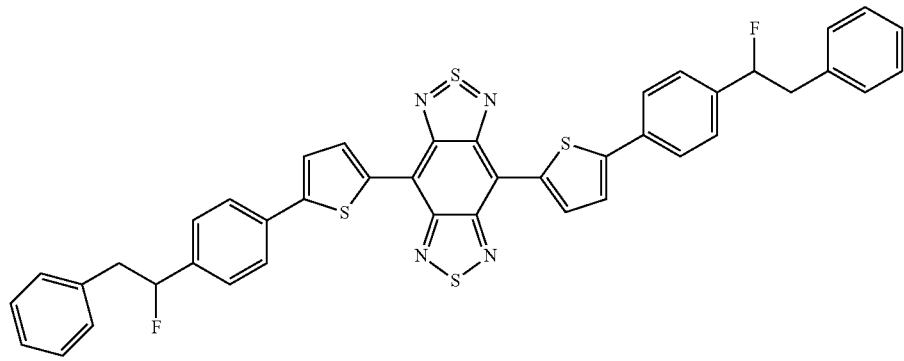
1-16
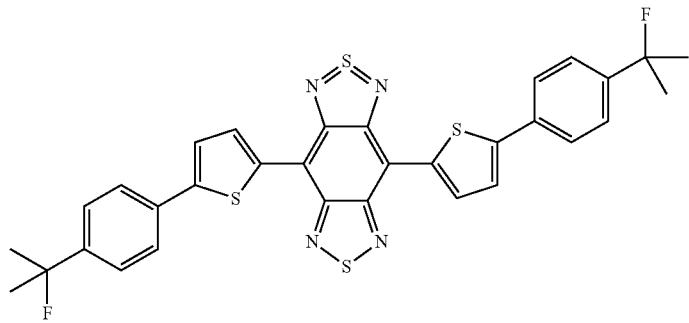
1-17
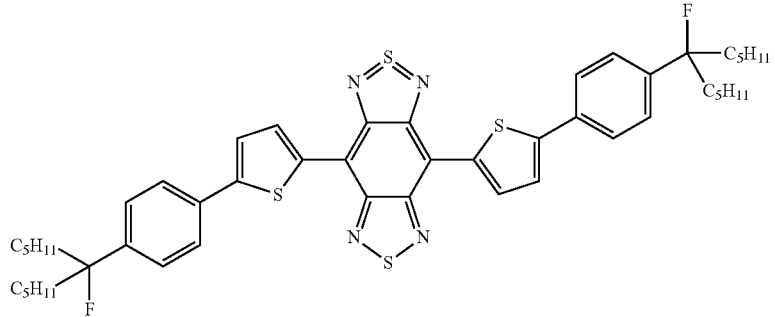
1-18

1-19
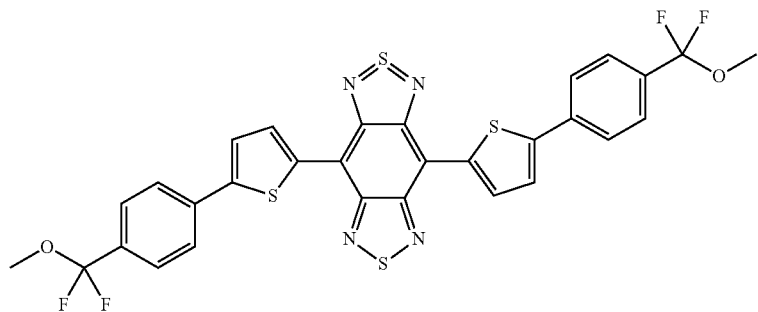
1-20
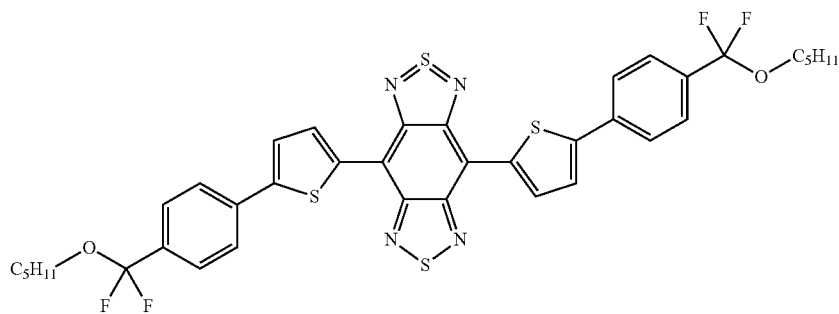
1-21 (BBT-(10))
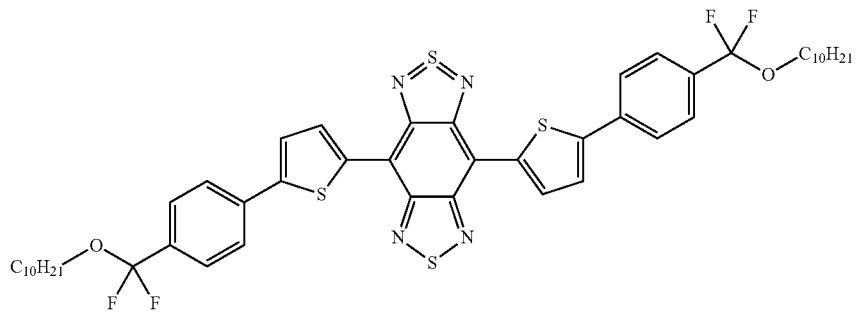
1-22 (BBT-(15))     1-23
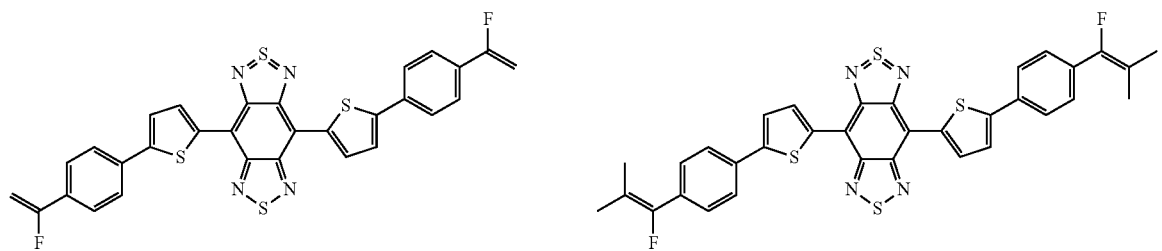
1-24
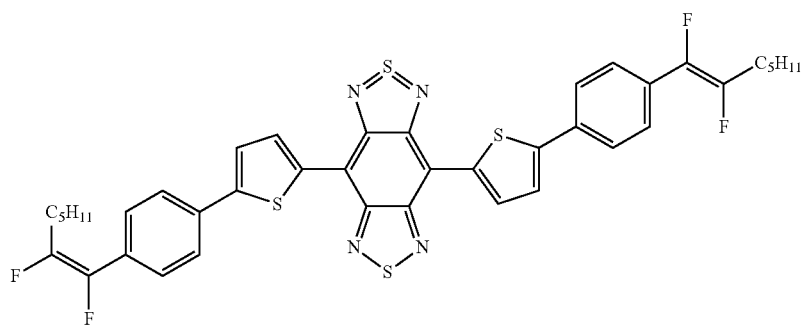

-continued
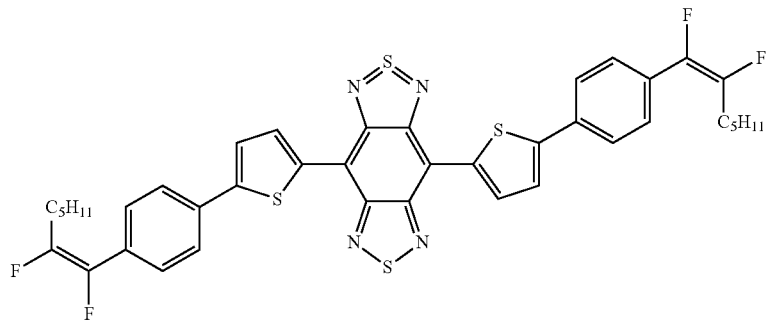
1-25
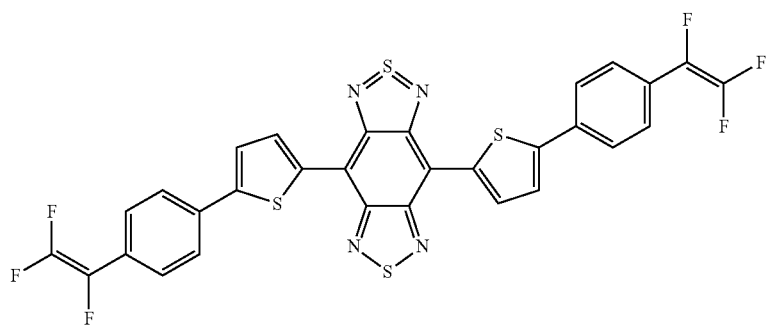
1-26
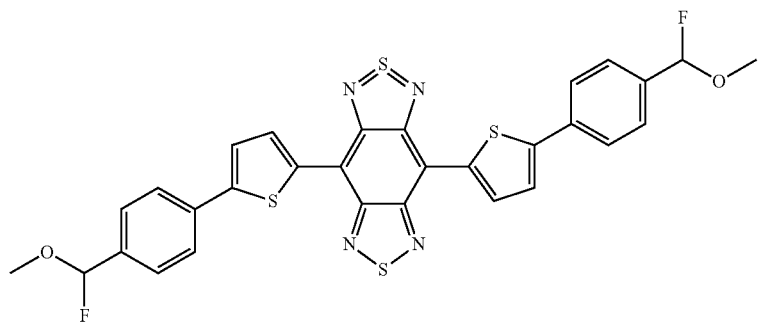
1-27
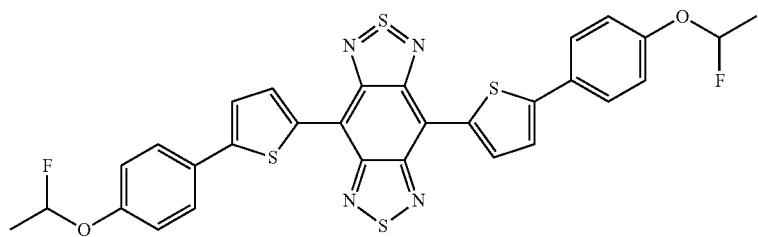
1-28
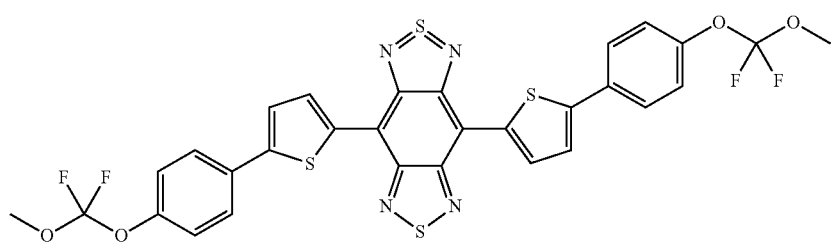
1-29

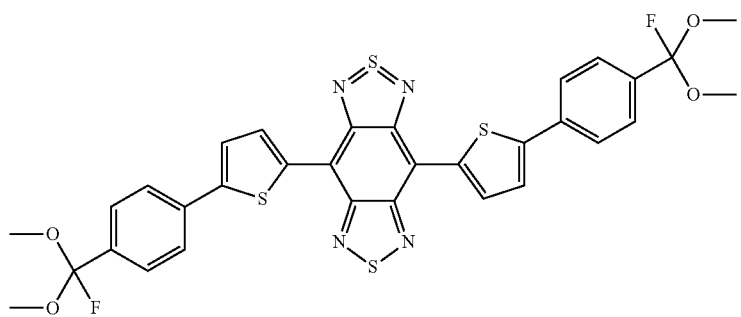
1-30
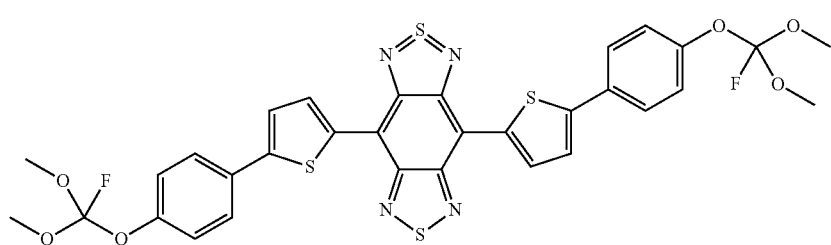
1-31
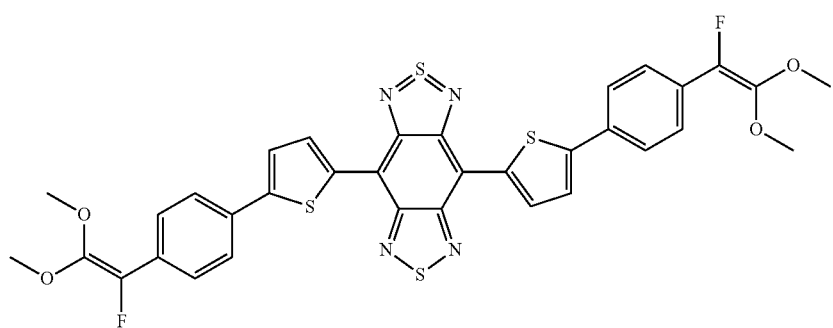
1-32
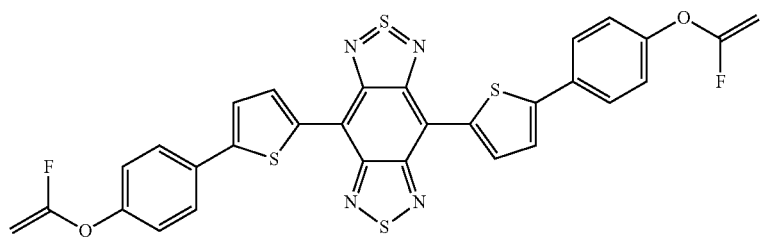
1-33 (BBT-(16))
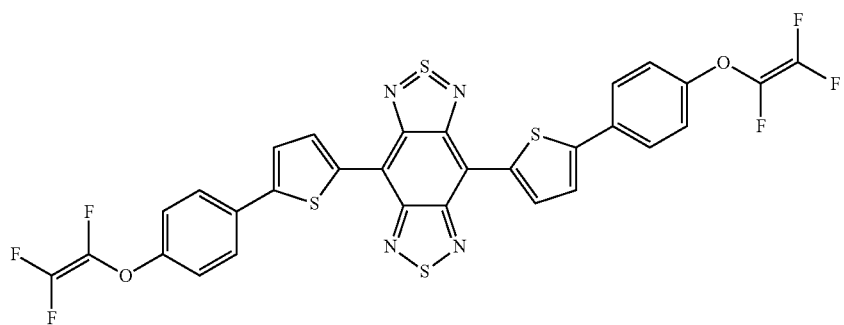
1-34

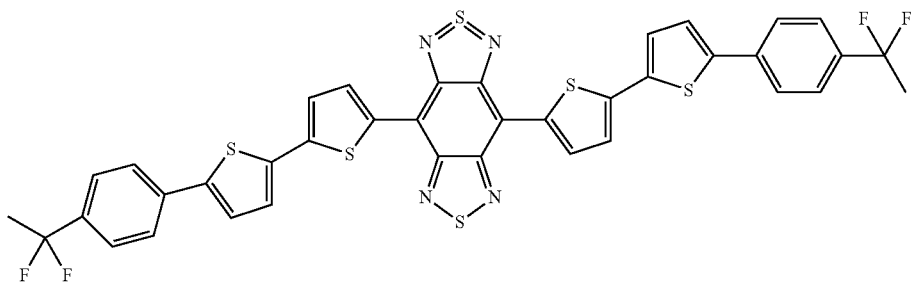
1-35

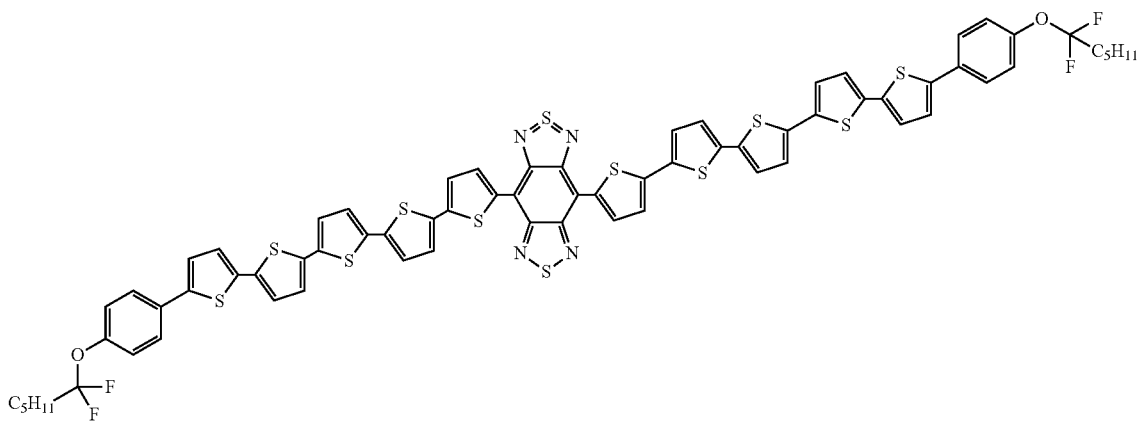
1-36

The benzobis(thiadiazole) compound of the present invention may be synthesized by reference to (1) Tetrahedron, Vol. 53, No. 29, p. 10169, 1997, or (2) Organic Letters, Vol. 12, No. 15, p. 3340, 2010, and in accordance with the following reaction scheme, for example.

In addition, a compound having a double bond may be synthesized by heating a compound having difluoromethylene group under a reduced pressure.

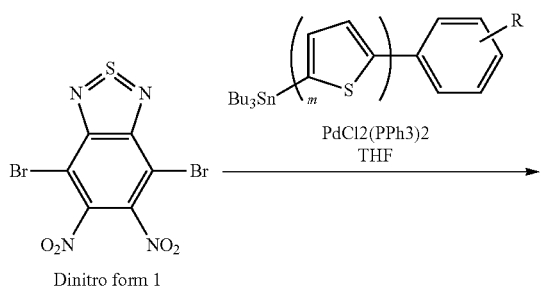
Dinitro form 1

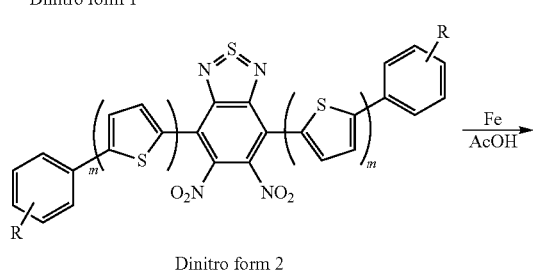
Dinitro form 2

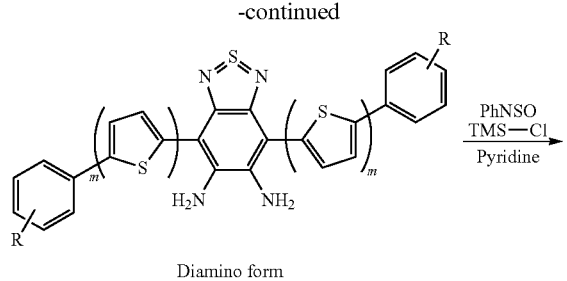
Diamino form

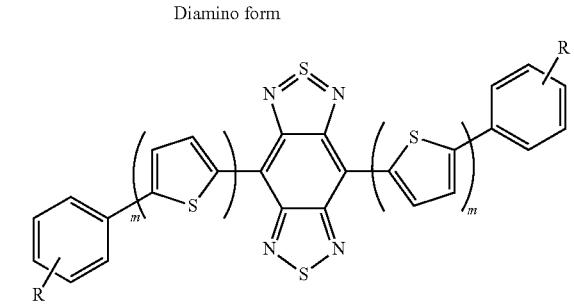
Benzobis(thiadiazole)

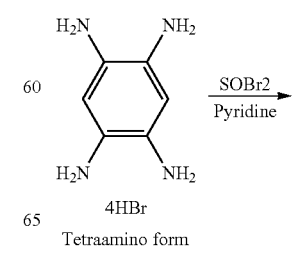
4HBr
Tetraamino form

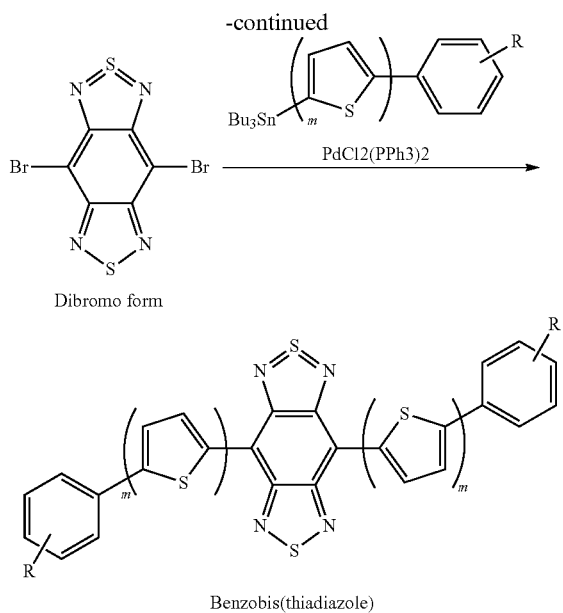

Dibromo form

Benzobis(thiadiazole)

After the completion of the reaction, the benzobis(thiadiazole) compound of the present invention may be isolated and purified from the obtained reaction solution by performing common operations such as filtration, concentration, extraction, distillation, sublimation, recrystallization, and column chromatography. In order to remove different impurities having different solubility from the compound and thereby improve the purity of the compound, Soxhlet extraction with an organic solvent is preferably incorporated into the purification step as it is simple.

The benzobis(thiadiazole) compound of the present invention is generally soluble in water; and various organic solvents including alcohols such as methanol, ethanol, propanol, and ethylene glycol; ketones such as acetone, methyl ethyl ketone, methyl isobutyl ketone, and cyclohexanone; esters such as methyl acetate, ethyl acetate, butyl acetate, and methyl benzoate; amides such as N,N-dimethylformamide, N,N-dimethylacetamide, and N-methyl pyrrolidone; ureas such as 1,3-dimethyl-2-imidazolidinone, and 1,3-dimethylimidazolidine-2,4-dione; sulfoxides such as dimethyl sulfoxide, and diethyl sulfoxide; sulfones such as sulfolane; nitriles such as acetonitrile, and propionitrile; ethers such as diethyl ether, diisopropyl ether, tetrahydrofuran, and dioxane; aromatic hydrocarbons such as benzene, toluene, xylene, and mesitylene; halogenated aromatic hydrocarbons such as chlorobenzene, 1,2-dichlorobenzene, 1,2,4-trichlorobenzene, bromobenzene, and 1,2-dibromobenzene; and halogenated aliphatic hydrocarbons such as dichloromethane, and chloroform. Among them, halogenated aromatic hydrocarbons, aromatic hydrocarbons, and halogenated aliphatic hydrocarbons may be preferably used as the solvent. These solvents may be used singly, or may be used in combination of two or more.

Accordingly, the benzobis(thiadiazole) compound of the present invention may be dissolved in such an organic solvent, and the obtained solution may be used as an organic semiconductor ink.

The organic semiconductor ink of the present invention comprises one or more the benzobis(thiadiazole) compounds of the present invention, and may comprise one or more other organic semiconductors. As the solvent of the ink, one solvent may be used alone, or two or more solvents may be mixed and used. In addition, the organic semiconductor ink of the present invention may comprise additives to control the properties of the ink, such as additives to adjust the viscosity of the ink, and additives to control the hydrophilicity or the water repellency of the ink.

The content of the benzobis(thiadiazole) compound of the present invention in the ink is not particularly limited, and may be appropriately selected. For example, the content may be from about 0.001 wt % to about 10 wt %, and may be preferably from about 0.01 wt % to about 1 wt % from the viewpoint of film-forming properties.

Examples of the other organic semiconductor include polymer semiconductor compounds. The polymer semiconductor compound as used herein is a polymer compound characterized by exhibiting semiconductor properties, and specific examples thereof include polyacetylene polymer, polydiacetylene polymer, polyparaphenylene polymer, polyaniline polymer, polytriphenylamine polymer, polythiophene polymer, polypyrrole polymer, polyparaphenylenevinylene polymer, polyethylenedioxythiophene polymer, copolymers comprising naphthalenediimide as one component, copolymers comprising perylenediimide as one component, and copolymers comprising diketopyrrolopyrrole as one component. Among these polymer semiconductor compounds, polyaniline polymer, polythiophene polymer, polypyrrole polymer, polyparaphenylenevinylene polymer, copolymers comprising naphthalenediimide as one component, copolymers comprising perylenediimide as one component, copolymers comprising diketopyrrolopyrrole as one component, and the like are preferred.

Additional examples of the other organic semiconductor include low-molecular-weight semiconductor compounds other than the benzobis(thiadiazole) compound of the present invention. The low-molecular-weight semiconductor compound as used herein is a low-molecular-weight compound characterized by exhibiting semiconductor properties, and specific examples thereof include acene derivatives, phenylenevinylene derivatives, triphenylamine derivatives, fluorene derivatives, azaacene derivatives, thienoacene derivatives, thiophene derivatives, benzothiophene derivatives, thienothiophene derivatives, thiazole derivatives, thiazolothiazole derivatives, tetrathiafulvalene derivatives, phthalocyanine derivatives, porphyrin derivatives, naphthalenediimide derivatives, perylenediimide derivatives, benzothiadiazole derivatives, naphthobisthiadiazole derivatives, diketopyrrolopyrrole derivatives, and fullerene derivatives. Among these low-molecular-weight semiconductor compounds, acene derivatives, thienoacene derivatives, thiophene derivatives, thienothiophene derivatives, tetrathiafulvalene derivatives, naphthalenediimide derivatives, perylenediimide derivatives, diketopyrrolopyrrole derivatives, fullerene derivatives, and the like are preferred.

In addition, examples of the other organic semiconductor include organic semiconductors described in Chem. Rev., 2012, Vol. 112, pp. 2208-2267.

The organic semiconductor ink of the present invention may also comprise an insulating polymer compound as an additive component, as necessary. The insulating polymer compound as used herein is synthetic resin, plastic, synthetic rubber, or the like, and specific examples thereof include polyethylene, polypropylene, polyvinyl chloride, polystyrene, polyester, phenol resin, acrylic resin, amide resin, nylon, vinylon, polyisoprene, polybutadiene, acrylic rubber, acrylonitrile rubber, and urethane rubber. The effect of the addition thereof includes the optimization of the viscosity of the ink, and the improvement in the film-forming properties of the ink.

In addition, the organic semiconductor ink of the present invention may comprise a conductive polymer compound as an additive component, as necessary. The conductive polymer compound as used herein is a polymer compound characterized by exhibiting electrical conductivity, and specific examples thereof include polyacetylene polymer, polydiacetylene polymer, polyparaphenylene polymer, polyaniline polymer, polytriphenylamine polymer, polythiophene polymer, polypyrrole polymer, polyparaphenylenevinylene polymer, polyethylenedioxythiophene polymer, and a mixture of polyethylenedioxythiophene and polystyrene sulfonic acid (generic name: PEDOT-PSS). Among these conductive polymer compounds, polyacetylene polymer, polyparaphenylene polymer, polyaniline polymer, polytriphenylamine polymer, polythiophene polymer, polypyrrole polymer, and polyparaphenylenevinylene polymer are preferred. The effect of the addition thereof includes the improvement in the charge mobility, as well as the optimization of the viscosity of the ink, the improvement in the film-forming properties of the ink, and the like.

A layer, or a thin film of the benzobis(thiadiazole) compound of the present invention may be formed by coating of an organic semiconductor ink comprising the benzobis(thiadiazole) compound. The coating of the organic semiconductor ink comprising the benzobis(thiadiazole) compound of the present invention may be performed by any known methods such as spin-coating method, ink-jet method, casting method, and Langmuir-Blodgett method. In addition, any known method commonly known as printing technique may be applied as the coating method, and the printing may be performed by, for example, ink-jet method, screen method, offset method, gravure method, flexographic method, microcontact method, or the like.

The organic semiconductor ink of the present invention provides a layer, or a thin film comprising the benzobis(thiadiazole) compound of the present invention by coating, or printing a substrate with the ink, and then removing the solvent component from the ink. The conditions of the removal of the solvent component may be appropriately selected.

It is preferred that the solvent component be naturally-dried, or air-dried at room temperature, for example. Meanwhile, in the cases where the solvent has a high boiling point, and therefore is hard to remove, the solvent may be removed at around room temperature under a reduced pressure, or alternatively, the solvent may be removed by heating at about 50° C. to about 200° C., or alternatively, the solvent may be removed by the combination of both of them and by heating under a reduced pressure.

In addition, for the purpose of improving the semiconductor properties of the layer or thin film comprising the benzobis(thiadiazole) compound of the present invention, the layer or thin film comprising the benzobis(thiadiazole) compound may be subjected to heat treatment. In this case, the conditions of the heat treatment may be appropriately selected, and examples thereof include a process in which the layer or thin film is heated at a temperature of from about 50° C. to about 250° C. for 0.1 hour to 24 hours. The step may double as the solvent removal step.

In addition, for the purpose of improving the semiconductor properties of the layer or thin film comprising the benzobis(thiadiazole) compound of the present invention, the layer or thin film comprising the benzobis(thiadiazole) compound may be subjected to treatment by exposure to a vapor of a solvent.

Examples of the solvent used in this step include various organic solvents, including alcohols such as methanol, ethanol, propanol, and ethylene glycol; ketones such as acetone, methyl ethyl ketone, methyl isobutyl ketone, and cyclohexanone; esters such as methyl acetate, ethyl acetate, butyl acetate, and methyl benzoate; amides such as N,N-dimethylformamide, N,N-dimethylacetamide, and N-methyl pyrrolidone; ureas such as 1,3-dimethyl-2-imidazolidinone, and 1,3-dimethylimidazolidine-2,4-dione; sulfoxides such as dimethyl sulfoxide, and diethyl sulfoxide; sulfones such as sulfolane; nitriles such as acetonitrile, and propionitrile; ethers such as diethyl ether, diisopropyl ether, tetrahydrofuran, and dioxane; aromatic hydrocarbons such as benzene, toluene, xylene, and mesitylene; halogenated aromatic hydrocarbons such as 1,2-dichlorobenzene, 1,2,4-trichlorobenzene, bromobenzene, and 1,2-dibromobenzene; and halogenated aliphatic hydrocarbons such as dichloromethane, and chloroform. Among them, halogenated aromatic hydrocarbons, aromatic hydrocarbons, and halogenated aliphatic hydrocarbons may be preferably used as the solvent. These solvents may be used singly, or may be used in combination of two or more.

The solvent vapor exposure treatment step is performed, for example, by leaving the layer or thin film comprising the benzobis(thiadiazole) compound and a solvent, without the direct contact of the layer or thin film comprising the benzobis(thiadiazole) compound with the solvent, in an enclosed space. In order to increase the amount of the solvent vapor, the solvent may be heated at a temperature of from about 40° C. to about 150° C. Subsequent to the solvent vapor exposure treatment step, the solvent removal step and subsequent steps may be appropriately selected.

The benzobis(thiadiazole) compound of the present invention has excellent hole-electron mobility (field-effect mobility), and therefore may be suitably used for, for example, organic electronic devices such as an organic thin film transistor, an organic electroluminescence device, a display device, a display, and a photovoltaic cell. In addition, the benzobis(thiadiazole) compound of the present invention may find extensive application in fields such as backlight, optical communication, electrophotography, illuminating light source, recording light source, exposing light source, reading light source, sign, signboard, and interior goods.

<Organic Thin Film Transistor>

The organic thin film transistor of the present invention (hereinafter, referred to as "organic TFT") will be described below. The organic thin film transistor of the present invention comprises an organic semiconductor layer comprising the benzobis(thiadiazole) derivative of the present invention. It is effective to use the benzobis(thiadiazole) derivative of the present invention for a semiconductor layer of an organic TFT, because the orientation direction of the molecule may be readily aligned and high field-effect mobility may be achieved.

Any known structure and any known material may be used for the organic thin film transistor of the present invention, except that the semiconductor layer comprises the benzobis(thiadiazole) derivative of the present invention.

It is preferred that the thickness of the semiconductor layer be thin, as long as the layer does not lose its necessary function. The thickness of the semiconductor layer to perform its necessary function is generally 1 nm to 10 µm, preferably 5 nm to 5 µm, and more preferably 10 nm to 1 µm.

FIG. 1 shows the layer configuration of one example of the organic TFT of the present invention. The organic TFT shown in FIG. 1 has a bottom gate-top contact structure, and is formed by laminating a gate electrode 12, a gate insulating layer 13, an organic semiconductor layer 16, and a drain electrode 14 and a source electrode 15, in this order, on a substrate 11.

As the substrate 11, materials such as glass, quartz, silicon and ceramic, and plastic materials may be used, for example.

As the gate electrode 12, metals such as gold, platinum, chromium, tungsten, tantalum, nickel, copper, aluminum, silver, magnesium and calcium, and alloys thereof, and materials such as polysilicon, amorphous silicon, graphite, tin-doped indium oxide (ITO), zinc oxide and conductive polymer may be used, for example. The gate electrode 12 may be formed by well-known film-formation methods such as vacuum deposition, electron-beam evaporation deposition, RF sputtering, and printing.

As the gate insulating layer 13, materials such as $SiO_2$, $Si_3N_4$, SiON, $Al_2O_3$, $Ta_2O_5$, amorphous silicon, polyimide resin, polyvinyl phenol resin, polyparaxylylene resin, polystyrene resin, and polymethyl methacrylate resin may be used, for example. The gate insulating layer 13 may be formed by well-known film-formation methods as listed for the gate electrode 12.

In the organic thin film transistor of the present invention, the organic semiconductor layer 16 comprises one or more the benzobis(thiadiazole) derivatives of the present invention, and may be formed by well-known film-formation methods such as vacuum deposition, and spin-coating, for example. The organic semiconductor layer 16 may be formed by coating (printing) methods such as spin-coating, because the benzobis(thiadiazole) compound of the present invention is soluble in an organic solvent. In addition, the organic semiconductor layer 16 may comprise one or more other organic compounds.

As the drain electrode 14 and the source electrode 15, metals such as gold, platinum, chromium, tungsten, tantalum, nickel, copper, aluminum, silver, magnesium and calcium, and alloys thereof, and materials such as polysilicon, amorphous silicon, graphite, tin-doped indium oxide (ITO), zinc oxide and conductive polymer may be used, for example. The drain electrode 14 and the source electrode 15 may be formed by well-known film-formation methods as listed for the gate electrode 12.

<Organic Electroluminescence Device>

The organic electroluminescence device of the present invention (hereinafter, referred to as "organic EL device") will be described below. The organic EL device of the present invention comprises a hole transport layer and/or an electron transport layer comprising the benzobis(thiadiazole) derivative of the present invention. It is effective to use the benzobis(thiadiazole) derivative of the present invention for a hole transport layer and/or an electron transport layer of an organic EL device, because the benzobis(thiadiazole) derivative has excellent hole and electron transport properties.

Any known structure and any known material may be used for the organic EL device of the present invention, except that the hole transport layer and/or the electron transport layer comprises the benzobis(thiadiazole) derivative of the present invention.

The organic EL device is a device in which at least one or more organic compound layers, including a luminescent layer, are formed between an anode and a cathode. The organic EL device is typically configured to have a device structure of (anode/hole transport layer/luminescent layer/cathode), (anode/luminescent layer/electron transport layer/cathode), (anode/hole transport layer/luminescent layer/electron transport layer/cathode), or the like.

Figure 2:
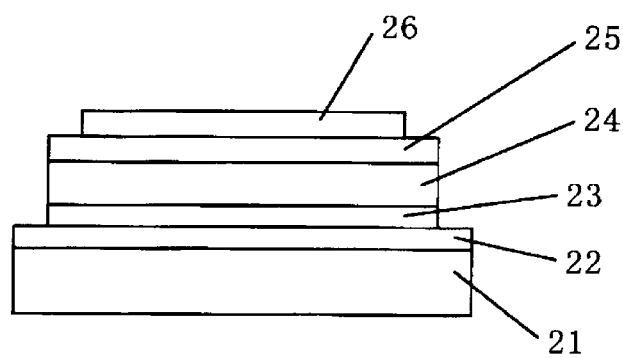
FIG. 2 is a longitudinal sectional view illustrating the layer configuration of one example of the organic EL device of the present invention.

FIG. 2 shows the layer configuration of one example of the organic EL device of the present invention. The organic EL device shown in FIG. 2 is formed by laminating an anode 22, a hole transport layer 23, a luminescent layer 24, an electron transport layer 25, and a cathode 26, in this order, on a substrate 21.

When a predetermined direct voltage is applied between the anode 22 and the cathode 26 of the organic EL device configured as described above, light with high intensity is emitted from the luminescent layer 24. The mechanism of light emission is considered as follows.

Specifically, when a predetermined direct voltage is applied between the two layers as described above, holes which flow from the anode 22 to the hole transport layer 23 are transported to the luminescent layer 24. Meanwhile, electrons which are injected from the cathode 26 to the electron transport layer 25 are transported to the luminescent layer 24. In the luminescent layer 24, electrons diffuse and migrate, and recombine with holes to achieve a state of electrically neutralization. When the recombination occurs, a certain energy is released, and the organic luminescent material in the luminescent layer 24 is excited to the excitation state by the energy. When the material returns to the ground state from the excited state, light is emitted.

When the benzobis(thiadiazole) derivative of the present invention, which has high field-effect mobility, is used for the hole transport layer 23 and/or the electron transport layer 25 of the organic EL device, holes and electrons may be efficiently injected into the luminescent layer, and therefore the luminous efficiency may be enhanced.

As the substrate 21, transparent materials such as glass and plastics may be used, for example.

As the anode 22, a light-transmission material is generally used. Specifically, tin-doped indium oxide (ITO), indium oxide, tin oxide, and indium oxide-zinc oxide alloy may be preferably used. A thin film of metal such as gold, platinum, silver, and magnesium alloy may also be used. In addition, organic materials such as polyaniline, polythiophene, polypyrrole, and derivatives thereof may be used. The anode 22 may be formed by well-known film-formation methods such as vacuum deposition, electron-beam evaporation deposition, RF sputtering, and coating (printing).

As the cathode 26, alkali metals such as Li, K and Na, and alkali-earth metals such as Mg and Ca, which have small work function, may be preferably used, from the viewpoint of electron injection properties. In addition, Al which is stable, and the like may be preferably used. In order to achieve both stability and electron injection properties, the cathode may be a layer comprising two or more materials, and the materials are described in detail, for example, in JP-A-H02-15595, JP-A-H05-121172, etc. The cathode 26 may be formed by well-known film-formation methods such as vacuum deposition, electron-beam evaporation deposition, and RF sputtering.

As the luminescent layer 24, a host material such as quinolinol complex and aromatic amine doped with (doping) a coloring material such as coumarin derivatives, DCM, quinacridone and rubrene may be preferably used. The luminescent layer 24 may also be formed from a host material only. In addition, a high-efficiency organic EL device may be produced by forming the luminescent layer 24 doped with iridium metal complex. The luminescent layer 24 may be formed by well-known film-formation methods such as vacuum deposition, sputtering, and coating (printing).

The benzobis(thiadiazole) derivative of the present invention is used for the hole transport layer 23 and/or the electron transport layer 25. The benzobis(thiadiazole) derivative may be used singly, or may be used in combination of two or more. In addition, the hole transport layer 23 and the electron transport layer 25 may comprise one or more other compounds.

In the cases where the benzobis(thiadiazole) derivative of the present invention is not used for the hole transport layer 23, materials such as N,N'-bis(3-methylphenyl)-N,N'-bis (phenyl)-benzidine (TPD), N,N'-bis(naphthalene-1-yl)-N, N'-bis(phenyl)-2,2'-dimethyl benzidine (α-NPD), and 2,2-bis (3-(N,N-di-p-tolylamino)phenyl)biphenyl (3DTAPBP), for example, may be used as the hole transport layer 23. In the cases where the benzobis(thiadiazole) derivative of the present invention is not used for the electron transport layer 25, materials such as 2-(4-biphenyl)-5-(4-tert-butylphenyl)-1,3,4-oxazole (PBD), 1,3-bis[2-(4-tert-butylphenyl)-1,3,4-oxadiazo-5-yl]benzene (OXD-7), and 2,2',2"-(1,3,5-benzinetriyl)-tris(1-phenyl-1-H-benzimidazole) (TPBi), for example, may be used as the electron transport layer 25.

As the method of film-formation of the hole transport layer 23 and the electron transport layer 25, the methods as listed for the method of film-formation of the luminescent layer 24 may be used. In addition, the hole transport layer 23 and the electron transport layer 25 may be formed by coating (printing) methods such as spin-coating, because the benzobis (thiadiazole) compound of the present invention is soluble in an organic solvent.

The organic luminescence device of the present invention may be configured to comprise an electron injection layer, a hole injection layer, an electron blocking layer, a hole blocking layer, a protective layer, and the like, in addition to the layers as described above. These layers may be formed by the methods as listed for the method of film-formation of the luminescent layer 24.

<Display Device>

The display device of the present invention will be described below. In the display device of the present invention, the driving and lighting of the organic EL device is controlled by the organic TFT, and the organic TFT is the organic TFT of the present invention as described above, or the organic EL device is the organic EL device of the present invention as described above. As for the display device of the present invention, it is preferred that the organic TFT is the organic TFT of the present invention, and the organic EL device is the organic EL device of the present invention.

Figure 3:
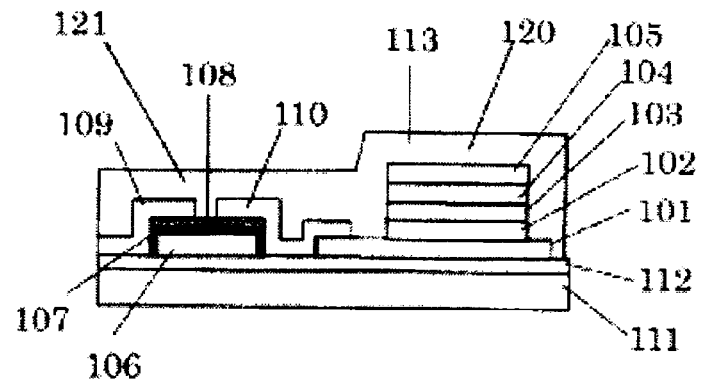
FIG. 3 is a longitudinal sectional view illustrating the layer configuration of one example of the display device of the present invention.

FIG. 3 shows one example of the display device of the present invention. The display device shown in FIG. 3 has an organic EL device 120 comprising a cathode 101, an electron transport layer 102, a luminescent layer 103, a hole transport layer 104 and an anode 105, and an organic TFT 121 comprising a gate electrode 106, a gate insulating layer 107, an organic semiconductor layer 108, a source electrode 109 and a drain electrode 110 on a substrate 111 with a barrier layer 112 therebetween. The upper side of the layer structure is coated with a protective film 113.

The display device has a structure in which the cathode 101 of the organic EL device 120 (electrode closer to the substrate 111) is electrically connected to the drain electrode 110 of the organic TFT 121. When a voltage is applied to the gate electrode 106, an electric current flows between the source electrode and the drain electrode, and the organic EL device 120 emits light. In addition, the display device may have a structure in which the anode is electrically connected to the drain electrode of the organic TFT.

In the present invention, it is preferred that the organic TFT and the organic EL device which is driven/lighted by the organic TFT are the organic TFT of the present invention and the organic EL device of the present invention, respectively, both of which comprise the benzobis(thiadiazole) derivative of the present invention, as described above. Meanwhile, one of them may comprise no benzobis(thiadiazole) derivative of the present invention, and may be formed from a known material and have a known structure.

In addition, an active-matrix organic EL display may be formed by arranging devices (pixels) for switching as shown in FIG. 3, in which the organic TFT and the organic EL device are combined, in a matrix form. The active-matrix organic EL display has the advantages of having a low possibility of the application of unnecessary voltage to a non-selected point even in the case of a great number of pixels; having a low possibility of the efficiency reduction and deterioration even in high-duty operation; and having excellent response properties.

Any known structure and any known material may be used for the display device (display) of the present invention, except that the organic TFT of the present invention and/or the organic EL device of the present invention are employed. The display device (display) may be produced by any known method.

<Photovoltaic Cell>

The photovoltaic cell of the present invention (hereinafter, referred to as "organic PV device") will be described below. The organic PV device of the present invention comprises at least one of a charge separation layer comprising a hole transport material and an electron transport material, a hole transport layer, and an electron transport layer, which comprise the benzobis(thiadiazole) derivative of the present invention. It is effective to use the benzobis(thiadiazole) derivative of the present invention for a charge separation layer and/or a hole transport layer and/or an electron transport layer of an organic PV device, because the benzobis(thiadiazole) derivative has excellent hole and electron transport properties.

Any known structure and any known material may be used for the organic PV device of the present invention, except that at least one of the charge separation layer, the hole transport layer and the electron transport layer comprises the benzobis (thiadiazole) derivative of the present invention.

The organic PV device is a device in which at least one or more organic compound layers, including a charge separation layer, are formed between an anode and a cathode. The organic PV device is typically configured to have a device structure of (anode/charge separation layer/cathode), (anode/ charge separation layer/electron transport layer/cathode), (anode/hole transport layer/charge separation layer/electron transport layer/cathode), or the like.

Figure 4:
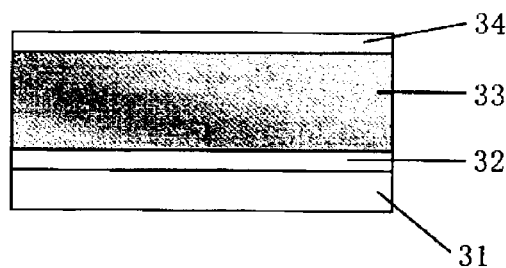
FIG. 4 is a longitudinal sectional view illustrating the layer configuration of one example of the photovoltaic cell of the present invention.

FIG. 4 shows the layer configuration of one example of the organic PV device of the present invention. The organic PV device shown in FIG. 4 is formed by laminating an anode 32, a charge separation layer 33, and a cathode 34, in this order, on a substrate 31.

When the organic PV device configured as described above is irradiated with light, holes and electrons are generated in the charge separation layer 33, and an electric current is taken out if the anode 32 is connected to the cathode 34. The mechanism of generation of electricity is considered as follows.

Specifically, when the charge separation layer 33 is irradiated with light as described above, the light is absorbed, and the organic molecule is excited by the energy to provide charge separation, and generate holes and electrons. The holes are transported to the anode 32 by the hole transport material in the charge separation layer 33, and the electrons are transported to the cathode 34 by the electron transport material in the charge separation layer 33 and taken out to the external circuit.

When the benzobis(thiadiazole) derivative of the present invention, which has high field-effect mobility, is used for the charge separation layer 33 of the organic PV device, holes and electrons may be efficiently taken out from the charge separation layer 33, and therefore the electricity generation efficiency may be enhanced. In addition, when the benzobis(thiadiazole) derivative of the present invention is used for the hole transport layer and the electron transport layer, holes may be efficiently transported to the anode and electrons may be efficiently transported to the cathode, respectively, and therefore the electricity generation efficiency may be enhanced.

As the substrate 31, transparent materials such as glass and plastics may be used, for example.

As the anode 32, a light-transmission material is generally used. Specifically, tin-doped indium oxide (ITO), indium oxide, tin oxide, and indium oxide-zinc oxide alloy may be preferably used. A thin film of metal such as gold, platinum, silver, and magnesium alloy may also be used. In addition, organic materials such as polyaniline, polythiophene, polypyrrole, and derivatives thereof may be used. The anode 32 may be formed by well-known film-formation methods such as vacuum deposition, electron-beam evaporation deposition, RF sputtering, and coating (printing).

As the cathode 34, alkali metals such as Li, K and Na, and alkali-earth metals such as Mg and Ca, which have small work function, may be preferably used, from the viewpoint of electron taking-out properties. In addition, Al which is stable, and the like may be preferably used. In order to achieve both stability and electron taking-out properties, the cathode may be a layer comprising two or more materials. The cathode 34 may be formed by well-known film-formation methods such as vacuum deposition, electron-beam evaporation deposition, and RF sputtering.

The benzobis(thiadiazole) derivative of the present invention is used for the charge separation layer 33. The benzobis(thiadiazole) derivative may be used singly, or may be used in combination of two or more. In addition, the charge separation layer 33 may comprise one or more other compounds.

Examples of the materials constituting the charge separation layer in addition to the benzobis(thiadiazole) derivative include poly(3-hexylthiophene-2,5-diyl) (P3HT) and poly[2-methoxy-5-(2-ethylhexyloxy)-1,4-phenylenevinylene] (MEH-PPV), as the hole transport material, and fullerene C60, (6,6)-phenyl-C61-butyric acid methyl ester (C61-PCBM), fullerene C70 and (6,6)-phenyl-C71-butyric acid methyl ester (C71-PCBM), as the electron transport material.

The charge separation layer 33 may be formed by well-known film-formation methods such as vacuum deposition, sputtering, and coating (printing). In addition, the charge separation layer 33 may be formed by coating (printing) methods such as spin-coating, because the benzobis(thiadiazole) compound of the present invention is soluble in an organic solvent.

The organic PV device of the present invention may further comprise a hole transport layer and/or an electron transport layer. The benzobis(thiadiazole) derivative of the present invention may be preferably used for these layers. The benzobis(thiadiazole) derivative may be used singly, or may be used in combination of two or more. In addition, the hole transport layer and the electron transport layer may comprise one or more other compounds.

In the cases where the benzobis(thiadiazole) derivative of the present invention is not used for the hole transport layer or the electron transport layer, materials such as poly(3,4-ethylenedioxythiophene)-poly(styrenesulfonate) (PEDOT-PSS), for example, may be used as the hole transport layer, and materials such as 2,9-dimethyl-4,7-diphenyl-1,10-phenanthroline (BCP), for example, may be used as the electron transport layer. As the method of film-formation of the hole transport layer and the electron transport layer, the methods as listed for the method of film-formation of the charge separation layer 33 may be used.

In the organic electronic device, or organic thin film device, which comprises the benzobis(thiadiazole) derivative of the present invention, a plastic substrate may be used as the substrate. The plastic to be used as the substrate needs to have excellent heat resistance, dimensional stability, solvent resistance, electrical insulation property, processability, low air permeability, and low hygroscopicity. Examples of the plastic include polyethylene terephthalate, polyethylene naphthalate, polystyrene, polycarbonate, polyacrylate, and polyimide.

In the case of plastic substrate, it is preferred that a moisture-permeation blocking layer (gas barrier layer) be formed on the electrode side of the substrate, or the side opposite to the electrode, or on both sides. As the materials constituting the moisture-permeation blocking layer, inorganic materials such as silicon nitride and silicon oxide may be preferably used. The moisture-permeation blocking layer may be formed by well-known film-formation methods such as RF sputtering. In addition, a hard-coating layer or an undercoating layer may be formed as necessary.

EXAMPLES

The present invention will be more specifically described below with reference to the Examples. However, the scope of the present invention should not be limited to these Examples.

Example 1-1

Synthesis of BBT-(1)

(Step 1-A: Synthesis of Compound (1-1))

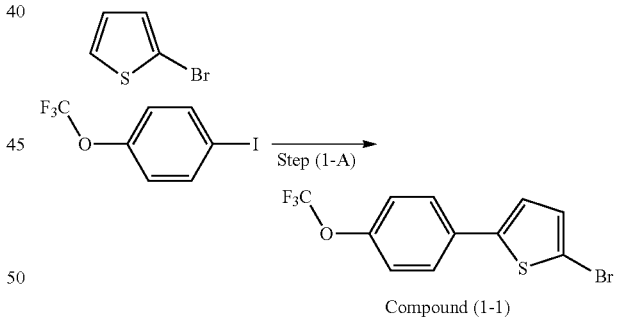

Compound (1-1)

Into a 1000-ml glass reaction vessel equipped with a thermometer and a stirring apparatus were placed 3.0 g (4.3 mmol) of palladium chloride, 10 g (174 mmol) of potassium fluoride, 25 g (86.8 mmol) of 4-(trifluoromethoxy)iodobenzene, 17 g (104.2 mmol) of 2-bromothiophene, 14.2 g (86.8 mmol) of silver nitrate, and 500 ml of anhydrous dimethyl sulfoxide. The mixture was subjected to freeze-pump-thaw (cycle) twice. The mixture was heated at 100° C. for 5 hours in argon atmosphere, and then cooled to room temperature. Inorganic substances were removed by filtration with Celite, and then the solvent was distilled off using a vacuum pump. The crude product obtained was purified by column chromatography (silica gel:hexane), to provide 16.7 g of Compound (1-1) in the form of a light yellow solid.

The properties of Compound (1-1) were as follows.
¹H-NMR (300 MHz; CDCl₃); δ (ppm) 7.01-7.04 (m, 2H), 7.20-7.24 (m, 2H), 7.49-7.54 (m, 2H)
CI-MS; 324 (M+1)
(Step 1-B: Synthesis of Compound (1-2))

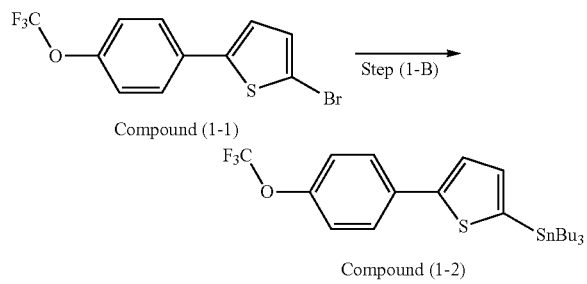

Into a 500-ml glass reaction vessel equipped with a thermometer and a stirring apparatus were placed 15 g (46.4 mmol) of Compound (1-1), and 300 ml of anhydrous tetrahydrofuran. The mixture was cooled to −65° C. While the internal temperature was kept at −65° C., 33.6 ml (53.4 mmol) of solution of t-butyl lithium in tetrahydrofuran was added dropwise to the mixture, and then the mixture was stirred for 30 minutes. Subsequently, 15.7 ml (58 mmol) of tributyl tin chloride was added dropwise to the mixture. The mixture was stirred at the same temperature for 1 hour, and then reacted at room temperature for 1 hour, and the reaction solution was filtered with neutral alumina. The solvent was distilled off, and the residue was purified by column chromatography (C8-modified silica gel:water-acetonitrile=40:60→0:100 vol %), to provide 18.8 g of Compound (1-2) in the form of a yellow liquid.

The properties of Compound (1-2) were as follows.
¹H-NMR (300 MHz; CDCl₃); δ (ppm) 0.88-0.93 (m, 9H), 1.10-1.16 (m, 6H), 1.29-1.42 (m, 6H), 1.51-1.64 (m, 6H), 7.13-7.14 (m, 1H), 7.18-7.22 (m, 2H), 7.39-7.40 (m, 1H), 7.61-7.64 (m, 2H)
CI-MS; 535 (M+2)

(Step 1-C: Synthesis of Compound (1-3))

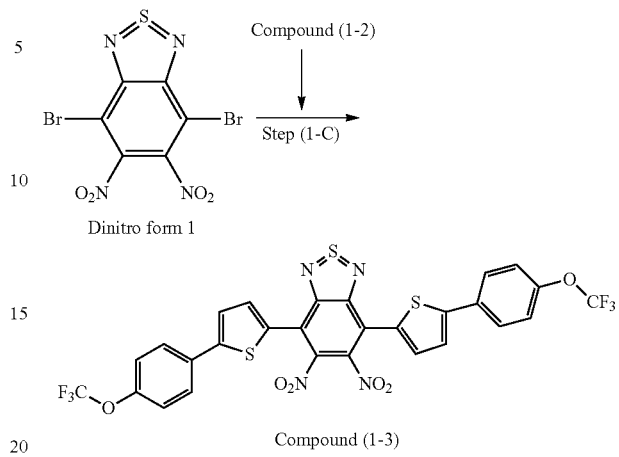

Into a 200-ml glass reaction vessel equipped with a thermometer and a stirring apparatus were placed 2.95 g (7.7 mmol) of Dinitro form 1, 9.0 g (16.9 mmol) of Compound (1-2), 1.08 g (1.54 mmol) of bistriphenylphosphine palladium dichloride, and 80 ml of anhydrous tetrahydrofuran. The mixture was subjected to freeze-pump-thaw (cycle) twice, and then refluxed for 5 hours. The reaction was carried out again in the same amounts by the same operations. Subsequently, the reaction solutions from the two sets of reactions were combined, and then 100 ml of saturated aqueous solution of potassium fluoride was added to the combined reaction solution, and the mixture was stirred for 30 minutes. Subsequently, the reaction solution was subjected to extraction with 700 ml of chloroform twice, and then the extract was dried over magnesium sulfate, and the solvent was distilled off. The residue was purified by column chromatography (silica gel: hexane-ethyl acetate=90:10→50:50 vol %), to provide 13.5 g of Compound (1-3) in the form of a red solid.

The properties of Compound (1-3) were as follows.
EI-MS; 710 (M+)

(Step 1-D: Synthesis of Compound (1-4))

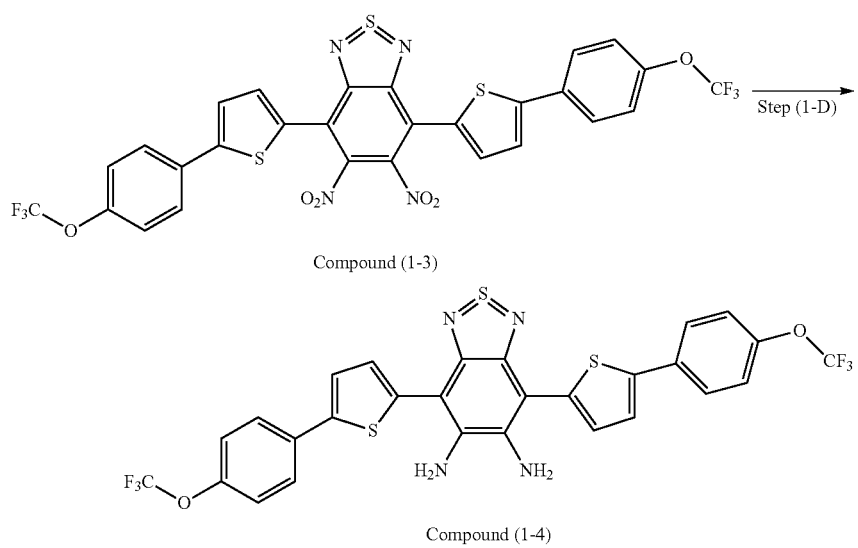

Into a 200-ml glass reaction vessel equipped with a thermometer and a stirring apparatus were placed 13 g (18.3 mmol) of Compound (1-3), 12.3 g (220 mmol) of iron powder, and 130 ml of acetic acid. The temperature of the mixture was increased from room temperature to 100° C., and then the mixture was reacted at 100° C. for 1.5 hours. Subsequently, the reaction mixture was cooled to room temperature, and then inorganic substances were removed by filtration, and the solvent was distilled off. The obtained solid was purified by column chromatography (silica gel:hexane-ethyl acetate=50:50 vol %), to provide 5.7 g of Compound (1-4) in the form of a brown solid.

The properties of Compound (1-4) were as follows.

$^1$H-NMR (300 MHz; CDCl$_3$); δ (ppm) 4.49 (brs, 2H), 7.23-7.27 (m, 2H), 7.36-7.38 (m, 2H), 7.42-7.43 (m, 2H), 7.65-7.71 (m, 2H)

EI-MS; 650 (M+)

(Step 1-E: Synthesis of BBT-(1); Crude Product 1)

(Purification Step 2: Recrystallization for Purification of BBT-(1); Crude Product 3)

Into a 2000-ml glass reaction vessel equipped with a thermometer and a stirring apparatus were placed 900 mg of the BBT-(1) (Crude product 2) and 1800 ml of toluene. The mixture was heated to reflux, to provide a homogeneous solution. The solution was cooled at room temperature, and then left for 2 days, and the formed solid was collected by filtration, to provide 0.5 g of BBT-(1) (Crude product 3) in the form of a dark green crystal with metallic luster.

(Purification Step 3: Sublimation for Purification of BBT-(1); Purified Product)

Into a sublimation purification apparatus equipped with a decompression device and a heat source was placed 0.41 g of the BBT-(1) (Crude product 3). And then, the BBT-(1) was subjected to sublimation for purification at a temperature of 250° C. to 350° C. and a reduced pressure of $0.6 \times 10^{-3}$ Pa to $2.8 \times 10^{-3}$ Pa, to provide 310 mg of BBT-(1) (purified product)

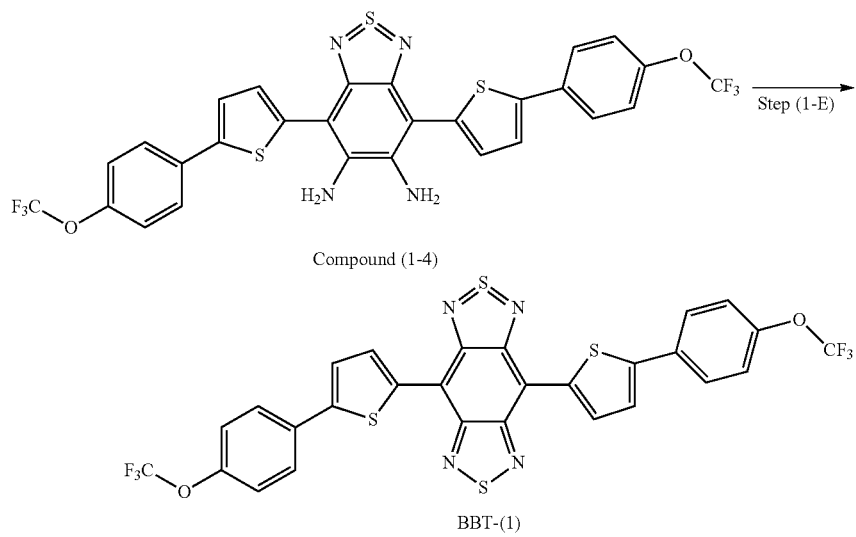

Compound (1-4)

BBT-(1)

Into a 200-ml glass reaction vessel equipped with a thermometer and a stirring apparatus were placed 5 g (7.7 mmol) of Compound (1-4), and 100 ml of anhydrous pyridine. The mixture was heated to 80° C. Subsequently, 1.85 ml (16.1 mmol) of N-thionylaniline was added dropwise to the mixture, and then 9.7 ml (76.8 mmol) of trimethylsilyl chloride was added dropwise thereto over 1 minute. The mixture was reacted for 8 hours. Subsequently, the solvent was distilled off, and then 150 ml of methanol was added to the obtained solid, and the mixture was refluxed for purification for 15 minutes, and then the formed solid was obtained. The reflux for purification with 150 ml of methanol was repeated twice, to provide 2.93 g of BBT-(1) (Crude product 1) in the form of a dark green solid.

(Purification Step 1: Reflux for Purification of BBT-(1); Crude Product 2)

Into a 300-ml glass reaction vessel equipped with a stirring apparatus were placed 2.56 g of the BBT-(1) (Crude product 1) and 200 ml of chloroform. The mixture was refluxed for purification for 3 hours. Subsequently, the formed solid was subjected to filtration with heat, to provide 2.24 g of BBT-(1) (Crude product 2) in the form of a dark green solid.

in the form of dark green powder (Isolated yield based on 4-(trifluoromethoxy)iodobenzene: 5.7%).

The properties of BBT-(1) (purified product) were as follows.

$^1$H-NMR (400 MHz; DMSO-d$_6$, 180° C.); δ (ppm) 7.60-7.62 (m, 4H), 7.91 (brs, 2H), 8.06-8.13 (m, 4H), 9.18 (brs, 2H)

CI-MS; 678 (M+)

Elemental Analysis;

Theoretical value (carbon) 49.55%, (hydrogen) 1.78%, (nitrogen) 8.26%, (fluorine) 16.8%, (sulfur) 18.90%

Measured value (carbon) 49.9%, (hydrogen) 2.0%, (nitrogen) 8.3%, (fluorine) 16%, (sulfur) 19%

[Solubility Experiment 1]

Into a 20-ml glass vessel equipped with a stirring apparatus were placed 5 mg of BBT-(1), and 1.6 g of 1,2-dichlorobenzene. The mixture was heated to 150° C., and BBT-(1) was completely dissolved in the solvent, to provide a green solution.

[Solubility Experiment 2]

Into a 20-ml glass vessel equipped with a stirring apparatus were placed 5 mg of BBT-(1), and 1.6 g of mesitylene. The mixture was heated to 100° C., and BBT-(1) was completely dissolved in the solvent, to provide a green solution.

[Thin Film Formation Experiment using Coating Method]

A solution of BBT-(1) in 1,2-dichlorobenzene, which was prepared in accordance with [Solubility Experiment 1], was filtered through a 0.2-μm filter, and then dropped onto a commercially available silicon wafer having a thermally grown silicon dioxide with a film thickness of 200 nm formed on the surface. And then, without any treatment, the solvent component was volatilized, and the formation of a thin film of BBT-(1) was confirmed. Meanwhile, a solution of BBT-(1) in mesitylene, which was prepared in accordance with [Solubility Experiment 2], was filtered through a 0.2-μm filter, and then dropped onto a silicon wafer as described above. And then, without any treatment, the solvent component was volatilized, and the formation of a thin film of BBT-(1) was confirmed.

On the other hand, using BBT-(11): (FPTBBT) synthesized in Reference Example 1, instead of BBT-(1), the preparation of a solution of BBT-(11) in 1,2-dichlorobenzene was attempted in accordance with [Solubility Experiment 1]. BBT-(11), however, was not completely dissolved in the solvent, to provide a suspension. The suspension was filtered through a 0.2-μm filter, and then dropped onto a silicon wafer as described above. And then, without any treatment, the solvent component was volatilized, but the formation of a thin film of BBT-(11) was not confirmed. Meanwhile, using BBT-(11), instead of BBT-(1), the preparation of a solution of BBT-(11) in mesitylene was attempted in accordance with [Solubility Experiment 2]. BBT-(11), however, was not completely dissolved in the solvent, to provide a suspension. The suspension was filtered through a 0.2-μm filter, and then dropped onto a silicon wafer as described above. And then, without any treatment, the solvent component was volatilized, but the formation of a thin film of BBT-(11) was not confirmed.

Example 1-2

Synthesis of Compound BBT-(2)

(Step (2-A): Synthesis of Compound (2-1))

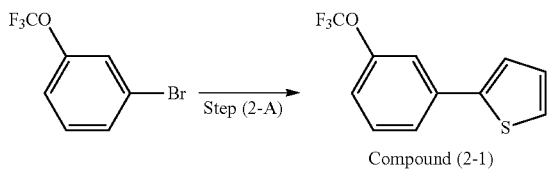 [SMILES: FC(F)(F)Oc1cccc(Br)c1 ; FC(F)(F)Oc1cccc(-c2cccs2)c1]

Compound (2-1)

Into a 300-ml glass reaction vessel equipped with a stirring apparatus were placed 14.0 g (58 mmol) of 1-bromo-3-(trifluoromethoxy)benzene, 4.1 g (5.8 mmol) of dichlorobis(triphenylphosphine)palladium(II), 28.2 g (76 mmol) of 2-(tributyltin)thiophene, and 140 ml of anhydrous toluene. The mixture was reacted at an internal temperature of about 100° C. for 4 hours. After the completion of the reaction, the solvent was concentrated, and then 400 ml of hexane was added to the concentrate, and the mixture was filtered through [silica gel:potassium carbonate=90:10 (wt %)]. The filtrate was concentrated, and the concentrate was subjected to distillation under a reduced pressure, to provide 17.3 g of a colorless liquid (boiling point: 132° C.-148° C./2.0 kPa).

Subsequently, 8.0 g of the distillate was purified by silica gel column chromatography (hexane: 100 vol %), to provide 5.0 g of Compound (2-1) in the form of a colorless liquid.

The properties of Compound (2-1) were as follows.

$^1$H-NMR (400 MHz; CDCl$_3$); 7.07-7.11 (m, 1H), 7.10-7.16 (m, 1H), 7.29-7.35 (m, 2H), 7.35-7.42 (m, 1H), 7.42-7.47 (m, 1H), 7.50-7.55 (m, 1H)

(Step (2-B): Synthesis of Compound (2-2))

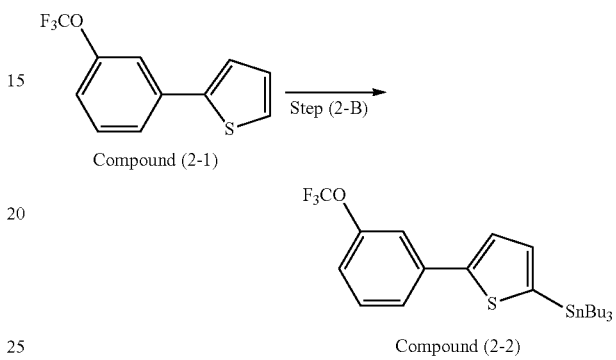

Into a 100-ml glass reaction vessel equipped with a stirring apparatus were placed 5.0 g (20.5 mmol) of Compound (2-1), and 50 ml of anhydrous tetrahydrofuran. While the internal temperature was kept at −60° C. or lower, 16.6 ml (27 mmol) of 1.6 N solution of n-butyl lithium in hexane was added to the mixture. The mixture was stirred at the same temperature for 30 minutes, and then 9.0 g (27 mmol) of tributyl tin chloride was added to the mixture at the same temperature. The temperature of the mixture was increased to room temperature, and the mixture was stirred overnight. And then, a THF-water mixture solution was added to the reaction solution for quenching, and the solvent was distilled off. Subsequently, hexane was added to the concentrate, and the mixture was filtered through [silica gel:potassium carbonate=90:10 (wt %)]. The filtrate was concentrated, and the concentrate was purified by reverse phase silica gel column chromatography (acetonitrile:water=60:40 to 95:5 vol %), to provide 10.0 g of Compound (2-2) in the form of a pale yellow liquid.

The properties of Compound (2-2) were as follows.

$^1$H-NMR (400 MHz; CDCl$_3$); 0.86-0.95 (m, 9H), 1.03-1.24 (m, 6H), 1.26-1.42 (m, 6H), 1.48-1.72 (m, 6H), 7.06-7.12 (m, 1H), 7.10-7.20 (m, 1H), 7.33-7.41 (m, 1H), 7.42-7.48 (m, 2H), 7.51-7.58 (m, 1H)

TOF-HRMS (ASAP+); 477 (M-C4H9)

(Step (2-C): Synthesis of BBT-(2))

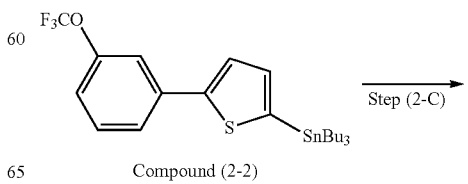

Compound (2-2)

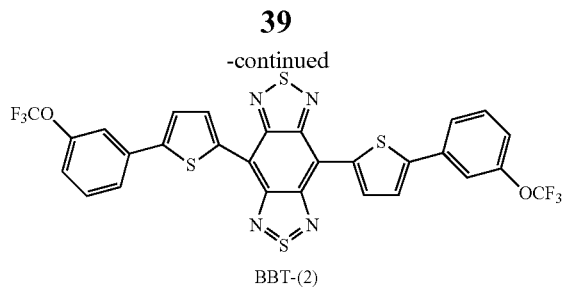

BBT-(2)

Into a 100-ml glass reaction vessel equipped with a stirring apparatus were placed 8.5 g (16 mmol) of Compound (2-2), 1.4 g (4.0 mmol) of dibromobenzobisthiadiazole (hereinafter, referred to as "Dibromo form"), 0.84 g (1.2 mmol) of dichlorobis(triphenylphosphine)palladium(II), and 50 ml of anhydrous toluene. The mixture was reacted at an internal temperature of about 100° C. for 6 hours. Subsequently, the reaction solution was filtered, to provide 2.1 g of a crude product. A portion of the crude product was purified, to provide 0.25 g of BBT-(2) in the form of a green solid.

The properties of BBT-(2) were as follows.

$^1$H-NMR (400 MHz; deuterated dichlorobenzene: 140° C.); 7.01-7.12 (m, 2H), 7.22-7.34 (m, 2H), 7.41-7.49 (m, 2H), 7.55-7.66 (m, 4H), 8.97-9.06 (m, 2H)

TOF-HRMS (ASAP−); 677.9750 (M−); Calcd. 677.9747

Example 1-3

Synthesis of Compound BBT-(3)

(Step (3-A): Synthesis of Compound (3-1))

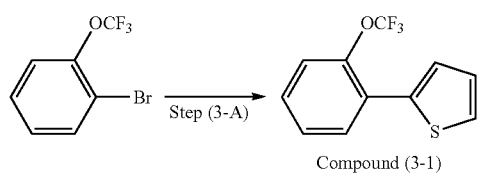 [SMILES: FC(F)(F)Oc1ccccc1Br ; FC(F)(F)Oc1ccccc1-c1cccs1]

Compound (3-1)

Into a 300-ml glass reaction vessel equipped with a stirring apparatus were placed 10.0 g (42 mmol) of 1-bromo-2-(trifluoromethoxy)benzene, 2.9 g (4.2 mmol) of dichlorobis(triphenylphosphine)palladium(II), 20.1 g (54 mmol) of 2-(tributyltin)thiophene, and 100 ml of toluene. The mixture was reacted at an internal temperature of about 100° C. for 4 hours. After the completion of the reaction, the solvent was concentrated, and then 300 ml of hexane was added to the reaction solution. Subsequently, the mixture was filtered through [silica gel:potassium carbonate=90:10 (wt %)]. The filtrate was concentrated, and the concentrate was purified by column chromatography (hexane: 100 vol %), to provide 6.6 g of Compound (3-1) in the form of a pale yellow liquid.

The properties of Compound (3-1) were as follows.

$^1$H-NMR (400 MHz; CDCl$_3$); 7.09-7.14 (m, 1H), 7.27-7.37 (m, 3H), 7.37-7.41 (m, 1H), 7.41-7.44 (m, 1H), 7.63-7.70 (m, 1H)

(Step (3-B): Synthesis of Compound (3-2))

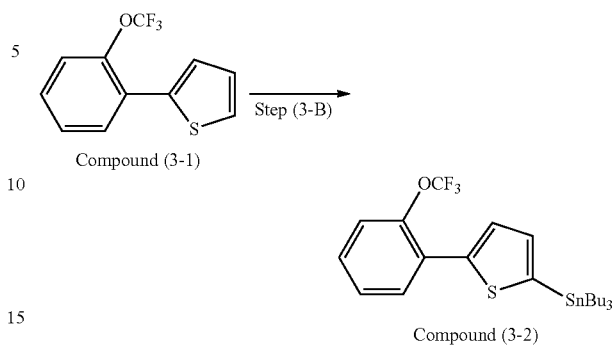

Compound (3-2)

Into a 100-ml glass reaction vessel equipped with a stirring apparatus were placed 6.35 g (26 mmol) of Compound (3-1), and 60 ml of anhydrous tetrahydrofuran. While the internal temperature was kept at −60° C. or lower, 21 ml (34 mmol) of 1.6 N solution of n-butyl lithium in hexane was added to the mixture. The mixture was stirred at the same temperature for 30 minutes, and then 11.5 g (34 mmol) of tributyl tin chloride was added to the mixture at the same temperature. The temperature of the mixture was increased to room temperature, and the mixture was stirred for 1 hour. And then, a THF-water mixture solution was added to the reaction solution for quenching, and the solvent was distilled off. Subsequently, hexane was added to the concentrate, and the mixture was filtered through [silica gel:potassium carbonate=90:10 (wt %)]. The filtrate was concentrated, and the concentrate was purified by reverse phase silica gel column chromatography (acetonitrile:water=60:40 to 95:5 vol %), to provide 13.7 g of Compound (3-2) in the form of a pale yellow liquid.

The properties of Compound (3-2) were as follows.

$^1$H-NMR (400 MHz; CDCl$_3$); 0.86-0.94 (m, 9H), 1.02-1.24 (m, 6H), 1.26-1.42 (m, 6H), 1.48-1.72 (m, 6H), 7.12-7.22 (m, 1H), 7.24-7.36 (m, 3H), 7.52-7.57 (m, 1H), 7.66-7.73 (m, 1H)

TOF-HRMS (ASAP+); 477 (M-C4H9)

(Step (3-C): Synthesis of BBT-(3))

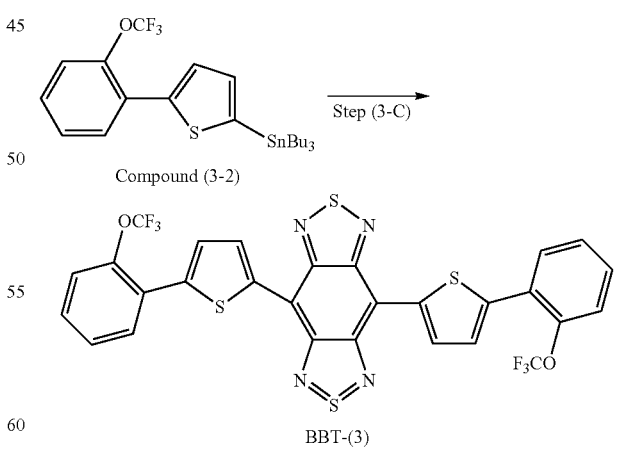

BBT-(3)

Into a 100-ml glass reaction vessel equipped with a stirring apparatus were placed 9.1 g (17 mmol) of Compound (3-2), 1.5 g (4.26 mmol) of dibromobenzobisthiadiazole (hereinafter, referred to as "Dibromo form"), 0.90 g (1.3 mmol) of dichlorobis(triphenylphosphine)palladium(II), and 50 ml of toluene. The mixture was reacted at an internal temperature of about 100° C. for 6 hours. Subsequently, the reaction solution was filtered, to provide 2.3 g of a crude product. A portion of the crude product was purified, to provide 0.15 g of BBT-(3) in the form of a dark green solid.

The properties of BBT-(3) were as follows.

$^1$H-NMR (400 MHz; deuterated dichlorobenzene: 140° C.); 7.14-7.24 (m, 4H, overlapping with the signal of deuterated dichlorobenzene), 7.25-7.33 (m, 2H), 7.57-7.64 (m, 2H), 7.71-7.79 (m, 2H), 8.99-9.05 (m, 2H)

TOF-HRMS (ASAP+); 678.9822 (M+1); Calcd. 678.9826

Example 1-4

Synthesis of Compound BBT-(4)

(Step (4-A): Synthesis of Compound (4-1))

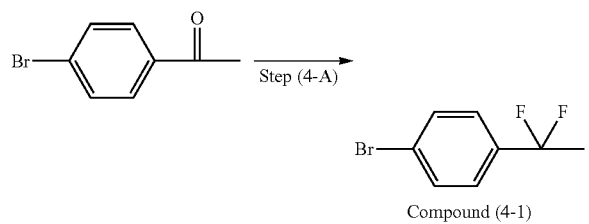

Under argon atmosphere, into a 500-ml reaction vessel made of tetrafluoroethylene-perfluoroalkyl vinyl ether copolymer (PFA) and equipped with a stirring apparatus were placed 25 g (126 mmol) of 4-bromoacetophenone, 111 g (500 mmol) of bis(2-methoxyethyl)aminosulfur trifluoride, and 250 ml of anhydrous chloroform, so that a homogeneous solution was prepared. And then, the solution was reacted at an internal temperature of about 50° C. for 35 hours. Subsequently, the reaction solution was cooled to room temperature, and then the reaction solution was added to 1000 ml of a saturated aqueous solution of sodium hydrogen carbonate, which was cooled in ice. Subsequently, the mixture was subjected to extraction with 500 ml of chloroform. The solvent was distilled off under a reduced pressure, and then the reaction mixture was purified by silica gel column chromatography (hexane: 100 vol %), to provide 17.26 g of Compound (4-1) in the form of a colorless liquid.

The properties of Compound (4-1) were as follows.

$^1$H-NMR (400 MHz, CDCl$_3$, δ (ppm)); 1.90 (3H, t, J=18.1 Hz), 7.54 (2H, d, J=2.3 Hz), 7.57 (2H, d, J=2.4 Hz)

CI-MS; 222 (M+2)

(Step (4-B): Synthesis of Compound (4-2))

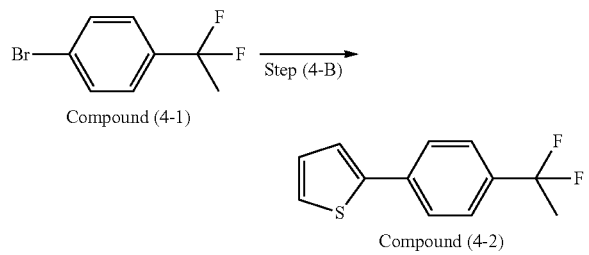

Into a 1000-ml glass reaction vessel equipped with a stirring apparatus were placed 14.85 g (67.2 mmol) of Compound (4-1), 14.09 g (20.2 mmol) of dichlorobis(triphenylphosphine)palladium(II), 32.6 g (87.4 mmol) of 2-(tributyltin)thiophene, and 450 ml of toluene. The mixture was reacted at an internal temperature of about 100° C. for 2 hours. After the completion of the reaction, the reaction solution was filtered with Celite, and then the solvent was concentrated. And then, inorganic substances were removed by filtration, and the filtrate was concentrated. The concentrate was purified by silica gel column chromatography (normal phase silica gel:potassium carbonate=90:10 (weight ratio), hexane: 100 vol %). Subsequently, the resultant material was purified again by normal phase silica gel column chromatography (hexane: 100 vol %), to provide 9.8 g of Compound (4-2) in the form of a white solid.

The properties of Compound (4-2) were as follows.

$^1$H-NMR (400 MHz, CDCl$_3$, δ (ppm)); 1.94 (3H, t, J=18.1 Hz), 7.09-7.26 (1H, m), 7.31-7.36 (2H, m), 7.51 (2H, d, J=8.6 Hz), 7.66 (2H, d, J=6.8 Hz)

EI-MS; 224 (M+)

(Step (4-C): Synthesis of Compound (4-3))

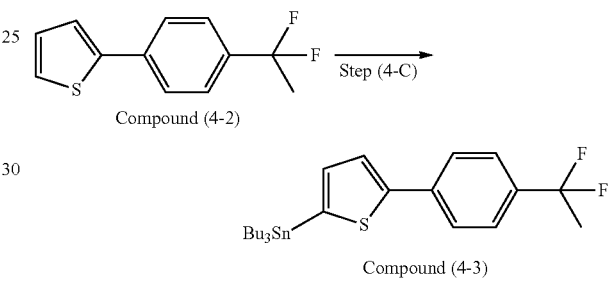

Into a 100-ml glass reaction vessel equipped with a stirring apparatus were placed 2.24 g (10.0 mmol) of Compound (4-2), and 40 ml of anhydrous tetrahydrofuran. While the internal temperature was kept at −78° C. or lower, 7.5 ml (12.0 mmol) of 1.6 N solution of n-butyl lithium in hexane was added to the mixture. The mixture was stirred at the same temperature for 1 hour, and then 3.3 ml (12.2 mmol) of tributyl tin chloride was added to the mixture at the same temperature. While the temperature of the mixture was increased to room temperature, the mixture was stirred overnight. And then, methanol was added to the reaction solution for quenching, and then the solvent was distilled off. The crude product obtained was stirred together with hexane-normal phase silica gel/potassium carbonate (90/10, weight ratio) for 10 minutes, and then filtered and concentrated, to provide 5.46 g of Crude product A in the form of a yellow liquid. A scale-up experiment of the reaction was carried out in which the same operations were performed, to provide 18.59 g of Crude product B. Crude product A and Crude product B were combined, and then the mixture was purified by C1 reverse phase silica gel column chromatography (acetonitrile:water=90:10 to 100:0 vol %), to provide 22.35 g of Compound (4-3) in the form of a yellow oil.

The properties of Compound (4-3) were as follows.

$^1$H-NMR (400 MHz, CDCl$_3$, δ (ppm)); 0.91 (9H, t, J=7.4 Hz), 1.05-1.22 (6H, m), 1.25-1.40 (6H, m), 1.42-1.68 (6H, m), 1.94 (3H, t, J=18.1 Hz), 7.12-7.18 (1H, m), 7.45-7.52 (3H, m), 7.66 (2H, d, J=8.6 Hz),

EI-MS; 514 (M+)

(Step (4-D): Synthesis of BBT-(4))

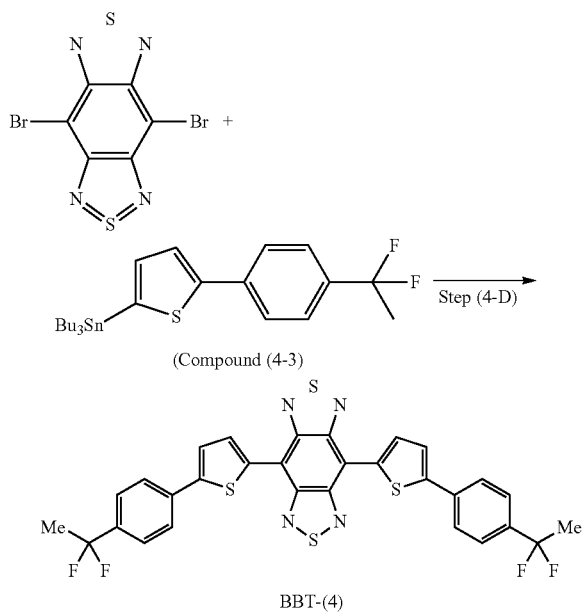

(Compound (4-3))

BBT-(4)

Into a 200-ml glass reaction vessel equipped with a stirring apparatus were placed 6.2 g (12 mmol) of Compound (4-3), 1.06 g (3 mmol) of dibromobenzobisthiadiazole (hereinafter, referred to as "Dibromo form"), 0.63 g (0.9 mmol) of dichlorobis(triphenylphosphine)palladium(II), and 50 ml of toluene. The mixture was reacted at an internal temperature of about 100° C. for 6 hours. Subsequently, the reaction solution was filtered, to provide 1.88 g of a crude product. The crude product was purified, to provide 0.33 g of Compound BBT-(4) in the form of a dark greenish blue solid.

The properties of BBT-(4) were as follows.

$^1$H-NMR (400 MHz; deuterated dichlorobenzene; 140° C.; δ (ppm)); 1.83-1.92 (6H, m), 7.50 (6H, brs), 7.74 (4H, brs), 9.04 (2H, brs)

TOF-MS (ASAP+); 639 (M+1)

Example 1-5

Synthesis of Compound BBT-(5)

(Step (5-A): Synthesis of Compound (5-1))

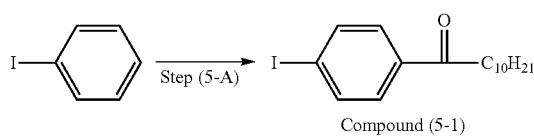

Compound (5-1)

Under nitrogen atmosphere, into a 200-ml glass reaction vessel equipped with a thermometer and a stirring apparatus were placed 40 g (255 mmol) of aluminum chloride, and 90 ml of carbon disulfide. While the internal temperature was kept at −5° C. to 5° C., under stirring, 45 g (221 mmol) of 4-iodobenzene, and then 59 g (290 mmol) of undecanoyl chloride were slowly added dropwise to the mixture. While the temperature of the mixture was increased to room temperature, the mixture was reacted overnight. After the completion of the reaction, the reaction solution obtained was added to 200 ml of 1 N hydrochloric acid, which was cooled in ice. Subsequently, the mixture was subjected to extraction with 1000 ml of ethyl acetate, and the organic layer was washed with water, and then with a solution of salt. The organic layer was dried over anhydrous magnesium sulfate, and then the solvent was distilled off under a reduced pressure. The reaction mixture obtained was purified by reverse phase silica gel column chromatography (water:acetonitrile=40:60 to 5:95 vol %), to provide 22.4 g of Compound (5-1) in the form of a white solid (Isolated yield: 27%).

The properties of Compound (5-1) were as follows.

$^1$H-NMR (400 MHz; CDCl$_3$); 0.86-0.90 (3H, m), 1.26-1.75 (16H, m), 2.89-2.93 (2H, m), 7.64-7.68 (2H, m), 7.80-7.84 (2H, m)

CI-MS; 373 (M+1)

(Step (5-B): Synthesis of Compound (5-2))

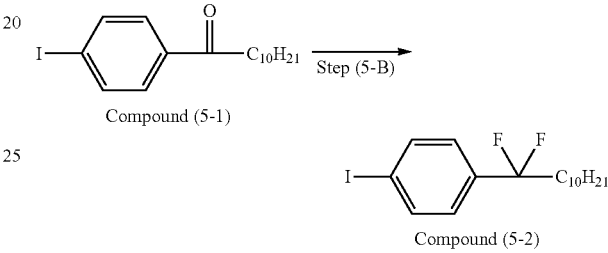

Compound (5-1)

Compound (5-2)

Under argon atmosphere, into a 200-ml reaction vessel made of tetrafluoroethylene-perfluoroalkyl vinyl ether copolymer (PFA) and equipped with a stirring apparatus were placed 14.7 g (39.5 mmol) of Compound (5-1), 34.8 g (158 mmol) of bis(2-methoxyethyl)aminosulfur trifluoride, and 147 ml of anhydrous chloroform, so that a homogeneous solution was prepared. The solution was reacted at an internal temperature of about 50° C. for 35 hours. The reaction solution was cooled to room temperature, and then the reaction solution was added to 500 ml of a saturated aqueous solution of sodium hydrogen carbonate, which was cooled in ice, for quenching. The mixture solution was subjected to extraction with 500 ml of chloroform. The organic layer was dried over anhydrous magnesium sulfate, and then the solvent was distilled off under a reduced pressure. The reaction mixture obtained was purified by silica gel column chromatography (hexane: 100 vol %), to provide 7.1 g of Compound (5-2) in the form of a colorless liquid (Isolated yield: 46%).

The properties of Compound (5-2) were as follows.

$^1$H-NMR (400 MHz; CDCl$_3$); 0.86-0.89 (3H, m), 1.24-1.46 (16H, m), 2.01-2.13 (2H, m), 7.18-7.20 (2H, m), 7.74-7.77 (2H, m)

EI-MS; 394 (M+)

(Step (5-C): Synthesis of Compound (5-3))

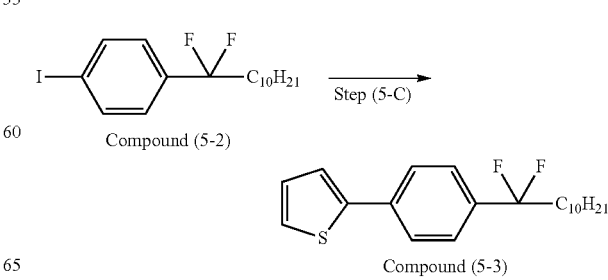

Compound (5-2)

Compound (5-3)

Into a 500-ml glass reaction vessel equipped with a stirring apparatus were placed 8.5 g (21.6 mmol) of Compound (5-2), 3.0 g (4.32 mmol) of dichlorobis(triphenylphosphine)palladium(II), 16.1 g (43.2 mmol) of 2-(tributyltin)thiophene, and 256 ml of toluene. The mixture was reacted at an internal temperature of about 100° C. for 6 hours. After the completion of the reaction, the solvent was concentrated, and then the concentrate was purified by reverse phase silica gel column chromatography (acetonitrile:water=60:40 to 90:10 vol %), and then by silica gel column chromatography (hexane: 100%), to provide 5.9 g of Compound (5-3) in the form of a white solid (Isolated yield: 78%).

The properties of Compound (5-3) were as follows.
$^1$H-NMR (400 MHz; CDCl$_3$); 0.85-0.91 (3H, m), 1.24-1.44 (16H, m), 2.06-2.18 (2H, m), 7.08-7.10 (1H, m), 7.30-7.35 (2H, m), 7.45-7.47 (2H, m), 7.63-7.65 (2H, m)
EI-MS; 350 (M+);

(Step (5-D): Synthesis of Compound (5-4))

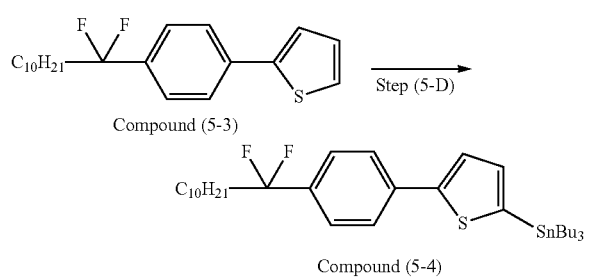

Compound (5-3)

Compound (5-4)

Into a 100-ml glass reaction vessel equipped with a stirring apparatus were placed 4.00 g (11.4 mmol) of Compound (5-3), and 40 ml of anhydrous tetrahydrofuran. While the internal temperature was kept at −55° C. or lower, 9.3 ml (14.8 mmol) of 1.6 N solution of n-butyl lithium in hexane was added to the mixture. The mixture was stirred at the same temperature for 30 minutes, and then 5.0 g (14.8 mmol) of tributyl tin chloride was added to the mixture at the same temperature. The temperature of the mixture was increased to room temperature, and the mixture was stirred overnight. And then, a THF-water mixture solution was added to the reaction solution for quenching, and the solvent was distilled off. Subsequently, hexane was added to the concentrate, and the mixture was filtered. The filtrate was concentrated, and the concentrate was purified by reverse phase silica gel column chromatography (acetonitrile:water=70:30 to 100:0 vol %), to provide 6.1 g of Compound (5-4) in the form of a pale yellow liquid.

The properties of Compound (5-4) were as follows.
$^1$H-NMR (400 MHz; CDCl$_3$); 0.84-0.94 (m, 12H), 1.02-1.21 (m, 6H), 1.21-1.72 (m, 28H), 2.02-2.22 (m, 2H), 7.11-7.19 (m, 1H), 7.40-7.50 (m, 3H), 7.62-7.69 (m, 2H)

(Step (5-E): Synthesis of BBT-(5))

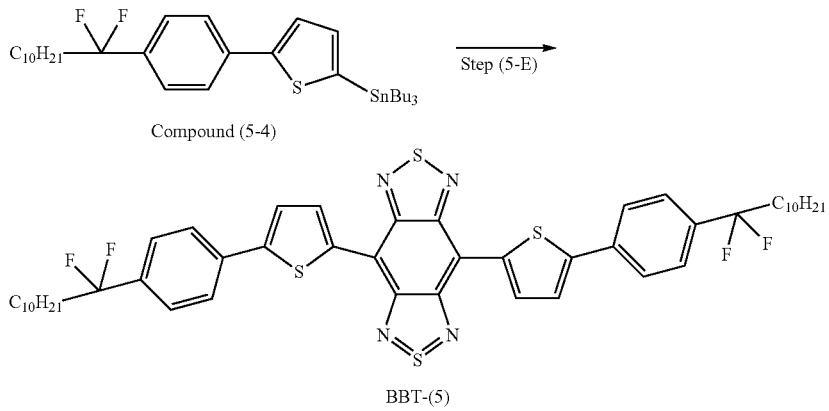

Compound (5-4)

BBT-(5)

Into a 100-ml glass reaction vessel equipped with a stirring apparatus were placed 5.8 g (9.1 mmol) of Compound (5-4), 0.8 g (2.27 mmol) of dibromobenzobisthiadiazole, 0.48 g (0.68 mmol) of dichlorobis(triphenylphosphine)palladium (II), and 50 ml of toluene. The mixture was reacted at an internal temperature of about 100° C. for 7 hours. The reaction solution was filtered, to provide 1.76 g of a crude product. The crude product was purified, to provide 1.32 g of BBT-(5) in the form of a dark green solid.

The properties of BBT-(5) were as follows.
$^1$H-NMR (400 MHz; deuterated dichlorobenzene: 140° C.); 0.78-0.90 (m, 6H), 1.18-1.40 (m, 28H), 1.46-1.60 (m, 4H), 2.05-2.30 (m, 4H), 7.44-7.58 (m, 6H), 7.70-7.84 (m, 4H), 9.00-9.07 (m, 2H)
TOF-HRMS (ASAP+); 891.3223 (M+1); Calcd. 891.3246

Example 1-6

Synthesis of Compound BBT-(6)

(Step (6-A): Synthesis of Compound (6-1))

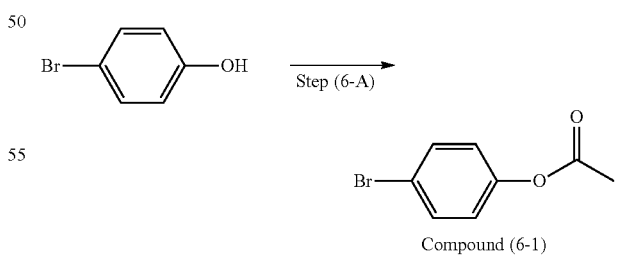

Compound (6-1)

Under argon atmosphere, into a 2000-ml glass reaction vessel equipped with a stirring apparatus were placed 173.0 g (1.0 mol) of 4-bromophenol, 208 ml (1.5 mol) of triethylamine, (one spatula of) 4-dimethylaminopyridine, and 500 ml of anhydrous chloroform, so that a homogeneous solution was prepared. And then, the solution was cooled to an internal temperature of about 0° C. to 10° C. Meanwhile, 86 ml (1.2 mol) of acetyl chloride was diluted with 1000 ml of anhydrous chloroform, and the prepared solution was slowly added dropwise to the solution from a dropping funnel. While the temperature of the mixture solution was increased to room temperature, the solution was stirred and reacted overnight. And then, the reaction solution was added to 500 ml of water for quenching, and the organic layer was washed with 500 ml of water twice, and then washed with 500 ml of 1 N hydrochloric acid three times. The organic layer was dried over anhydrous magnesium sulfate, and then the solvent was distilled off under a reduced pressure. The reaction mixture obtained was purified by silica gel column chromatography (hexane:ethyl acetate=95:5 vol %), to provide 172.1 g of Compound (6-1) in the form of a yellow liquid.

The properties of Compound (6-1) were as follows.

$^1$H-NMR (400 MHz, CDCl$_3$, δ (ppm)); 2.30 (3H, s), 6.96-7.01 (2H, m), 7.46-7.52 (2H, m)

EI-MS; 216 (M+2)

(Step (6-B): Synthesis of Compound (6-2))

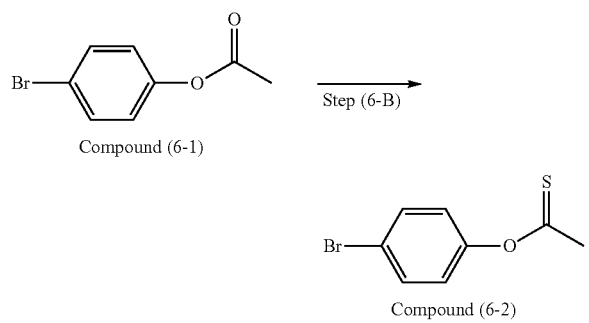

Compound (6-1)

Step (6-B)

Compound (6-2)

Under nitrogen atmosphere, into a 300-ml glass reaction vessel equipped with a thermometer and a stirring apparatus were placed 50 g (233 mmol) of Compound (6-1), 105 g (233 mmol) of Lawesson's reagent, and 50 ml of mesitylene. While the internal temperature was kept at about 165° C., under stirring, the mixture was reacted for 1 hour, and then 200 ml of toluene was added to the reaction solution. The same reaction was carried out twice, and the reaction solutions from the three sets of reactions were combined. The combined reaction solution was filtered, and the filtrate was concentrated. The crude product obtained was purified with a silica gel column (hexane: 100 vol %) twice, to provide 15.3 g of Compound (6-2) in the form of a red solid (Isolated yield: 10%).

The properties of Compound (6-2) were as follows.

$^1$H-NMR (400 MHz; CDCl$_3$); 2.80 (3H, s), 6.89-6.93 (2H, m), 7.51-7.57 (2H, m)

CI-MS; 233 (M+2);

(Step (6-C): Synthesis of Compound (6-3))

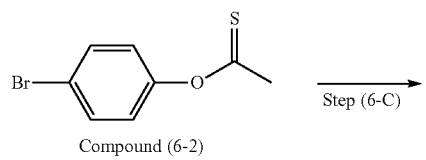

Compound (6-2)

Step (6-C)

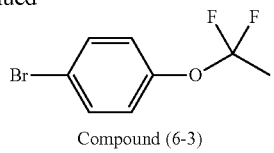

Compound (6-3)

Under argon atmosphere, into a 200-ml reaction vessel made of tetrafluoroethylene-perfluoroalkyl vinyl ether copolymer (PFA) and equipped with a stirring apparatus were placed 6.11 g (26.4 mmol) of Compound (6-2), 0.6 g (2.6 mmol) of antimony trichloride, and 80 ml of anhydrous methylene chloride, so that a solution was prepared. Subsequently, a homogeneous solution prepared by the addition of 23.4 g (105.8 mmol) of bis(2-methoxyethyl)aminosulfur trifluoride and 40 ml of anhydrous methylene chloride was added dropwise to the solution in a water bath, and the mixture was stirred overnight. After the completion of the reaction, the reaction solution was added to 500 ml of a saturated aqueous solution of sodium hydrogen carbonate, which was cooled in ice. Subsequently, the mixture was subjected to extraction with 500 ml of methylene chloride. The organic layer was dried over anhydrous magnesium sulfate, and then the solvent was distilled off under a reduced pressure, to provide a crude reaction product. This crude reaction product was mixed with a crude reaction product, which was obtained by performing the same operations using 7.8 g (33.8 mmol) of Compound (6-2), and then the mixture was purified by silica gel column chromatography (hexane: 100 vol %), to provide 4.22 g of Compound (6-3) in the form of a light yellow liquid (Isolated yield: 30%).

The properties of Compound (6-3) were as follows.

$^1$H-NMR (400 MHz; CDCl$_3$); 1.88-1.94 (3H, m), 7.04-7.13 (2H, m), 7.43-7.48 (2H, m)

CI-MS; 238 (M+1)

(Step (6-D): Synthesis of Compound (6-4))

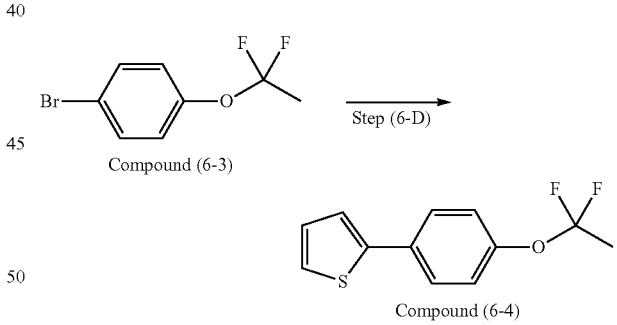

Compound (6-3)

Step (6-D)

Compound (6-4)

Into a 200-ml glass reaction vessel equipped with a stirring apparatus were placed 4.2 g (17.8 mmol) of Compound (6-3), 3.1 g (4.45 mmol) of dichlorobis(triphenylphosphine)palladium(II), 8.64 g (23.1 mmol) of 2-(tributyltin)thiophene, and 120 ml of toluene. The mixture was reacted at an internal temperature of about 100° C. for 6 hours. After the completion of the reaction, 100 ml of hexane was added to the reaction solution, and then the mixture was filtered and the filtrate was concentrated, to provide a crude product. Subsequently, the crude product obtained was purified by silica gel column chromatography (hexane: 100%), and then by silica gel column chromatography with 10 wt % of potassium carbonate mixed (hexane: 100 vol %), to provide 1.9 g of Compound (6-4) in the form of a white solid (Isolated yield: 44%).

The properties of Compound (6-4) were as follows.
$^1$H-NMR (400 MHz; CDCl$_3$); 1.90-1.96 (3H, m), 7.06-7.08 (1H, m), 7.17-7.20 (2H, m), 7.25-7.27 (2H, m), 7.55-7.58 (2H, m)
CI-MS; 241 (M+1)
(Step (6-E): Synthesis of Compound (6-5))

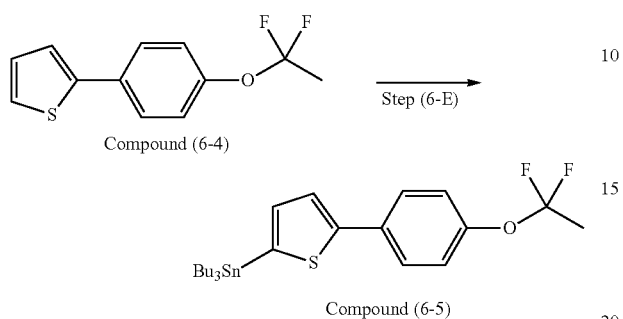

Compound (6-4)

Compound (6-5)

Into a 200-ml glass reaction vessel equipped with a stirring apparatus were placed 1.9 g (7.91 mmol) of Compound (6-4), and 40 ml of anhydrous tetrahydrofuran. While the internal temperature was kept at −55° C. or lower, 6.0 ml (9.48 mmol) of 1.58 N solution of n-butyl lithium in hexane was added to the mixture. The mixture was stirred at the same temperature for 1 hour, and then 3.08 g (9.48 mmol) of tributyl tin chloride was added to the mixture at the same temperature. The temperature of the mixture was increased to room temperature, and the mixture was stirred overnight. And then, methanol was added to the reaction solution for quenching, and then the solvent was distilled off. The crude product obtained was purified by reverse phase silica gel column chromatography (acetonitrile:water=80:20 to 85:15 vol %), to provide 3.52 g of Compound (6-5) in the form of a yellow oil (Isolated yield: 84%).

The properties of Compound (6-5) were as follows.
$^1$H-NMR (400 MHz; CDCl$_3$); 0.89-0.92 (9H, m), 1.06-1.21 (6H, m), 1.31-1.40 (6H, m), 1.53-1.63 (6H, m), 1.89-1.96 (3H, m), 7.12-7.18 (3H, m), 7.37-7.38 (1H, m), 7.56-7.59 (2H, m)
CI-MS; 530 (M+1);
(Step (6-F): Synthesis of Compound BBT-(6))

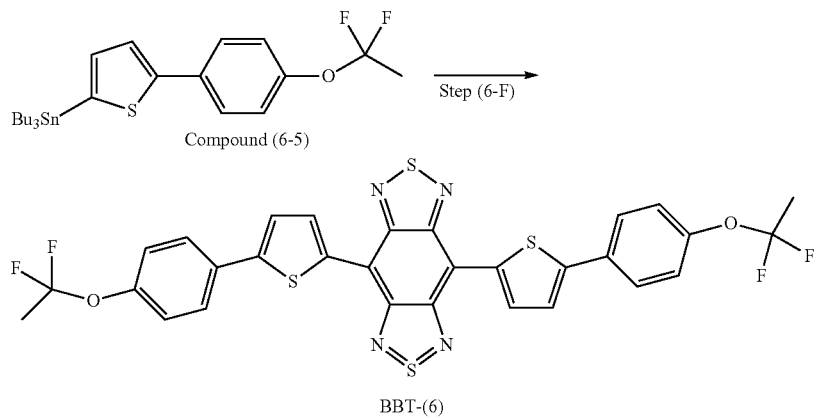

BBT-(6)

Into a 20-ml glass reaction vessel equipped with a stirring apparatus were placed 3.52 g (6.65 mmol) of Compound (6-5), 0.62 g (1.66 mmol) of dibromobenzobisthiadiazole, 0.35 g (0.50 mmol) of dichlorobis(triphenylphosphine)palladium(II), and 20 ml of toluene. The mixture was reacted at an internal temperature of about 100° C. for 6 hours. The reaction solution was filtered, to provide 0.5 g of a crude product. The crude product was purified, to provide 0.45 g of BBT-(6) in the form of a dark greenish blue solid (Isolated yield: 34%).

The properties of BBT-(6) were as follows.
$^1$H-NMR (400 MHz; deuterated dichlorobenzene: 140° C.); 1.80-1.87 (6H, m), 7.17-7.20 (4H, m), 7.40-7.41 (2H, m), 7.66-7.68 (4H, m), 9.00-9.01 (2H, m)
TOF-HRMS (ASAP+); 671.0320 (M+1); Calcd. 671.0327.

Example 1-7

Synthesis of Compound BBT-(7)

(Step (7-A): Synthesis of Compound (7-1))

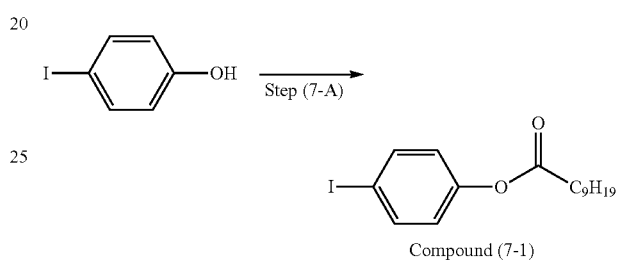

Compound (7-1)

Under nitrogen atmosphere, into a 2000-ml glass reaction vessel equipped with a thermometer and a stirring apparatus were placed 125 g (568 mmol) of 4-iodophenol, and 250 ml of chloroform, so that a homogeneous solution was prepared. Subsequently, 86.2 g (852 mmol) of triethylamine was added dropwise to the homogeneous solution, and then a solution prepared by dissolving 130 g (681 mmol) of decanoyl chloride in 1000 ml of chloroform was added dropwise to the solution at an internal temperature of 10° C. or lower, and the mixture was stirred overnight. The reaction solution was washed with 500 ml of water three times, and washed with 500 ml of 1 N hydrochloric acid three times, and then dried over anhydrous magnesium sulfate. The solution was concentrated, and then the crude product obtained was purified with a silica gel column (hexane:ethyl acetate=95:5 vol %), to provide 217 g of Compound (7-1) in the form of a colorless oil (Isolated yield: 100%).

The properties of Compound (7-1) were as follows.

¹H-NMR (400 MHz; CDCl₃); 0.86-0.90 (3H, m), 1.23-1.46 (12H, m), 1.69-1.77 (2H, m), 2.51-2.55 (2H, m), 6.82-6.86 (2H, m), 7.65-7.68 (2H, m)

EI-MS; 374 (M+);

(Step (7-B): Synthesis of Compound (7-2))

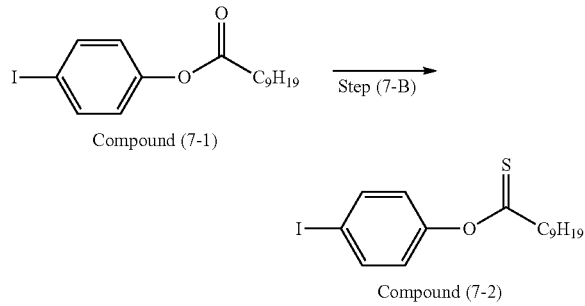

Compound (7-1)

Compound (7-2)

Into a 100-ml glass reaction vessel equipped with a stirring apparatus were placed 10 g (26.7 mmol) of Compound (7-1), and 9.6 g (21.4 mmol) of Lawesson's reagent. While the internal temperature was kept at about 165° C., under stirring, the mixture was reacted for 30 minutes. The reaction solution was cooled to about 100° C., and then 100 ml of toluene was added to the solution, to provide a suspension. The same reaction was carried out twice, and the suspensions obtained were combined, to provide Reaction solution A. And then, into a 200-ml glass reaction vessel equipped with a stirring apparatus were placed 20 g (53.4 mmol) of Compound (7-1), and 19.2 g (42.7 mmol) of Lawesson's reagent. While the internal temperature was kept at about 165° C., under stirring, the mixture was reacted for 40 minutes. The reaction solution was cooled to about 100° C., and then 100 ml of toluene was added to the solution, to provide a suspension. The same reaction was carried out twice, and the suspensions obtained were combined, to provide Reaction solution B. And then, into a 200-ml glass reaction vessel equipped with a stirring apparatus were placed 30 g (80.1 mmol) of Compound (7-1), and 28.8 g (64.1 mmol) of Lawesson's reagent. While the internal temperature was kept at about 165° C., under stirring, the mixture was reacted for 45 minutes. The reaction solution was cooled to about 100° C., and then 100 ml of toluene was added to the solution, to provide a suspension. The same reaction was carried out twice, and the suspensions obtained were combined, to provide Reaction solution C. The Reaction solutions A, B and C were combined, and then solids were removed by filtration, and the filtrate was concentrated. The crude product obtained was purified with a silica gel column (hexane: 100 vol %) twice, to provide 87 g of red oil containing Compound (7-2).

The properties of Compound (7-2) were as follows.

CI-MS; 391 (M+1);

(Step (7-C): Synthesis of Compound (7-3))

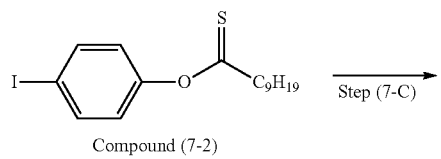

Compound (7-2)

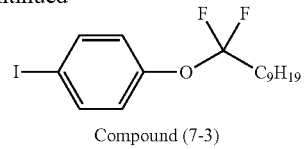

Compound (7-3)

Under argon atmosphere, into a 500-ml reaction vessel made of tetrafluoroethylene-perfluoroalkyl vinyl ether copolymer (PFA) and equipped with a stirring apparatus were placed 87 g of the red liquid containing Compound (7-2) obtained in Step (7-B), 5.09 g (22.3 mmol) of antimony trichloride, and 400 ml of anhydrous chloroform, so that a solution was prepared. Subsequently, 147.6 g (667 mmol) of bis(2-methoxyethyl)aminosulfur trifluoride was added dropwise to the solution in a water bath, and the mixture was stirred overnight. After the completion of the reaction, the reaction solution was added to 1000 ml of a saturated aqueous solution of sodium hydrogen carbonate, which was cooled in ice. Subsequently, the mixture was subjected to extraction with 500 ml of chloroform. The organic layer was dried over anhydrous magnesium sulfate, and then the solvent was distilled off under a reduced pressure, to provide a crude reaction product. The crude reaction products were combined, and purified by silica gel column chromatography (hexane: 100 vol %) twice, and then by reverse phase silica gel column chromatography (acetonitrile:water=60:40 to 90:10 vol %), to provide 7.25 g of Compound (7-3) in the form of a light yellow liquid (Isolated yield based on Compound (7-1): 4%).

The properties of Compound (7-3) were as follows.

¹H-NMR (400 MHz; CDCl₃); 0.87-0.90 (3H, m), 1.28-1.39 (12H, m), 1.57-1.65 (2H, m), 2.06-2.16 (2H, m), 6.92-6.95 (2H, m), 7.61-7.65 (2H, m)

EI-MS; 396 (M+);

(Step (7-D): Synthesis of Compound (7-4))

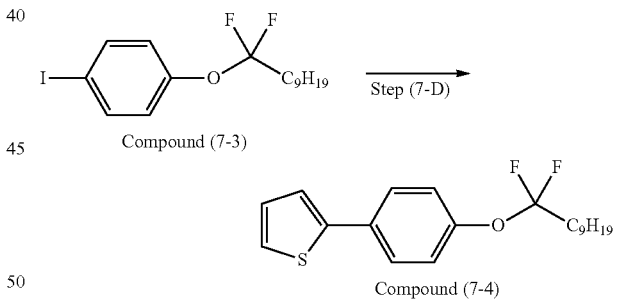

Compound (7-3)

Compound (7-4)

Into a 300-ml glass reaction vessel equipped with a stirring apparatus were placed 7.2 g (18.2 mmol) of Compound (7-3), 2.94 g (3.55 mmol) of dichlorobis(triphenylphosphine)palladium(II), 10.18 g (27.3 mmol) of 2-(tributyltin)thiophene, and 220 ml of toluene. The mixture was reacted at an internal temperature of about 100° C. for 6 hours. And then, 2.36 g (6.3 mmol) of 2-(tributyltin)thiophene was added to the reaction solution, and the mixture was reacted at an internal temperature of 110° C. for 2 hours. After the completion of the reaction, the solvent was concentrated, and then the crude product obtained was purified by silica gel column chromatography (hexane: 100 vol %), and then by reverse phase silica gel column chromatography (acetonitrile:water=60:40 to 100:0 vol %), to provide 4.53 g of Compound (7-4) in the form of a white solid (Isolated yield: 71%).

The properties of Compound (7-4) were as follows.
$^1$H-NMR (400 MHz; CDCl$_3$); 0.87-0.91 (3H, m), 1.28-1.40 (12H, m), 1.60-1.68 (2H, m), 2.09-2.18 (2H, m), 7.05-7.08 (1H, m), 7.16-7.27 (3H, m), 7.54-7.58 (2H, m)
EI-MS; 352 (M+)
(Step (7-E): Synthesis of Compound (7-5))

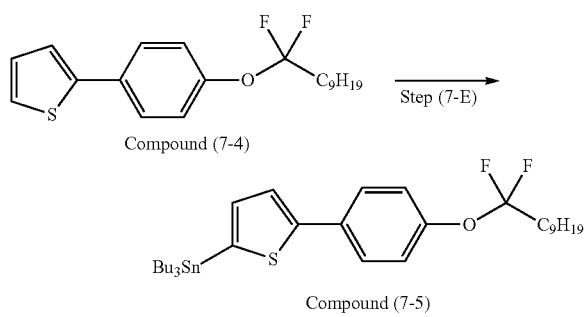

Into a 200-ml glass reaction vessel equipped with a stirring apparatus were placed 4.53 g (12.85 mmol) of Compound (7-4), and 100 ml of anhydrous tetrahydrofuran. While the internal temperature was kept at −55° C. or lower, 9.29 ml (14.77 mmol) of 1.59 N solution of n-butyl lithium in hexane was added to the mixture. The mixture was stirred at the same temperature for 1 hour, and then 4.81 g (14.77 mmol) of tributyl tin chloride was added to the mixture at the same temperature. The temperature of the mixture was increased to room temperature, and the mixture was stirred overnight. And then, methanol was added to the reaction solution, and then the solvent was distilled off. The crude product obtained was purified by reverse phase silica gel column chromatography (acetonitrile:water=60:40 to 100:0 vol %) twice, to provide 6.65 g of Compound (7-5) in the form of a yellow oil (Isolated yield: 81%).

The properties of Compound (7-5) were as follows.
$^1$H-NMR (400 MHz; CDCl$_3$); 0.89-0.92 (12H, m), 1.06-1.66 (32H, m), 2.11-2.15 (2H, m), 7.12-7.17 (3H, m), 7.37-7.38 (1H, m), 7.56-7.58 (2H, m)
CI-MS; 642 (M+1)
(Step (7-F): Synthesis of Compound BBT-(7))

Into a 20-ml glass reaction vessel equipped with a stirring apparatus were placed 2.0 g (3.12 mmol) of Compound (7-5), 0.28 g (0.78 mmol) of dibromobenzobisthiadiazole, 0.16 g (0.23 mmol) of dichlorobis(triphenylphosphine)palladium (II), and 6 ml of toluene. The mixture was reacted at an internal temperature of about 100° C. for 6 hours. The reaction solution was filtered, to provide 0.68 g of Crude product A. The same reaction was carried out using 4.49 g of Compound (7-5), to provide 1.76 g of Crude product B. The Crude product A and the Crude product B were combined, and then the mixture was purified, to provide 0.55 g of BBT-(7) in the form of a dark greenish blue solid (Isolated yield: 24%).

The properties of BBT-(7) were as follows.
$^1$H-NMR (400 MHz; deuterated dichlorobenzene: 140° C.); 0.85-0.88 (6H, m), 1.27-1.41 (28H, m), 1.64-1.72 (4H, m), 2.11-2.21 (4H, m), 7.21-7.24 (4H, m), 7.39-7.40 (2H, m), 7.67-7.69 (4H, m), 8.97-8.98 (2H, m)
TOF-HRMS (ASAP+); 895.2814 (M+1); Calcd. 895.2831.

Example 1-8

Synthesis of Compound BBT-8

(Step (8-A): Synthesis of Compound (8-1))

Under argon atmosphere, into a 500-ml glass reaction vessel equipped with a stirring apparatus were placed 11.40 g (19.8 mmol) of 1-bromo-4-(heptadecafluorooctyl)benzene, 4.17 g (5.9 mmol) of dichlorobis(triphenylphosphine)palladium(II), 9.6 g (25.8 mmol) of 2-(tributyltin)thiophene, and 340 ml of toluene. The mixture was reacted at an internal temperature of about 100° C. for 3 hours. After the completion of the reaction, the reaction solvent was concentrated, and the concentrate was purified by normal phase silica gel column chromatography (hexane: 100%), to provide a white solid. The white solid was purified with [normal phase silica gel:potassium carbonate=90:10 (weight ratio)] (hexane: 100%). Subsequently, the resultant material was purified by C18 reverse phase silica gel column chromatography (acetonitrile:water=80:20 to 100:0 vol %), to provide 8.3 g of Compound (8-1) in the form of a white solid.

The properties of Compound (8-1) were as follows.

$^1$H-NMR (400 MHz, CDCl$_3$, δ (ppm)); 7.13 (1H, dd, J=3.6 Hz, J=5.0 Hz), 7.37 (1H, d, J=5.1 Hz), 7.41 (1H, d, J=3.6 Hz), 7.59 (2H, d, J=8.5 Hz), 7.73 (2H, d, J=8.6 Hz)

EI-MS; 578 (M+)

(Step (8-B): Synthesis of Compound (8-2))

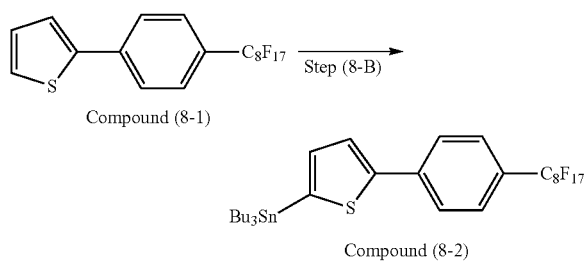

Into a 1000-ml glass reaction vessel equipped with a stirring apparatus were placed 7.42 g (12.8 mmol) of Compound (8-1), and 800 ml of anhydrous tetrahydrofuran. While the internal temperature was kept at −78° C. or lower, 8.8 ml (14.1 mmol) of 1.6 N solution of n-butyl lithium in hexane was added to the mixture. The mixture was stirred at the same temperature for 1 hour, and then 3.8 ml (14.0 mmol) of tributyl tin chloride was added to the mixture at the same temperature. While the temperature of the mixture was increased to room temperature, the mixture was stirred overnight. And then, 10 ml of methanol was added to the reaction solution for quenching, and the solvent was distilled off. The crude product obtained was stirred with chloroform-normal phase silica gel/potassium carbonate (90:10 wt %) for 10 minutes, and then the mixture was filtered and the filtrate was concentrated, to provide 11.4 g of a crude product in the form of a purple solid. The crude product was purified by C1 reverse phase silica gel column chromatography (acetonitrile:water=95:5 to 100:0 vol %, 2-propanol: 100 vol %), to provide 3.58 g of Compound (8-2) in the form of a red oil.

The properties of Compound (8-2) were as follows.

$^1$H-NMR (400 MHz, CDCl$_3$, δ (ppm)); 0.91 (9H, t, J=7.3 Hz), 1.12-1.16 (6H, m), 1.31-1.40 (6H, m), 1.55-1.64 (6H, m), 7.14-7.20 (1H, m), 7.51-7.53 (1H, m), 7.57 (2H, d, J=8.4 Hz), 7.74 (2H, d, J=8.4 Hz),

CI-MS; 867 (M+)

(Step (8-C): Synthesis of Compound BBT-8)

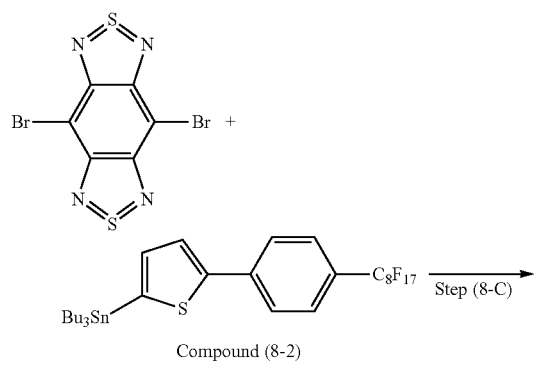

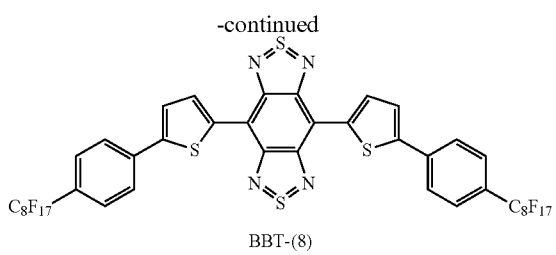

Into a 100-ml glass reaction vessel equipped with a stirring apparatus were placed 3.58 g (4.13 mmol) of Compound (8-2), 0.36 g (1.03 mmol) of dibromobenzobisthiadiazole (hereinafter, referred to as "Dibromo form"), 0.22 g (0.31 mmol) of dichlorobis(triphenylphosphine)palladium(II), and 30 ml of toluene. The mixture was reacted at an internal temperature of about 100° C. for 6 hours. The reaction solution was filtered, to provide 1.98 g of a crude product. The crude product was purified, to provide 0.51 g of Compound BBT-(8) in the form of a dark greenish blue solid.

The properties of BBT-(8) were as follows.

$^1$H-NMR (400 MHz; deuterated dichlorobenzene: 140° C.; δ (ppm)); 7.55-7.60 (6H, m), 7.81-7.83 (4H, m), 9.05 (2H, brs),

TOF-MS (ASAP+); 1346 (M+1)

Example 1-9

Synthesis of Compound BBT-(9)

(Step (9-A): Synthesis of Compound (9-1))

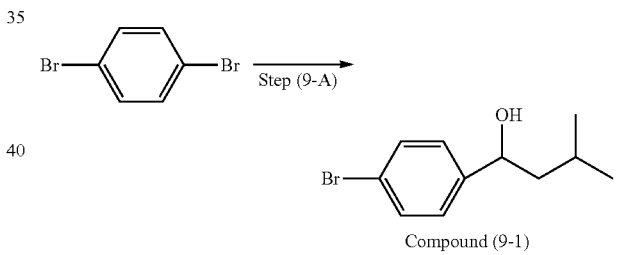

Under argon atmosphere, into a 500-ml glass reaction vessel equipped with a stirring apparatus were placed 25 g (106 mmol) of 1,4-dibromobenzene, and 300 ml of anhydrous tetrahydrofuran. While the internal temperature was kept at −78° C. or lower, 75 ml (120 mmol) of 1.6 N solution of n-butyl lithium in hexane was added to the mixture. The mixture was stirred at the same temperature for 1 hour, and then 13.8 ml (128 mmol) of isovaleraldehyde was added to the mixture at the same temperature. The temperature of the mixture was increased to room temperature, and the mixture was stirred for 3 hours. The reaction solution was added to a saturated ammonium chloride aqueous solution, which was cooled at 0° C. to 10° C., and then the mixture was subjected to liquid separation with ethyl acetate. The organic layer was washed with a saturated sodium chloride aqueous solution, and then dried over anhydrous magnesium sulfate, and then the resultant material was filtered and the filtrate was concentrated, to provide 26 g of a crude product in the form of a yellow liquid. The crude product was purified by normal phase silica gel column chromatography (hexane, hexane:ethyl acetate=30:1 to 10:1 vol %), to provide 22 g of Compound (9-1) in the form of a yellow liquid.

The properties of Compound (9-1) were as follows.
¹H-NMR (400 MHz, CDCl₃, δ (ppm)); 0.94-0.96 (6H, m), 1.43-1.52 (1H, m), 1.64-1.76 (3H, m), 4.70-4.74 (1H, m), 7.21-7.25 (2H, m), 7.45-7.48 (2H, m)
EI-MS; 244 (M+)
(Step (9-B): Synthesis of Compound (9-2))

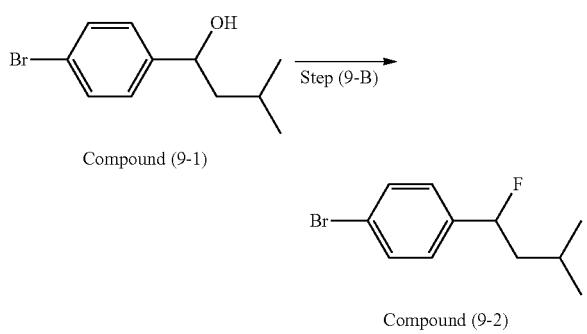

Under argon atmosphere, into a 500-ml reaction vessel made of tetrafluoroethylene-perfluoroalkyl vinyl ether copolymer (PFA) and equipped with a stirring apparatus were placed 20 g (82.3 mmol) of Compound (9-1), and 450 ml of anhydrous methylene chloride, so that a solution was prepared. Subsequently, a homogeneous solution prepared by the addition of 21.84 g (98.76 mmol) of bis(2-methoxyethyl) aminosulfur trifluoride and 50 ml of anhydrous chloroform was added dropwise to the solution in a water bath, and the mixture was stirred overnight. After the completion of the reaction, the reaction solution was added to 500 ml of a saturated aqueous solution of sodium hydrogen carbonate, which was cooled in ice. Subsequently, the mixture was subjected to extraction with 500 ml of chloroform. The organic layer was dried over anhydrous magnesium sulfate, and then the solvent was distilled off under a reduced pressure, to provide a crude reaction product. The crude reaction product was purified by silica gel column chromatography (hexane: 100 vol %), to provide 14.16 g of Compound (9-2) in the form of a colorless liquid (Isolated yield: 75%).

The properties of Compound (9-2) were as follows.
¹H-NMR (400 MHz, CDCl₃, δ (ppm)); 0.96-0.99 (6H, m), 1.47-1.61 (1H, m), 1.77-1.94 (2H, m), 5.38-5.53 (1H, m), 7.19-7.21 (2H, m), 7.48-7.50 (2H, m)
CI-MS; 246 (M+)
(Step (9-C): Synthesis of Compound (9-3))

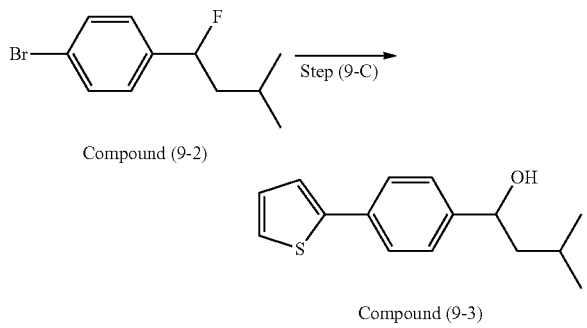

Into a 300-ml glass reaction vessel equipped with a stirring apparatus were placed 7.0 g (28.6 mmol) of Compound (9-2), 2.0 g (2.85 mmol) of dichlorobis(triphenylphosphine)palladium(II), 13.92 g (37.18 mmol) of 2-(tributyltin)thiophene, and 210 ml of toluene. The mixture was reacted at an internal temperature of about 100° C. for 2 hours. Subsequently, 100 ml of hexane was added to the reaction solution, and then the mixture was filtered, to provide Reaction solution A. The reaction was carried out in a similar manner using 7.0 g (28.6 mmol) of Compound (9-2), to provide Reaction solution B. The Reaction solutions A and B were combined, and then the mixture was concentrated under a reduced pressure. The crude product obtained was purified by silica gel column chromatography (hexane: 100 vol %), to provide 5.37 g of Compound (9-3) in the form of a white solid (Isolated yield: 39%).

The properties of Compound (9-3) were as follows.
¹H-NMR (400 MHz, CDCl₃, δ (ppm)); 0.93-0.97 (6H, m), 1.51-1.56 (1H, m), 1.69-1.79 (3H, m), 4.74-4.77 (1H, m), 7.06-7.09 (1H, m), 7.26-7.37 (4H, m), 7.58-7.61 (2H, m)
CI-MS; 246 (M+)
(Step (9-D): Synthesis of Compound (9-4))

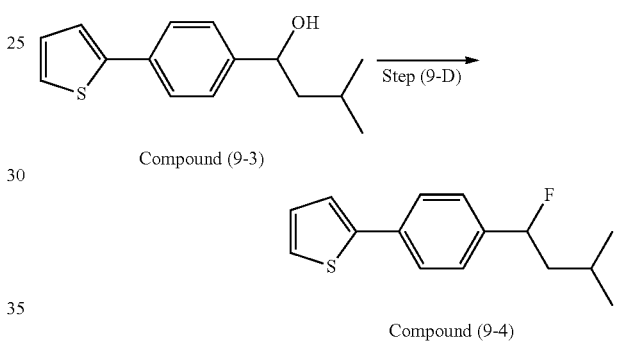

Under argon atmosphere, into a 500-ml reaction vessel made of tetrafluoroethylene-perfluoroalkyl vinyl ether copolymer (PFA) and equipped with a stirring apparatus were placed 5.76 g (26.16 mmol) of bis(2-methoxyethyl)aminosulfur trifluoride, and 170 ml of anhydrous methylene chloride, so that a solution was prepared. Subsequently, a homogeneous solution prepared by the addition of 5.37 g (21.8 mmol) of Compound (9-3) and 30 ml of anhydrous chloroform was added dropwise to the solution at −78° C. While the temperature of the mixture was increased to room temperature, the mixture was stirred overnight. After the completion of the reaction, the reaction solution was added to 500 ml of a saturated aqueous solution of sodium hydrogen carbonate, which was cooled in ice. Subsequently, the mixture was subjected to extraction with 500 ml of chloroform. The organic layer was dried over anhydrous magnesium sulfate, and then the solvent was distilled off under a reduced pressure, to provide a crude reaction product. The crude reaction product was purified by reverse phase silica gel column chromatography (acetonitrile:water=60:40 to 80:20 vol %), to provide 1.41 g of Compound (9-4) in the form of a light yellow solid (Isolated yield: 27%).

The properties of Compound (9-4) were as follows.
¹H-NMR (400 MHz, CDCl₃, δ (ppm)); 0.98-1.01 (6H, m), 1.53-1.67 (1H, m), 1.81-1.97 (2H, m), 5.43-5.58 (1H, m), 7.07-7.09 (1H, m), 7.27-7.35 (4H, m), 7.60-7.62 (2H, m)
CI-MS; 249 (M+1)

(Step (9-E): Synthesis of Compound (9-5))

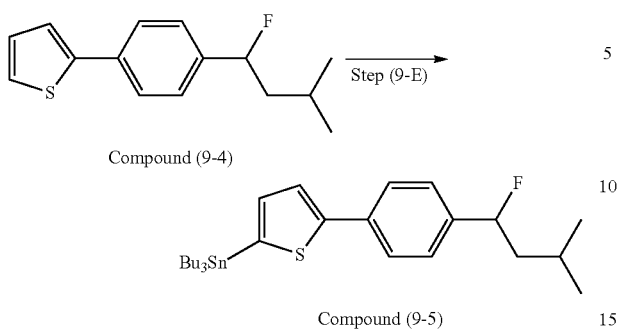

Into a 100-ml glass reaction vessel equipped with a stirring apparatus were placed 1.41 g (5.67 mmol) of Compound (9-4), and 20 ml of anhydrous tetrahydrofuran. While the internal temperature was kept at −55° C. or lower, 3.59 ml (5.67 mmol) of 1.58 N solution of n-butyl lithium in hexane was added to the mixture. The mixture was stirred at the same temperature for 1 hour, and then 2.22 g (6.8 mmol) of tributyl tin chloride was added to the mixture at the same temperature. The temperature of the mixture was increased to room temperature, and the mixture was stirred for 1 hour. Subsequently, methanol was added to the mixture, and then the solvent was distilled off. The crude product obtained was purified by reverse phase silica gel column chromatography (acetonitrile:water=60:40 to 90:10 vol %), to provide 2.77 g of Compound (9-5) in the form of a yellow oil (Isolated yield: 91%).

The properties of Compound (9-5) were as follows.
$^1$H-NMR (400 MHz, CDCl$_3$, δ (ppm)); 0.87-1.69 (34H, m), 1.78-2.01 (2H, m), 5.42-5.57 (1H, m), 7.11-7.17 (1H, m), 7.31-7.34 (2H, m), 7.42-7.43 (1H, m), 7.61-7.63 (2H, m)
EI-MS; 538 (M+1)

(Step (9-F): Synthesis of Compound BBT-(9))

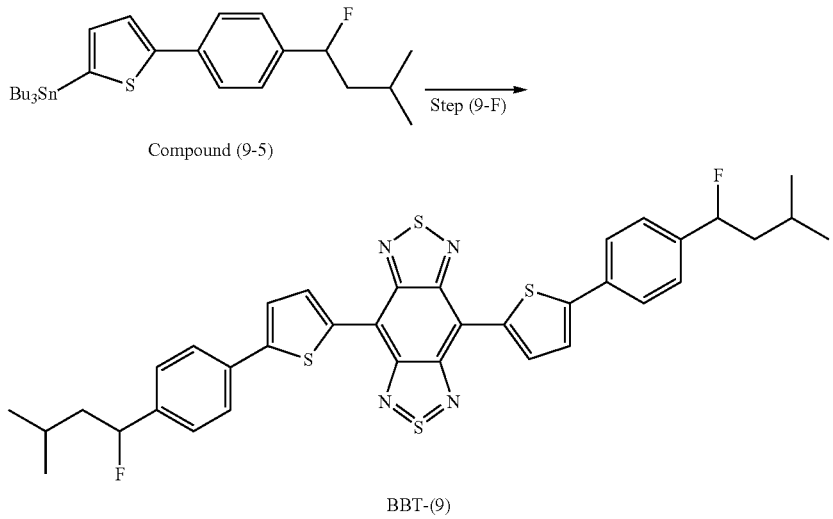

Into a 50-ml glass reaction vessel equipped with a stirring apparatus were placed 2.77 g (5.15 mmol) of Compound (9-5), 0.45 g (1.29 mmol) of dibromobenzobisthiadiazole, 0.27 g (0.39 mmol) of dichlorobis(triphenylphosphine)palladium(II), and 15 ml of toluene. The mixture was reacted at an internal temperature of about 100° C. for 6 hours. The reaction solution was filtered, and then the crude product obtained was purified, to provide 0.29 g of BBT-(9) in the form of a dark greenish blue solid (Isolated yield: 32%).

The properties of BBT-(9) were as follows.
TOF-HRMS (ASAP+); 687.1539 (M+1); Calcd. 687.1556.

Example 1-10

Synthesis of Compound BBT-(10)

(Step (10-A): Synthesis of Compound (10-1))

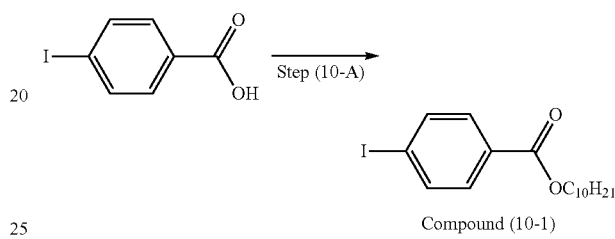

Into a 1000-ml glass reaction vessel equipped with a stirring apparatus were placed 25 g (100.8 mmol) of 4-iodobenzoic acid, 19.15 g (120.96 mmol) of n-decanol, and 500 ml of methylene chloride, so that a homogeneous solution was prepared. Subsequently, 28.9 g (150.7 mmol) of 1-ethyl-3-(3-dimethylaminopropyl)carbodiimide hydrochloride was added to the solution in a water bath in some additions. And then, 3.08 g (25.2 mmol) of 4-dimethylaminopyridine was added to the mixture, and the mixture was stirred overnight in a water bath. The reaction solution was washed with 200 ml of water twice, and then dried over anhydrous magnesium sulfate. Subsequently, the solvent was concentrated, and then the crude product obtained was purified by silica gel column chromatography (hexane:ethyl acetate=95:5 vol %), to provide 22.37 g of Compound (10-1) in the form of a colorless liquid (Isolated yield: 57%).

The properties of Compound (10-1) were as follows.
$^1$H-NMR (400 MHz; CDCl$_3$); 0.86-0.90 (3H, m), 1.36-1.46 (14H, m), 1.72-1.79 (2H, m), 4.28-4.32 (2H, m), 7.72-7.81 (4H, m)
EI-MS; 388 (M+)
(Step (10-B): Synthesis of Compound (10-2))

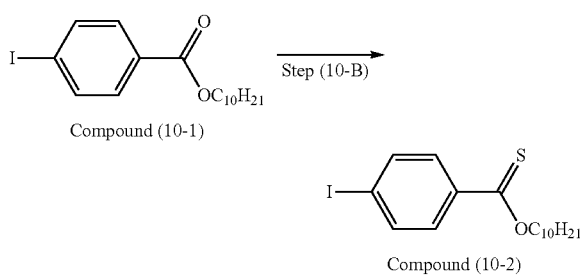

Into a 100-ml glass reaction vessel equipped with a stirring apparatus were placed 13.27 g (34.2 mmol) of Compound (10-1), and 12.29 g (27.36 mmol) of Lawesson's reagent. While the internal temperature was kept at about 190° C., under stirring, the mixture was reacted for 60 minutes. The reaction solution was cooled to about 100° C., and then 100 ml of toluene was added to the reaction solution, to provide a suspension. Solids were removed by filtration, and the filtrate was concentrated. The crude product obtained was purified with silica gel column (hexane: 100 vol %), to provide 10.03 g of Compound (10-2) in the form of a red solid (Isolated yield: 73%).

The properties of Compound (10-2) were as follows.
$^1$H-NMR (400 MHz; CDCl$_3$); 0.87-0.90 (3H, m), 1.27-1.51 (14H, m), 1.86-1.93 (2H, m), 4.61-4.65 (2H, m), 7.69-7.90 (4H, m)
CI-MS; 405 (M+1)
(Step (10-C): Synthesis of Compound (10-3))

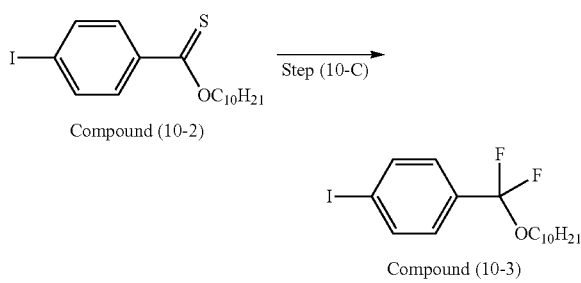

Under argon atmosphere, into a 250-ml reaction vessel made of tetrafluoroethylene-perfluoroalkyl vinyl ether copolymer (PFA) and equipped with a stirring apparatus were placed 9.0 g (22.3 mmol) of Compound (10-2), 0.51 g (2.23 mmol) of antimony trichloride, and 68 ml of anhydrous methylene chloride, so that a solution was prepared. Subsequently, a homogeneous solution prepared by the addition of 9.86 g (44.6 mmol) of bis(2-methoxyethyl)aminosulfur trifluoride and 22 ml of anhydrous methylene chloride was added dropwise to the solution in a water bath, and the mixture was stirred overnight. After the completion of the reaction, the reaction solution was added to 500 ml of a saturated aqueous solution of sodium hydrogen carbonate, which was cooled in ice, and then the mixture was subjected to extraction with 500 ml of chloroform. The organic layer was dried over anhydrous magnesium sulfate, and then the solvent was distilled off under a reduced pressure, to provide a crude reaction product. The crude reaction product was purified by reverse phase silica gel column chromatography (acetonitrile:water=60:40 to 95:5 vol %), to provide 8.0 g of Compound (10-3) in the form of a light yellow liquid (Isolated yield: 87%).

The properties of Compound (10-3) were as follows.
$^1$H-NMR (400 MHz; CDCl$_3$); 0.86-0.90 (3H, m), 1.27-1.40 (14H, m), 1.65-1.72 (2H, m), 3.99-4.02 (2H, m), 7.33-7.77 (4H, m)
EI-MS; 410 (M+)
(Step (10-D): Synthesis of Compound (10-4))

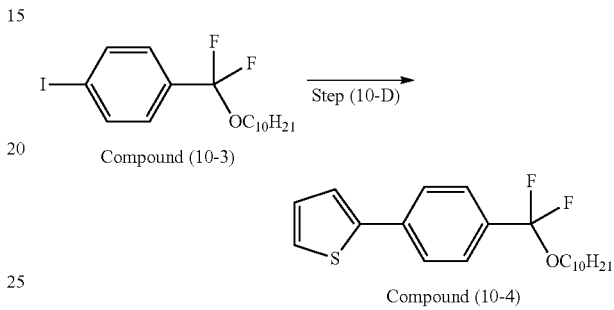

Into a 100-ml glass reaction vessel equipped with a stirring apparatus were placed 2.0 g (4.87 mmol) of Compound (10-3), 0.34 g (0.487 mmol) of dichlorobis(triphenylphosphine)palladium(II), 2.489 g (6.331 mmol) of 2-(tributyltin)thiophene, and 60 ml of toluene. The mixture was reacted at an internal temperature of about 100° C. for 6 hours. Subsequently, the solvent was concentrated under a reduced pressure, and then the crude product obtained was purified by reverse phase silica gel column chromatography (acetonitrile:water=60:40 to 90:10 vol %), to provide 1.31 g of Compound (10-4) in the form of a white solid (Isolated yield: 74%).

The properties of Compound (10-4) were as follows.
$^1$H-NMR (400 MHz; CDCl$_3$); 0.86-0.94 (3H, m), 1.27-1.44 (14H, m), 1.69-1.74 (2H, m), 4.01-4.04 (2H, m), 7.08-7.11 (1H, m), 7.31-7.36 (2H, m), 7.60-7.66 (4H, m)
EI-MS; 366 (M+)
(Step (10-E): Synthesis of Compound (10-5))

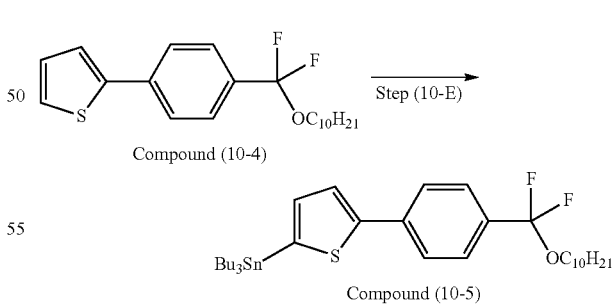

Into a 200-ml glass reaction vessel equipped with a stirring apparatus were placed 6.11 g (16.7 mmol) of Compound (10-4), and 120 ml of anhydrous tetrahydrofuran. While the internal temperature was kept at −55° C. or lower, 11.2 ml (18.4 mmol) of 1.64 N solution of n-butyl lithium in hexane was added to the mixture. The mixture was stirred at the same temperature for 1 hour, and then 5.96 g (18.4 mmol) of tributyl tin chloride was added to the mixture at the same temperature. The temperature of the mixture was increased to room temperature, and the mixture was stirred overnight. And then, methanol was added to the reaction solution, and then the solvent was distilled off. The crude product obtained was purified by reverse phase silica gel column chromatography (acetonitrile:water=60:40 to 100:0 vol %), to provide 4.88 g of Compound (10-5) in the form of a yellow oil (Isolated yield: 45%).

The properties of Compound (10-5) were as follows.

$^1$H-NMR (400 MHz; CDCl$_3$); 0.86-0.93 (12H, m), 1.11-1.73 (34H, m), 4.00-4.04 (2H, m), 7.12-7.19 (1H, m), 7.45-7.47 (1H, m), 7.58-7.67 (4H, m)

EI-MS; 656 (M+1)

(Step (10-F): Synthesis of Compound BBT-(10))

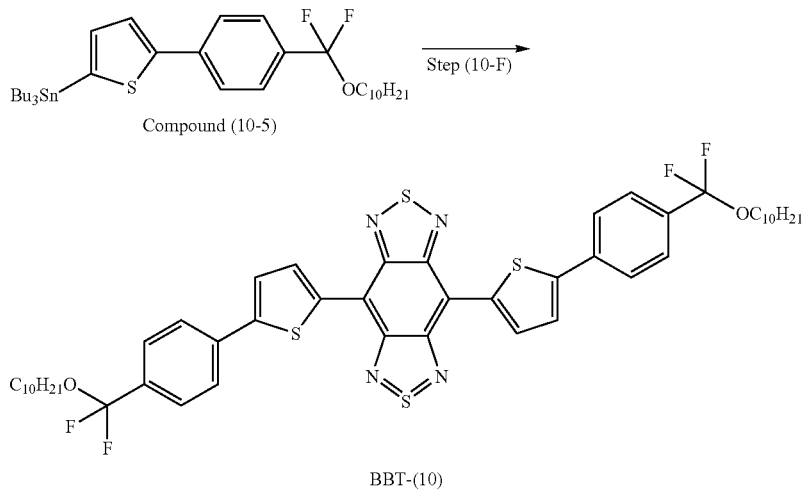

Into a 50-ml glass reaction vessel equipped with a stirring apparatus were placed 4.44 g (6.77 mmol) of Compound (10-5), 0.595 g (1.69 mmol) of dibromobenzobisthiadiazole, 0.36 g (0.507 mmol) of dichlorobis(triphenylphosphine)palladium(II), and 20 ml of toluene. The mixture was reacted at an internal temperature of about 100° C. for 6 hours. And then, the reaction solution was filtered, to provide 1.11 g of a crude product. The crude product was purified, to provide 0.82 g of BBT-(10) in the form of a dark greenish blue solid (Isolated yield: 53%).

The properties of BBT-(10) were as follows.

$^1$H-NMR (500 MHz; CDCl$_3$: 50° C.); 0.90-0.88 (6H, m), 1.29-1.47 (28H, m), 1.71-1.77 (4H, m), 4.04-4.06 (4H, m), 7.67-7.69 (2H, m), 7.84-7.86 (4H, m), 8.01-8.11 (4H, m), 9.06-9.07 (2H, m)

TOF-HRMS (ASAP+); 923.3123 (M+1); Calcd. 923.3144.

Example 1-11

Synthesis of Compound BBT-(15)

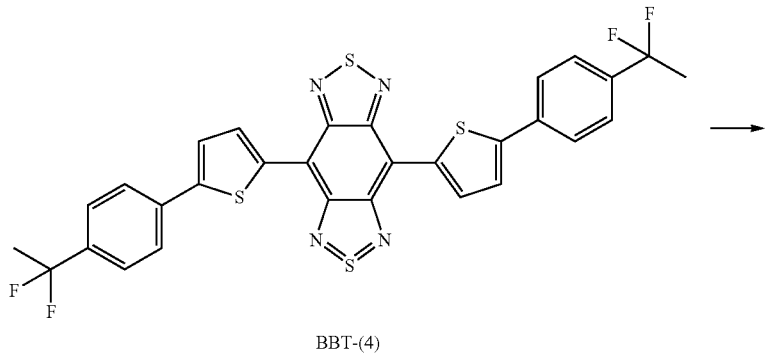

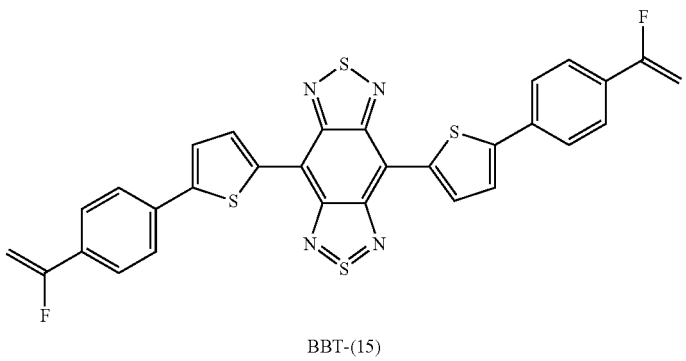

BBT-(15)

BBT-(4) was heated at a temperature of 300° C. or higher and a reduced pressure of 5×10$^{-3}$ Pa or lower, to provide BBT-(15).

The properties of BBT-(15) were as follows.
$^1$H-NMR (400 MHz; deuterated dichlorobenzene: 140° C.): 4.76-5.00 (2H, m)

Only olefin segment was described.

Example 1-12

Synthesis of Compound BBT-(16)

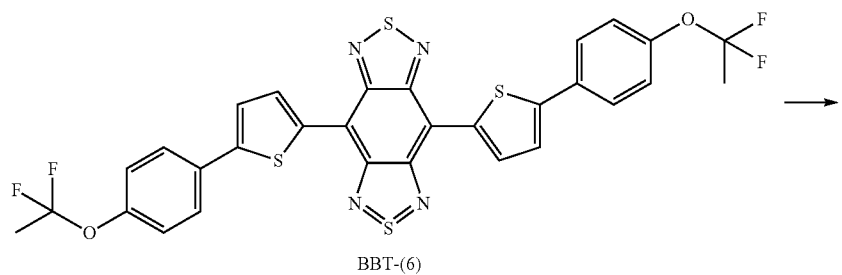

BBT-(6)

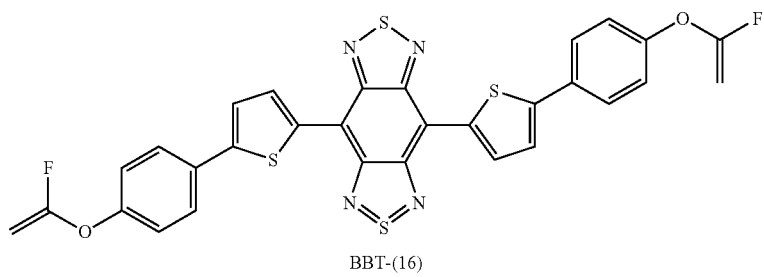

BBT-(16)

BBT-(6) was heated at a temperature of 300° C. or higher and a reduced pressure of 5×10$^{-3}$ Pa or lower, to provide BBT-(16).

The properties of BBT-(16) were as follows.
$^1$H-NMR (400 MHz; deuterated dichlorobenzene: 140° C.): 3.76-4.03 (2H, m)

Only olefin segment was described.

Reference Example 1

Synthesis of Compound BBT-(11)

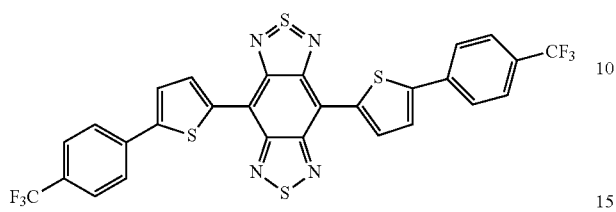

BBT-(11)

BBT-(11) was synthesized by reference to the syntheses of intermediates and the synthesis of BBT-(1) in Examples (1-1), (1-2), (1-3) and (1-4).

The properties of BBT-(11) were as follows.
FAB-MS (−); 646 (M+).

Reference Example 2

Synthesis of Compound BBT-(12)

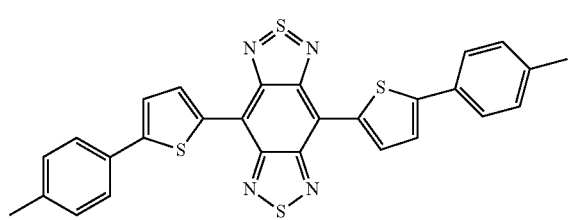

BBT-(12)

BBT-(12) was synthesized by reference to the syntheses of intermediates and the synthesis of BBT-(2) in Examples (2-1) and (2-2).

The properties of BBT-(12) were as follows.
$^1$H-NMR (400 MHz; deuterated dichlorobenzene: 140° C.); 2.27 (6H, s), 7.09-7.11 (4H, m), 7.43-7.44 (2H, m), 7.60-7.63 (4H, m), 9.00-9.01 (2H, m)
CI-MS; 538 (M+).

Reference Example 3

Synthesis of Compound BBT-(13)

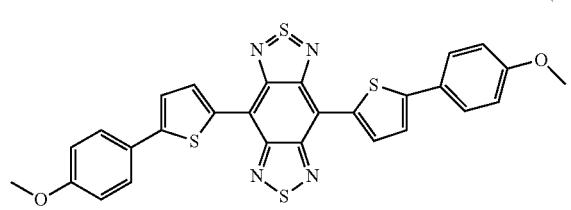

BBT-(13)

BBT-(13) was synthesized by reference to the syntheses of intermediates and the synthesis of BBT-(2) in Examples (2-1) and (2-2).

The properties of BBT-(13) were as follows.
$^1$H-NMR (400 MHz; deuterated dichlorobenzene: 140° C.); 3.69 (6H, s), 6.85-6.87 (4H, m), 7.36-7.40 (2H, m), 7.63-7.65 (4H, m), 9.00 (2H, brs)
TOF-SIMS; 571 (M+).

Reference Example 4

Synthesis of Compound BBT-(14)

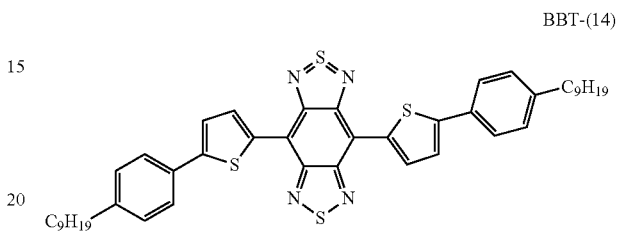

BBT-(14)

BBT-(14) was synthesized by reference to the syntheses of intermediates and the synthesis of BBT-(2) in Examples (2-1) and (2-2).

The properties of BBT-(14) were as follows.
$^1$H-NMR (400 MHz; deuterated dichlorobenzene: 140° C.); 0.84-0.87 (6H, m), 1.26-1.38 (24H, m), 1.62-1.69 (4H, m), 2.59-2.63 (4H, m), 7.17-7.19 (4H, m), 7.44-7.45 (2H, m), 7.65-7.68 (4H, m), 9.01-9.02 (2H, m)
TOF-SIMS; 763 (M+)

[Solubility Experiment 3]

1 mg of each compound shown in Table 1 [BBT-(1)-BBT-(14)] was added to 1 mL of a solvent (chlorobenzene) and the mixture was heated to 100° C. or 140° C., and the solubility was evaluated by visual observation. A compound which was completely dissolved in the solvent was evaluated as ○, a compound which was partially dissolved in the solvent was evaluated as Δ, and a compound which was not dissolved in the solvent was evaluated as ×. The results are shown in Table 1.

TABLE 1

Solubility of BBT Compounds

| Example | Compound | Position | Terminal substituent | chlorobenzene (° C.) 100 | chlorobenzene (° C.) 140 |
|---|---|---|---|---|---|
| Example 1-1 | BBT-(1) | p | OCF3 | ○ | ○ |
| Example 1-2 | BBT-(2) | m | OCF3 | ○ | ○ |
| Example 1-3 | BBT-(3) | o | OCF3 | ○ | ○ |
| Example 1-4 | BBT-(4) | p | CF2Me | Δ | ○ |
| Example 1-5 | BBT-(5) | p | CF2C10H21 | ○ | ○ |
| Example 1-6 | BBT-(6) | p | OCF2Me | Δ | ○ |
| Example 1-7 | BBT-(7) | p | OCF2C9H19 | ○ | ○ |
| Example 1-8 | BBT-(8) | p | C8F17 | Δ | ○ |
| Example 1-9 | BBT-(9) | p | CFHCH2CHMe2 | Δ | ○ |
| Example 1-10 | BBT-(10) | p | CF2OC10H21 | ○ | ○ |
| Reference Example 1 | BBT-(11) | p | CF3 | × | × |
| Reference Example 2 | BBT-(12) | p | CH3 | ○ | ○ |
| Reference Example 3 | BBT-(13) | p | OCH3 | × | ○ |
| Reference Example 4 | BBT-(14) | p | C9H19 | ○ | ○ |

*○: Completely dissolved, Δ: Partially dissolved, ×: Not dissolved

Example 2

Organic TFT Comprising BBT-(1) on HMDS-Modified Substrate

With the use of the BBT-(1) obtained in Example 1-1, a TFT device was produced and evaluated.
(Production of Substrate for TFT)

A commercially available silicon wafer having a thermally grown silicon dioxide with a film thickness of 200 nm formed on the surface was used as the substrate for the organic TFT. The silicon wafer had low resistance, and also functioned as the gate electrode of the organic TFT. In addition, the silicon oxide film was used as the gate insulating film. The silicon wafer was washed with a mixture solution of hydrogen peroxide water and sulfuric acid, and the surface was cleaned by UV ozone treatment immediately before the silicon wafer was used in the subsequent step. The substrate thus treated is referred to as "bare substrate" hereinafter.

The "bare substrate" was immersed and left still in hexamethyldisilazane, which was commercially available, for 12 hours or more, so that the surface of the substrate was modified. The substrate thus treated is referred to as "HMDS-modified substrate" hereinafter.
(Production of Organic Semiconductor Layer)

With the use of the BBT-(1), which was subjected to sublimation for purification, an organic semiconductor layer with a film thickness of about 50 nm was formed on the "HMDS-modified substrate" by vacuum deposition. During the formation of the organic semiconductor layer, the pressure in the chamber of the vapor deposition apparatus was $2.7 \times 10^{-5}$ Pa, and the organic semiconductor compound was contained in a carbon crucible and heated by tantalum filament wound around the crucible, to perform vapor deposition. The temperature to heat the carbon crucible was 295° C. The deposition rate was 0.2±0.1 Å/sec.
(Production of Source Electrode and Drain Electrode)

A gold film was formed on the organic semiconductor layer by vacuum deposition, using a metal mask, to form a source electrode and a drain electrode, thereby producing an organic TFT. The channel width and channel length of the organic TFT were 1000 μm and 70 μm, respectively. The thickness of the electrode layer was about 50 nm.

Figure 5:
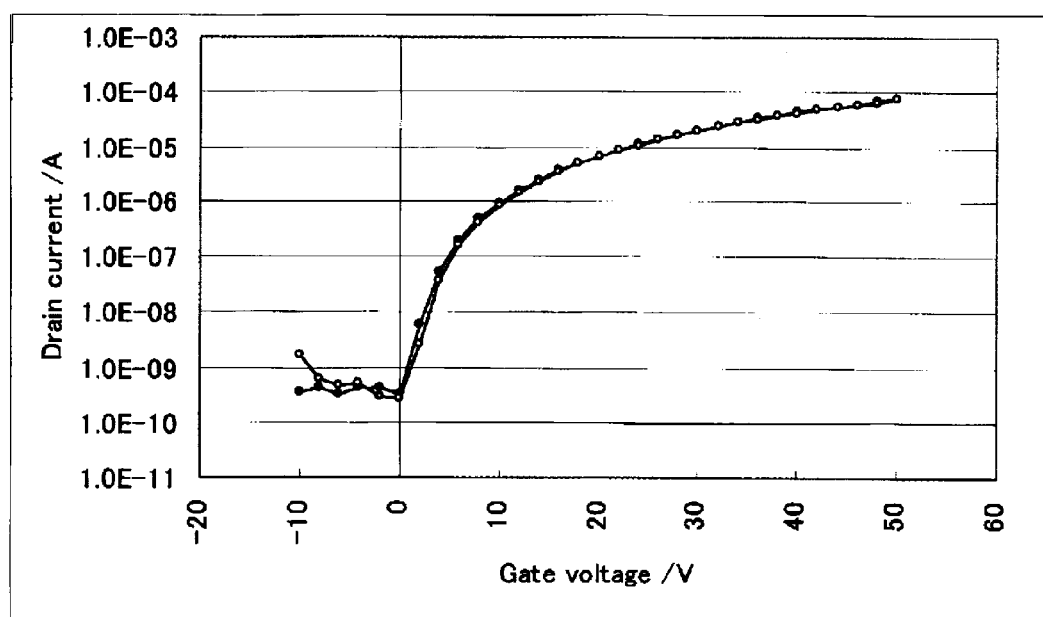
FIG. 5 is a graph showing the electrical properties of the organic TFT of Example 2.

The electrical properties of the produced organic TFT, which were evaluated at a drain voltage of 50 V, are shown in FIG. 5. In FIG. 5, the horizontal axis indicates gate voltage (V), and the vertical axis indicates drain current (A). The device had the properties of n-type semiconductor.

The field-effect mobility (μ) can be calculated by the following formula (Formula A), which represents the drain current $I_d$.

$$I_d = (W/2L)\mu C_i (V_g \cdot V_t)^2 \quad \text{(Formula A)}$$

wherein L and W represent the channel length and the channel width, respectively, and $C_i$ represents the capacity of the insulating layer per unit area, and $V_g$ represents the gate voltage and $V_t$ represents the threshold voltage.

As a result of the calculation of the field-effect mobility (μ) using the (Formula A), it was found that the organic TFT comprising BBT-(1) on the "HMDS-modified substrate" had a field-effect mobility of $4.1 \times 10^{-1}$ cm$^2$/Vs.

The organic TFT was further left in the atmosphere for 13 days, and then the electrical properties of the organic TFT were evaluated at a drain voltage of 50 V again. As a result, it was found that the organic TFT had a field-effect mobility of $8.0 \times 10^{-1}$ cm$^2$/Vs.

In addition, the electrical properties of the same organic TFT as described above were evaluated at a drain voltage of 80 V. As a result, it was found that the organic TFT had a field-effect mobility of 1.0 cm$^2$/Vs.

The organic TFT was further left in the atmosphere for 15 days, i.e. 28 days in total, and then the electrical properties of the organic TFT were evaluated at a drain voltage of 80 V. As a result, it was found that the organic TFT had a field-effect mobility of 1.1 cm$^2$/Vs.

The organic TFT was further left in the atmosphere for 28 days, i.e. 56 days in total, and then the electrical properties of the organic TFT were evaluated at a drain voltage of 80 V. As a result, it was found that the organic TFT had a field-effect mobility of $9.7 \times 10^{-1}$ cm$^2$/Vs.

The organic TFT was further left in the atmosphere for 68 days, i.e. 124 days in total, and then the electrical properties of the organic TFT were evaluated at a drain voltage of 80 V. As a result, it was found that the organic TFT had a field-effect mobility of $9.7 \times 10^{-1}$ cm$^2$/Vs.

Example 3

Organic TFT Comprising BBT-(1) on PS Substrate

With the use of the BBT-(1) obtained in Example 1-1, a TFT device was produced and evaluated.
(Production of Substrate for TFT)

A solution prepared by dissolving 0.5 wt % polystyrene, which was commercially available, in xylene was applied onto the "bare substrate" by spin-coating, and then heated at 150° C. for 1 hour, so that a thin film of polystyrene with a thickness of 20 nm was formed on the surface of the substrate. The substrate thus treated is referred to as "PS substrate" hereinafter.
(Production of Organic Semiconductor Layer)

With the use of the BBT-(1), which was subjected to sublimation for purification, an organic semiconductor layer with a film thickness of about 50 nm was formed on the "PS substrate" by vacuum deposition. During the formation of the organic semiconductor layer, the pressure in the chamber of the vapor deposition apparatus was $2.7 \times 10^{-5}$ Pa, and the organic semiconductor compound was contained in a carbon crucible and heated by tantalum filament wound around the crucible, to perform vapor deposition. The temperature to heat the carbon crucible was 295° C. The deposition rate was 0.2±0.1 Å/sec.
(Production of Source Electrode and Drain Electrode)

A gold film was formed on the organic semiconductor layer by vacuum deposition, using a metal mask, to form a source electrode and a drain electrode, thereby producing an organic TFT. The channel width and channel length of the organic TFT were 1000 μm and 70 μm, respectively. The thickness of the electrode layer was about 50 nm.

Figure 6:
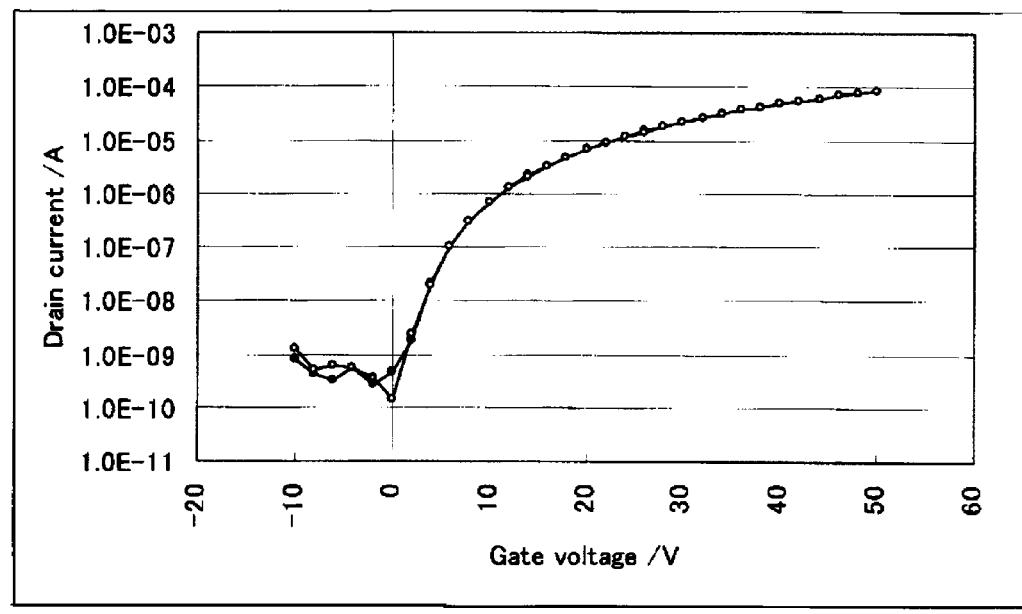
FIG. 6 is a graph showing the electrical properties of the organic TFT of Example 3.

The electrical properties of the produced organic TFT, which were evaluated at a drain voltage of 50 V, are shown in FIG. 6. In FIG. 6, the horizontal axis indicates gate voltage (V), and the vertical axis indicates drain current (A). The device had the properties of n-type semiconductor.

As a result of the calculation of the field-effect mobility (μ) using the (Formula A), it was found that the organic TFT comprising BBT-(1) on the "PS substrate" had a field-effect mobility of $5.1 \times 10^{-1}$ cm$^2$/Vs.

The organic TFT was further left in the atmosphere for 13 days, and then the electrical properties of the organic TFT were evaluated at a drain voltage of 50 V again. As a result, it was found that the organic TFT had a field-effect mobility of $8.2 \times 10^{-1}$ cm$^2$/Vs.

In addition, the electrical properties of the same organic TFT as described above were evaluated at a drain voltage of 80 V. As a result, it was found that the organic TFT had a field-effect mobility of 1.6 cm$^2$/Vs.

The organic TFT was further left in the atmosphere for 15 days, i.e. 28 days in total, and then the electrical properties of the organic TFT were evaluated at a drain voltage of 80 V. As a result, it was found that the organic TFT had a field-effect mobility of 1.6 cm$^2$/Vs.

The organic TFT was further left in the atmosphere for 28 days, i.e. 56 days in total, and then the electrical properties of the organic TFT were evaluated at a drain voltage of 80 V. As a result, it was found that the organic TFT had a field-effect mobility of 1.6 cm$^2$/Vs.

The organic TFT was further left in the atmosphere for 68 days, i.e. 124 days in total, and then the electrical properties of the organic TFT were evaluated at a drain voltage of 80 V. As a result, it was found that the organic TFT had a field-effect mobility of 1.5 cm$^2$/Vs.

Comparative Example 1

Organic TFT Comprising FPTBBT on HMDS-Modified Substrate

With the use of the FPTBBT which was subjected to sublimation for purification, instead of BBT-(1), an organic TFT was produced in the same way as in Example 2. During the formation of the organic semiconductor layer, the pressure in the chamber was $3.3 \times 10^{-5}$ Pa, and the temperature to heat the carbon crucible was 320° C.

Figure 7:
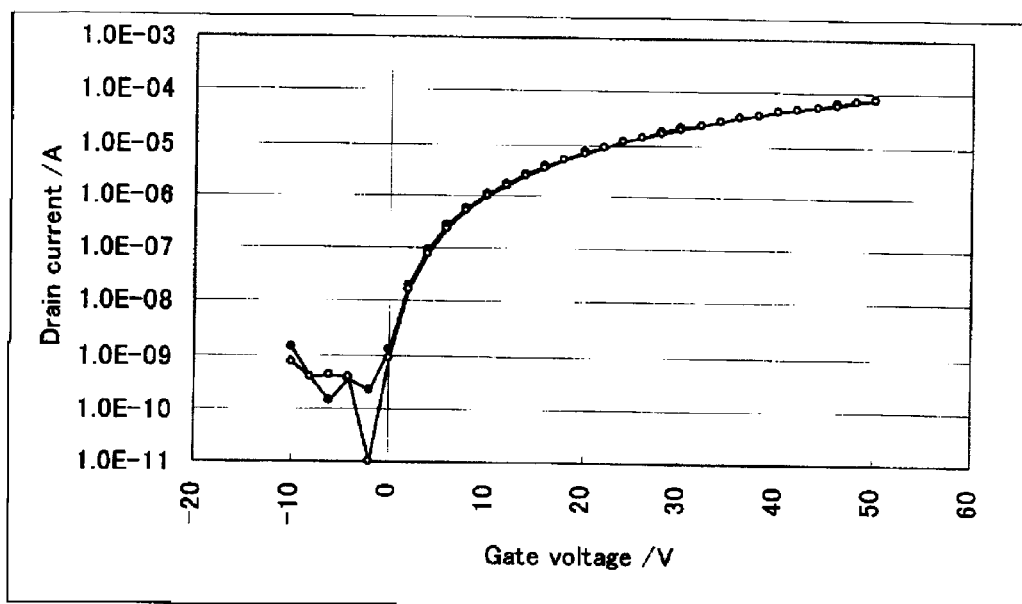
FIG. 7 is a graph showing the electrical properties of the organic TFT of Comparative Example 1.

The electrical properties of the produced organic TFT, which were evaluated at a drain voltage of 50 V, are shown in FIG. 7. In FIG. 7, the horizontal axis indicates gate voltage (V), and the vertical axis indicates drain current (A). The device had the properties of n-type semiconductor.

As a result of the calculation of the field-effect mobility ($\mu$) using the (Formula A), it was found that the organic TFT comprising FPTBBT on the "HMDS-modified substrate" had a field-effect mobility of $4.0 \times 10^{-1}$ cm$^2$/Vs.

The organic TFT was further left in the atmosphere for 13 days, and then the electrical properties of the organic TFT were evaluated at a drain voltage of 50 V again. As a result, it was found that the organic TFT had a field-effect mobility of $4.5 \times 10^{-1}$ cm$^2$/Vs.

Comparative Example 2

Organic TFT Comprising FPTBBT on PS Substrate

With the use of the FPTBBT which was subjected to sublimation for purification, instead of BBT-(1), an organic TFT was produced in the same way as in Example 3. During the formation of the organic semiconductor layer, the pressure in the chamber was $3.3 \times 10^{-5}$ Pa, and the temperature to heat the carbon crucible was 320° C.

Figure 8:
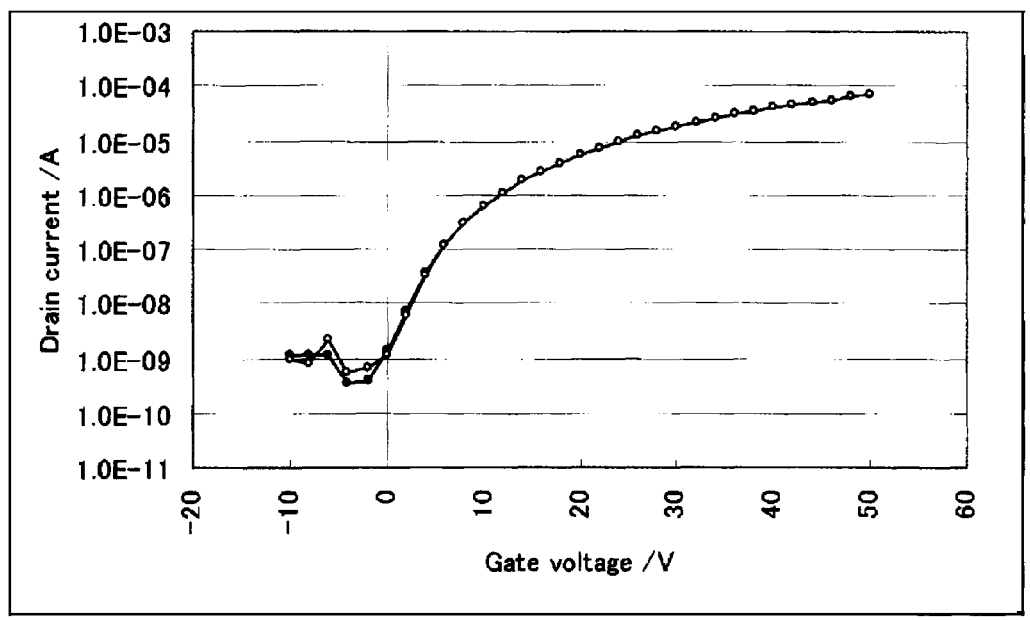
FIG. 8 is a graph showing the electrical properties of the organic TFT of Comparative Example 2.

The electrical properties of the produced organic TFT, which were evaluated at a drain voltage of 50 V, are shown in FIG. 8. In FIG. 8, the horizontal axis indicates gate voltage (V), and the vertical axis indicates drain current (A). The device had the properties of n-type semiconductor.

As a result of the calculation of the field-effect mobility ($\mu$) using the (Formula A), it was found that the organic TFT comprising FPTBBT on the "PS substrate" had a field-effect mobility of $4.0 \times 10^{-1}$ cm$^2$/Vs.

The organic TFT was further left in the atmosphere for 13 days, and then the electrical properties of the organic TFT were evaluated at a drain voltage of 50 V again. As a result, it was found that the organic TFT had a field-effect mobility of $3.0 \times 10^{-1}$ cm$^2$/Vs.

Example 4

With the use of the Compound BBT-(2) obtained in Example 1-2, a TFT device was produced and evaluated.
[Organic TFT Comprising BBT-(2) on HMDS-Modified Substrate]

With the use of the BBT-(2) which was subjected to sublimation for purification, instead of BBT-(1), an organic TFT was produced in the same way as in Example 2. During the formation of the organic semiconductor layer, the pressure in the chamber was $2.0 \times 10^{-4}$ Pa.

Figure 9:
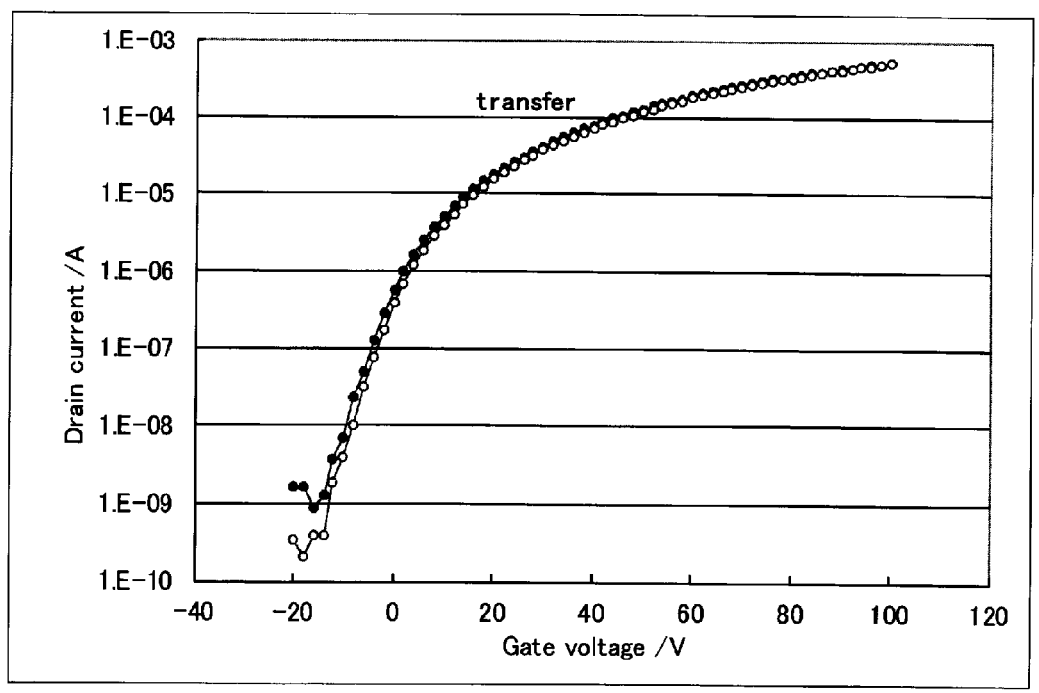
FIG. 9 is a graph showing the electrical properties of the organic TFT of Example 4.

The electrical properties of the produced organic TFT, which were evaluated at a drain voltage of 100 V, are shown in FIG. 9. In FIG. 9, the horizontal axis indicates gate voltage (V), and the vertical axis indicates drain current (A). The device had the properties of n-type semiconductor.

As a result of the calculation of the field-effect mobility ($\mu$) using the (Formula A), it was found that the organic TFT comprising BBT-(2) on the "HMDS-modified substrate" had a field-effect mobility of $5.6 \times 10^{-1}$ cm$^2$/Vs.

Example 5

Organic TFT Comprising BBT-(2) on PS Substrate

With the use of the BBT-(2) which was subjected to sublimation for purification, instead of BBT-(1), an organic TFT was produced in the same way as in Example 3. During the formation of the organic semiconductor layer, the pressure in the chamber was $2.0 \times 10^{-4}$ Pa.

Figure 10:
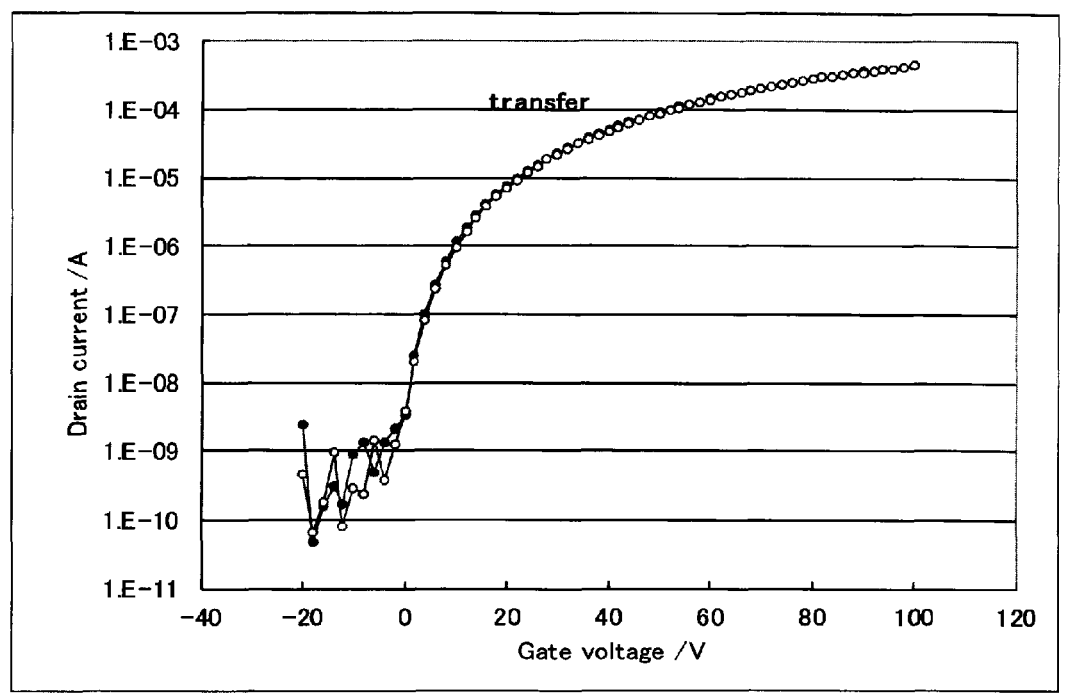
FIG. 10 is a graph showing the electrical properties of the organic TFT of Example 5.

The electrical properties of the produced organic TFT, which were evaluated at a drain voltage of 100 V, are shown in FIG. 10. In FIG. 10, the horizontal axis indicates gate voltage (V), and the vertical axis indicates drain current (A). The device had the properties of n-type semiconductor.

As a result of the calculation of the field-effect mobility ($\mu$) using the (Formula A), it was found that the organic TFT comprising BBT-(2) on the "PS substrate" had a field-effect mobility of $5.3 \times 10^{-1}$ cm$^2$/Vs.

Example 6

With the use of the Compound BBT-(6) obtained in Example 1-6, a TFT device was produced and evaluated.
[Organic TFT Comprising BBT-(6) on HMDS-Modified Substrate]

With the use of the BBT-(6) which was subjected to sublimation for purification, instead of BBT-(1), an organic TFT was produced in the same way as in Example 2. During the formation of the organic semiconductor layer, the pressure in the chamber was $2.4 \times 10^{-4}$ Pa.

Figure 11:
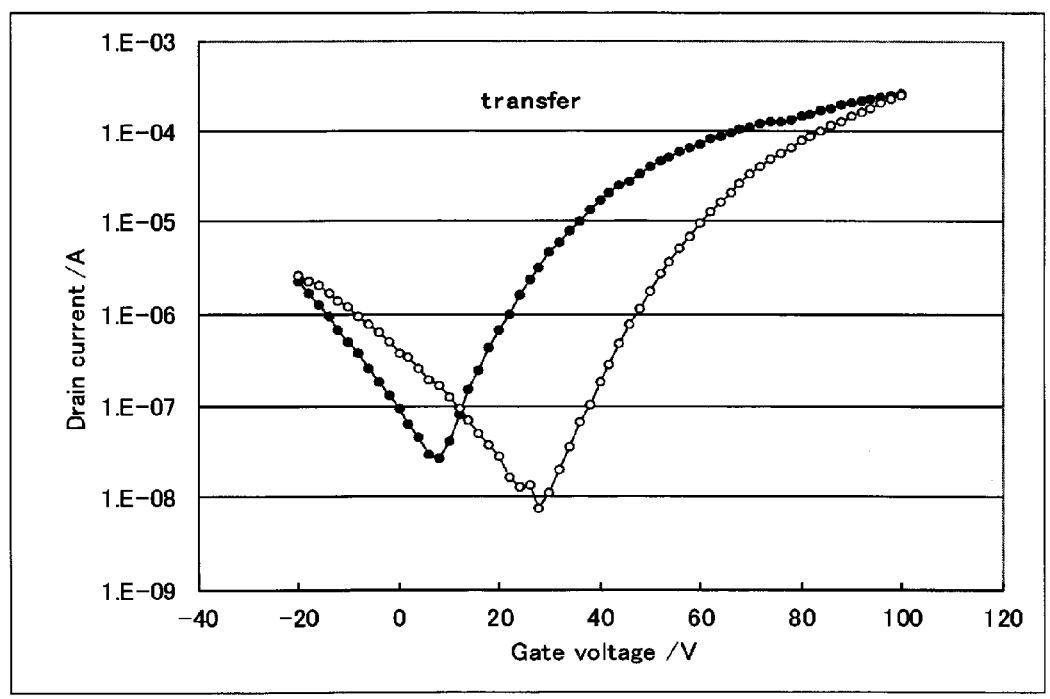
FIG. 11 is a graph showing the electrical properties of the organic TFT of Example 6.

The electrical properties of the produced organic TFT, which were evaluated at a drain voltage of 100 V, are shown in FIG. 11. In FIG. 11, the horizontal axis indicates gate voltage (V), and the vertical axis indicates drain current (A). The device had the properties of n-type semiconductor.

As a result of the calculation of the field-effect mobility ($\mu$) using the (Formula A), it was found that the organic TFT comprising BBT-(6) on the "HMDS-modified substrate" had a field-effect mobility of 1.1 cm$^2$/Vs.

The organic TFT was further left in the atmosphere for 7 days, and then the electrical properties of the organic TFT were evaluated at a drain voltage of 100 V again. As a result, it was found that the organic TFT had a field-effect mobility of 1.6 cm²/Vs.

Example 7

Organic TFT Comprising BBT-(6) on PS Substrate

With the use of the BBT-(6) which was subjected to sublimation for purification, instead of BBT-(1), an organic TFT was produced in the same way as in Example 3. During the formation of the organic semiconductor layer, the pressure in the chamber was $2.0 \times 10^{-4}$ Pa.

Figure 12:
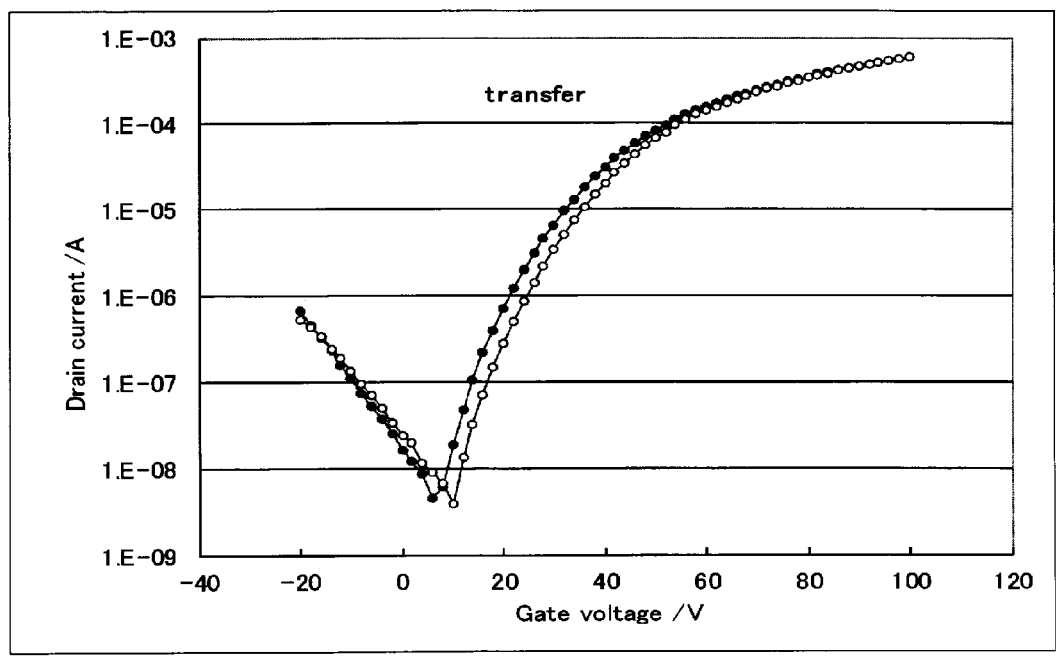
FIG. 12 is a graph showing the electrical properties of the organic TFT of Example 7.

The electrical properties of the produced organic TFT, which were evaluated at a drain voltage of 100 V, are shown in FIG. 12. In FIG. 12, the horizontal axis indicates gate voltage (V), and the vertical axis indicates drain current (A). The device had the properties of n-type semiconductor.

As a result of the calculation of the field-effect mobility (μ) using the (Formula A), it was found that the organic TFT comprising BBT-(6) on the "PS substrate" had a field-effect mobility of 1.5 cm²/Vs.

The organic TFT was further left in the atmosphere for 7 days, and then the electrical properties of the organic TFT were evaluated at a drain voltage of 100 V again. As a result, it was found that the organic TFT had a field-effect mobility of 1.8 cm²/Vs.

Comparative Example 3

With the use of the Compound BBT-(13) obtained in Reference Example 3, a TFT device was produced and evaluated. [Organic TFT Comprising BBT-(13) on HMDS-Modified Substrate]

With the use of the BBT-(13) which was subjected to sublimation for purification, instead of BBT-(1), an organic TFT was produced in the same way as in Example 2. During the formation of the organic semiconductor layer, the pressure in the chamber was $1.3 \times 10^{-5}$ Pa, and the temperature to heat the carbon crucible was 337° C.

Figure 13:
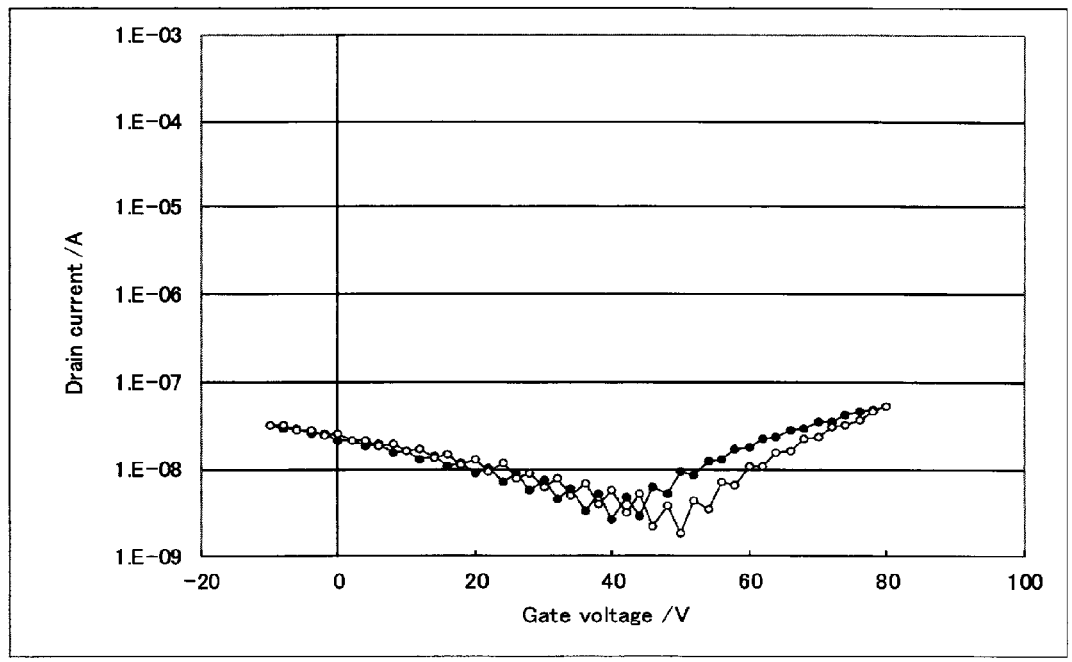
FIG. 13 is a graph showing the electrical properties of the organic TFT of Comparative Example 3.

The electrical properties of the produced organic TFT, which were evaluated at a drain voltage of 80 V, are shown in FIG. 13. In FIG. 13, the horizontal axis indicates gate voltage (V), and the vertical axis indicates drain current (A). The device had the properties of n-type semiconductor.

As a result of the calculation of the field-effect mobility (μ) using the (Formula A), it was found that the organic TFT comprising BBT-(13) on the "HMDS-modified substrate" had a field-effect mobility of $2.0 \times 10^{-4}$ cm²/Vs.

Comparative Example 4

Organic TFT Comprising BBT-(13) on PS Substrate

With the use of the BBT-(13) which was subjected to sublimation for purification, instead of BBT-(1), an organic TFT was produced in the same way as in Example 3. During the formation of the organic semiconductor layer, the pressure in the chamber was $1.3 \times 10^{-5}$ Pa, and the temperature to heat the carbon crucible was 337° C.

Figure 14:
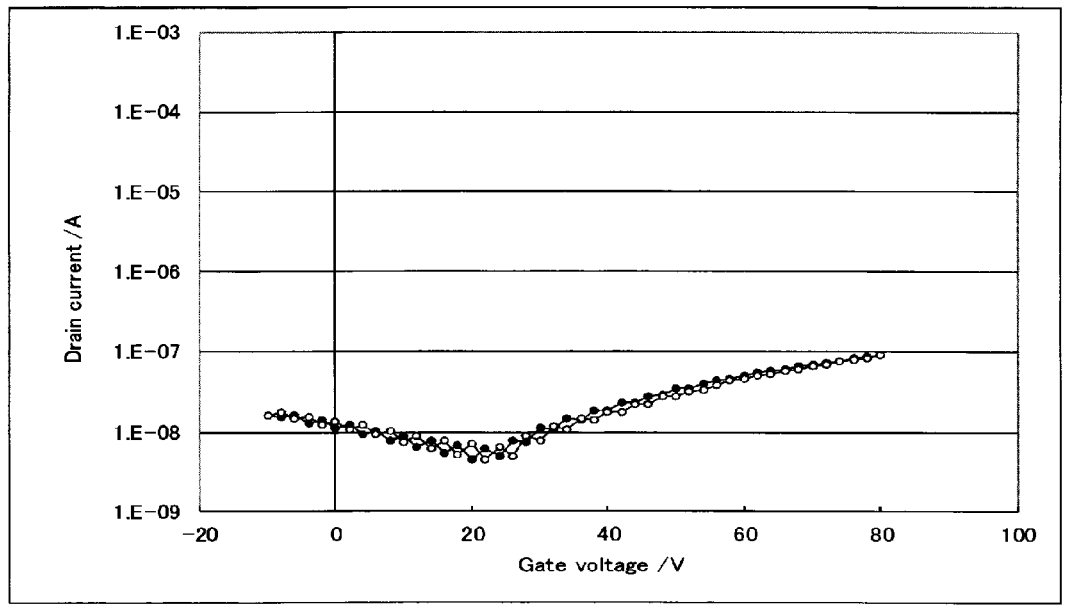
FIG. 14 is a graph showing the electrical properties of the organic TFT of Comparative Example 4.

The electrical properties of the produced organic TFT, which were evaluated at a drain voltage of 80 V, are shown in FIG. 14. In FIG. 14, the horizontal axis indicates gate voltage (V), and the vertical axis indicates drain current (A). The device had the properties of n-type semiconductor.

As a result of the calculation of the field-effect mobility (μ) using the (Formula A), it was found that the organic TFT comprising BBT-(13) on the "PS substrate" had a field-effect mobility of $2.0 \times 10^{-4}$ cm²/Vs.

Comparative Example 5

With the use of the Compound BBT-(12) obtained in Reference Example 2, a TFT device was produced and evaluated. [Organic TFT Comprising BBT-(12) on HMDS-Modified Substrate]

With the use of the BBT-(12) which was subjected to sublimation for purification, instead of BBT-(1), an organic TFT was produced in the same way as in Example 2. During the formation of the organic semiconductor layer, the pressure in the chamber was $1.7 \times 10^{-5}$ Pa, and the temperature to heat the carbon crucible was 325° C.

Figure 15:
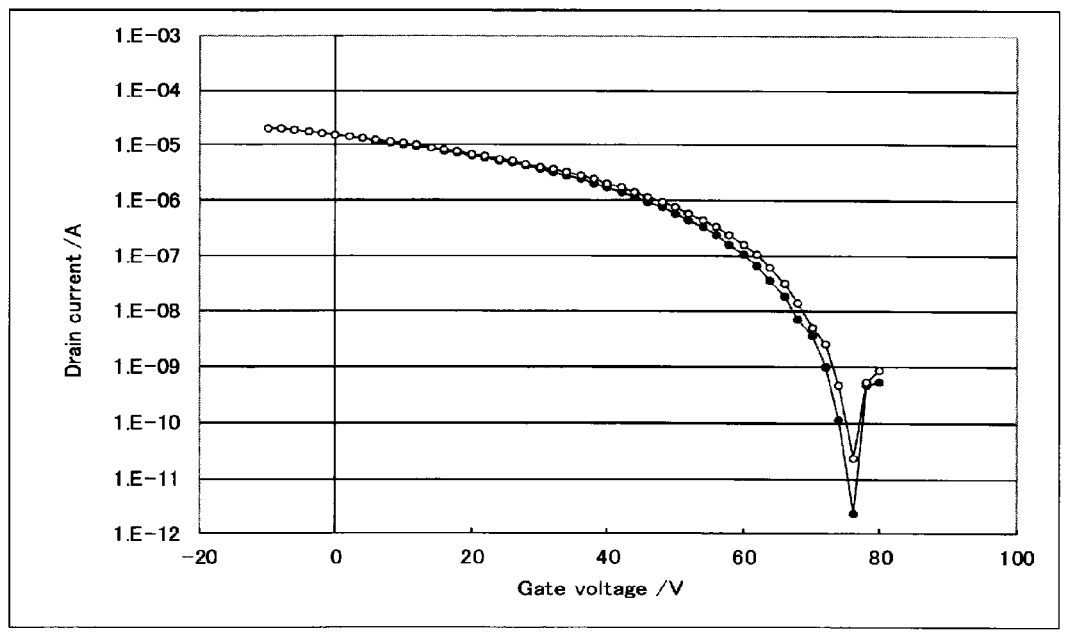
FIG. 15 is a graph showing the electrical properties of the organic TFT of Comparative Example 5.

The electrical properties of the produced organic TFT, which were evaluated at a drain voltage of 80 V, are shown in FIG. 15. In FIG. 15, the horizontal axis indicates gate voltage (V), and the vertical axis indicates drain current (A). As a result, it was confirmed that the BBT-(12) on the "HMDS-modified substrate" did not have the properties of n-type transistor.

Comparative Example 6

Organic TFT Comprising BBT-(12) on PS Substrate

With the use of the BBT-(12) which was subjected to sublimation for purification, instead of BBT-(1), an organic TFT was produced in the same way as in Example 3. During the formation of the organic semiconductor layer, the pressure in the chamber was $1.7 \times 10^{-5}$ Pa, and the temperature to heat the carbon crucible was 325° C.

Figure 16:
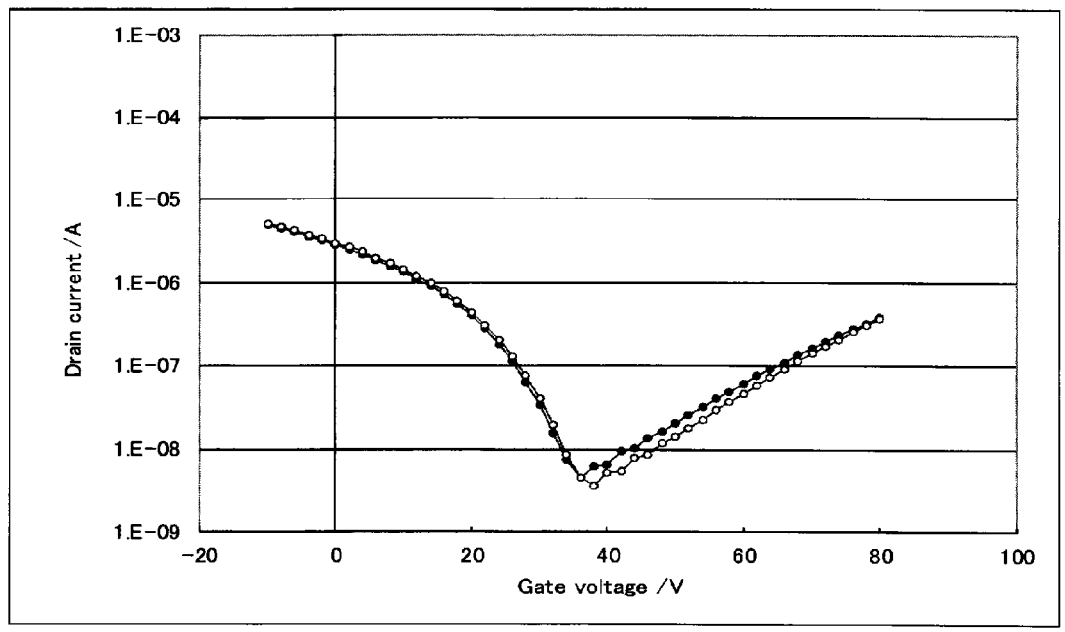
FIG. 16 is a graph showing the electrical properties of the organic TFT of Comparative Example 6.

The electrical properties of the produced organic TFT, which were evaluated at a drain voltage of 80 V, are shown in FIG. 16. In FIG. 16, the horizontal axis indicates gate voltage (V), and the vertical axis indicates drain current (A). The device had the properties of n-type semiconductor.

As a result of the calculation of the field-effect mobility (μ) using the (Formula A), it was found that the organic TFT comprising BBT-(12) on the "PS substrate" had a field-effect mobility of $4.9 \times 10^{-3}$ cm²/Vs.

Example 8

With the use of the Compound BBT-(5) obtained in Example 1-5, a TFT device was produced and evaluated.
[Organic TFT Comprising BBT-(5) on PS Substrate]
(Production of Organic Semiconductor Layer)

0.18 mL of a solution, which was prepared by adding the BBT-(5) to 1,2-dichlorobenzene so that the concentration was 0.3 wt %, and heating the mixture at 130° C., was dropped onto the "PS substrate", and then spin-coating was performed at 1000 rpm for 30 seconds, to form an organic semiconductor layer with a film thickness of about 20 nm. And then, the "PS substrate" on which the organic semiconductor layer was formed was heated at 180° C. for 35 minutes.
(Production of Source Electrode and Drain Electrode)

A gold film was formed on the organic semiconductor layer by vacuum deposition, using a metal mask, to form a source electrode and a drain electrode, thereby producing an organic TFT. The channel width and channel length of the organic TFT were 2000 μm and 70 μm, respectively. The thickness of the electrode layer was about 50 nm.

Figure 17:
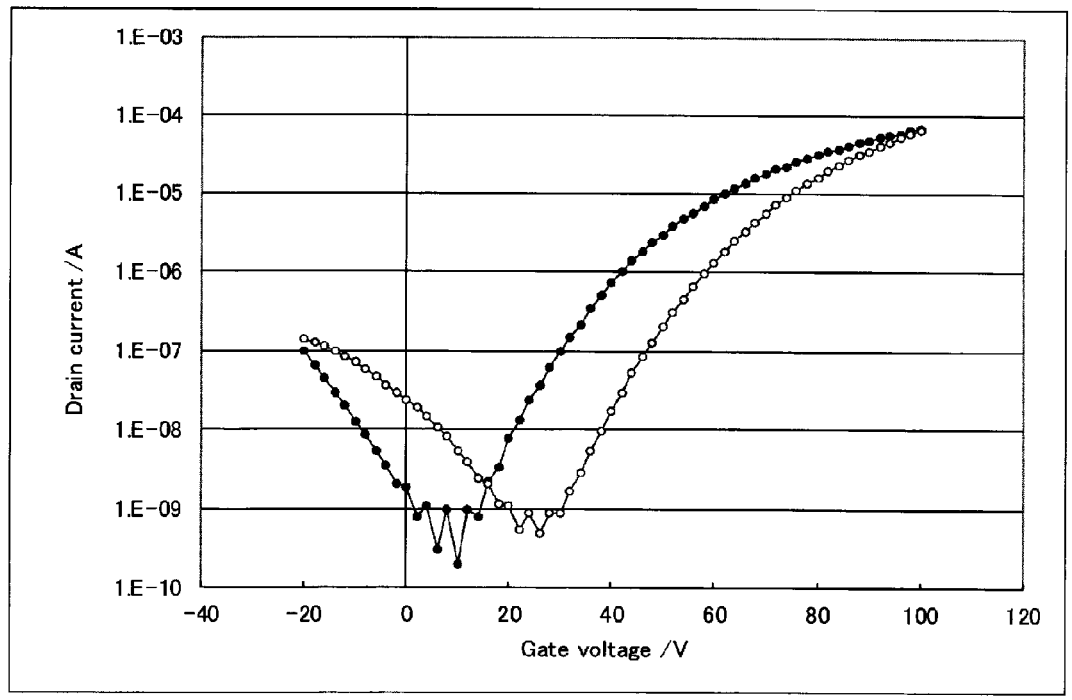
FIG. 17 is a graph showing the electrical properties of the organic TFT of Example 8.

The electrical properties of the produced organic TFT, which were evaluated at a drain voltage of 100 V, are shown in FIG. 17. In FIG. 17, the horizontal axis indicates gate voltage (V), and the vertical axis indicates drain current (A). The device had the properties of n-type semiconductor.

As a result of the calculation of the field-effect mobility ($\mu$) using the (Formula A), it was found that the organic TFT comprising BBT-(5) on the "PS substrate" had a field-effect mobility of $1.0 \times 10^{-1}$ cm$^2$/Vs.

Example 9

With the use of the Compound BBT-(2) obtained in Example 1-2, a TFT device was produced and evaluated.
[Organic TFT Comprising BBT-(2) on PS Substrate]
(Production of Organic Semiconductor Layer)

0.18 mL of a solution, which was prepared by adding the BBT-(2) to 1,2-dichlorobenzene so that the concentration was 0.3 wt %, and heating the mixture at 130° C., was dropped onto the "PS substrate", and then spin-coating was performed at 1000 rpm for 30 seconds, to form an organic semiconductor layer with a film thickness of about 20 nm. And then, the "PS substrate" on which the organic semiconductor layer was formed was heated at 180° C. for 35 minutes.
(Production of Source Electrode and Drain Electrode)

A gold film was formed on the organic semiconductor layer by vacuum deposition, using a metal mask, to form a source electrode and a drain electrode, thereby producing an organic TFT. The channel width and channel length of the organic TFT were 2000 μm and 70 μm, respectively. The thickness of the electrode layer was about 50 nm.

Figure 18:
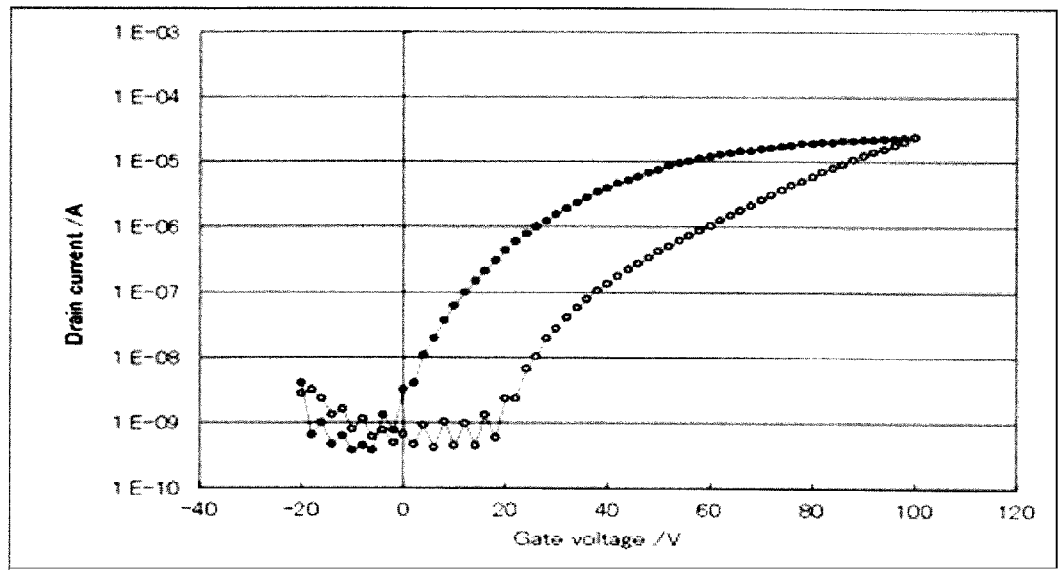
FIG. 18 is a graph showing the electrical properties of the organic TFT of Example 9.

The electrical properties of the produced organic TFT, which were evaluated at a drain voltage of 100 V, are shown in FIG. 18. In FIG. 18, the horizontal axis indicates gate voltage (V), and the vertical axis indicates drain current (A). The device had the properties of n-type semiconductor.

As a result of the calculation of the field-effect mobility ($\mu$) using the (Formula A), it was found that the organic TFT comprising BBT-(2) on the "PS substrate" had a field-effect mobility of $2.6 \times 10^{-2}$ cm$^2$/Vs.

Comparative Example 7

With the use of the Compound BBT-(14) obtained in Reference Example 4, a TFT device was produced and evaluated.
[Organic TFT Comprising BBT-(14) on PS Substrate]
(Production of Organic Semiconductor Layer)

0.18 mL of a solution, which was prepared by adding the BBT-(14) to 1,2-dichlorobenzene so that the concentration was 0.3 wt %, and heating the mixture at 130° C., was dropped onto the "PS substrate", and then spin-coating was performed at 1000 rpm for 30 seconds, to form an organic semiconductor layer with a film thickness of about 17 nm. And then, the "PS substrate" on which the organic semiconductor layer was formed was heated at 180° C. for 35 minutes.
(Production of Source Electrode and Drain Electrode)

A gold film was formed on the organic semiconductor layer by vacuum deposition, using a metal mask, to form a source electrode and a drain electrode, thereby producing an organic TFT. The channel width and channel length of the organic TFT were 2000 μm and 70 μm, respectively. The thickness of the electrode layer was about 50 nm.

Figure 19:
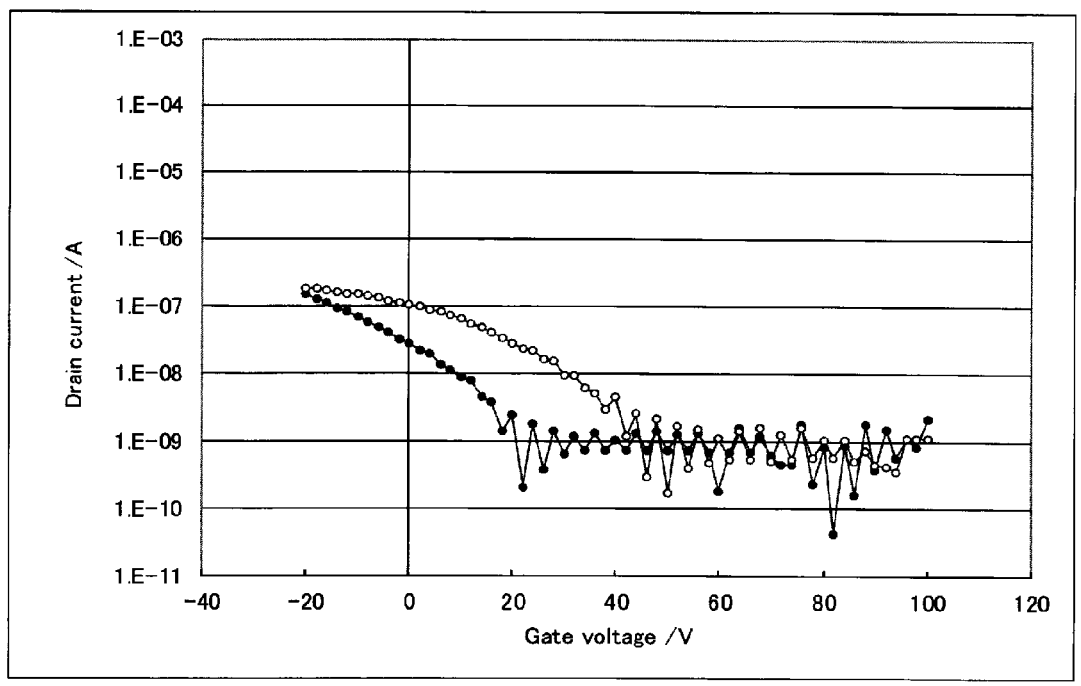
FIG. 19 is a graph showing the electrical properties of the organic TFT of Comparative Example 7.

The electrical properties of the produced organic TFT, which were evaluated at a drain voltage of 100 V, are shown in FIG. 19. In FIG. 19, the horizontal axis indicates gate voltage (V), and the vertical axis indicates drain current (A). As a result, it was confirmed that the BBT-(14) on the "PS substrate" did not have the properties of n-type transistor.

As can be seen from the results, the benzobis(thiadiazole) derivative of the present invention has high field-effect mobility at the initial stage and even after being left for 124 days. That is to say, it was demonstrated that the benzobis(thiadiazole) derivative of the present invention combines high field-effect mobility with the property of being stable in the atmosphere.

INDUSTRIAL APPLICABILITY

According to the present invention, there may be provided a benzobis(thiadiazole) derivative, which is soluble in an organic solvent and allows the formation of a thin film by a coating method, and has an excellent hole-electron mobility (field-effect mobility) and an excellent stability in the atmosphere.

Because the benzobis(thiadiazole) derivative of the present invention is thermally stable and has high field-effect mobility, high field-effect mobility may be achieved when the compound is used for a semiconductor layer of an organic TFT. In addition, high luminous efficiency may be achieved when the compound is used for a hole transport layer and/or an electron transport layer of an organic EL device. Additionally, high photoelectric conversion efficiency may be achieved when the compound is used for a charge separation layer and/or a hole transport layer and/or an electron transport layer of a photovoltaic cell.

In addition, the organic EL display comprising arranged pixels, in which the organic TFT of the present invention, and the organic EL device of the present invention or other type of organic EL device are combined, has the advantages of having an excellent luminous efficiency; and having excellent response properties.

DESCRIPTION OF THE MAIN SYMBOLS

11, 21, 31, 111 Substrate
12, 106 Gate electrode
13, 107 Gate insulating film
14, 110 Drain electrode
15, 109 Source electrode
16, 108 Organic semiconductor layer
22, 105 Anode
23, 104 Hole transport layer
24, 103 Luminescent layer
25, 102 Electron transport layer
26, 101 Cathode
112 Barrier layer
113 Protective layer
120 Organic EL device
121 Organic TFT
32 Anode
33 Charge separation layer
34 Cathode

The invention claimed is:
1. A benzobis(thiadiazole) derivative represented by the formula (1)

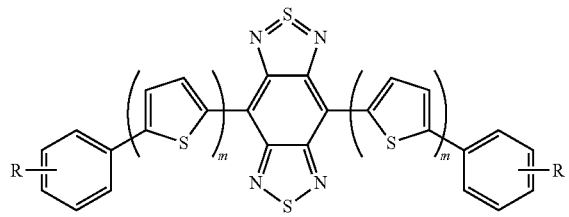

(1)

wherein
R represents a group containing at least one fluorine atom, with the proviso that fluorine atom (F) and trifluoromethyl group (—CF$_3$) are excluded, and
m represents an integer of from 1 to 10.

2. The benzobis(thiadiazole) derivative according to claim 1, wherein the R group comprises a structure represented by any one of the formulae (A-1) to (A-3):

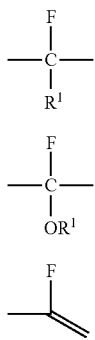

(A-1)

(A-2)

(A-3)

wherein
R$^1$ represents hydrogen atom, fluorine atom, linear or branched alkyl group, or linear or branched alkyl group substituted with at least one fluorine atom.

3. The benzobis(thiadiazole) derivative according to claim 2, wherein the R group comprises a structure represented by any one of the formulae (B-1) to (B-6):

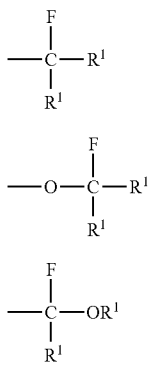

(B-1)

(B-2)

(B-3)

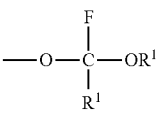

(B-4)

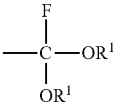

(B-5)

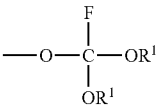

(B-6)

wherein
R$^1$ represents hydrogen atom, fluorine atom, linear or branched alkyl group, or linear or branched alkyl group substituted with at least one fluorine atom, with the proviso that two R$^1$ groups may be the same as, or different from each other.

4. The benzobis(thiadiazole) derivative according to claim 3, wherein the R group comprises a structure represented by any one of the formulae (C-1) to (C-4):

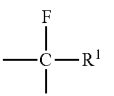

(C-1)

(C-2)

(C-3)

(C-4)

wherein
R$^1$ represents hydrogen atom, fluorine atom, linear or branched alkyl group, or linear or branched alkyl group substituted with at least one fluorine atom.

5. The benzobis(thiadiazole) derivative according to claim 2, wherein the R group comprises a structure represented by any one of the formulae (D-1) to (D-6):

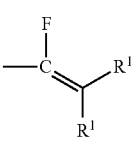

(D-1)

-continued

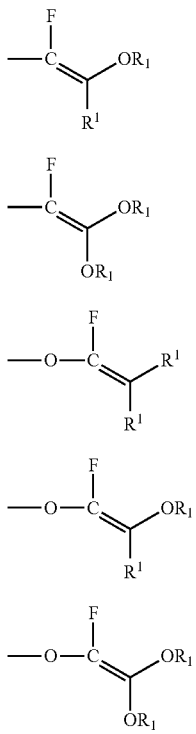

wherein
R¹ represents hydrogen atom, fluorine atom, linear or branched alkyl group, or linear or branched alkyl group substituted with at least one fluorine atom, with the proviso that two R¹ groups may be the same as, or different from each other.

6. The benzobis(thiadiazole) derivative according to claim 2, wherein the R¹ group is hydrogen atom, fluorine atom, linear or branched alkyl group containing 1 to 30 carbon atoms, or linear or branched alkyl group containing 1 to 30 carbon atoms and substituted with at least one fluorine atom.

7. The benzobis(thiadiazole) derivative according to claim 6, wherein the R¹ group is hydrogen atom, fluorine atom, linear or branched alkyl group containing 1 to 10 carbon atoms, or linear or branched alkyl group containing 1 to 10 carbon atoms and substituted with at least one fluorine atom.

8. The benzobis(thiadiazole) derivative according to claim 2, wherein the R¹ group is hydrogen atom, fluorine atom, alkyl group, 1-fluoroalkyl group, 1,1-difluoroalkyl group, 1,1,2-trifluoroalkyl group, 1,1,2,2-tetrafluoroalkyl group, 1,1,2,2,3,3-hexafluoroalkyl group, 1,1,2,2,3,3,4,4-octafluoroalkyl group, 1,1,2,2,3,3,4,4,5,5-decafluoroalkyl group, 1,1,2,2,3,3,4,4,5,5,6,6-dodecafluoroalkyl group, 1,1,2,2,3,3,4,4,5,5,6,6,7,7-tetradecafluoroalkyl group, 1,1,2,2,3,3,4,4,5,5,6,6,7,7,8,8-hexadecafluoroalkyl group, 1,1,2,2,3,3,4,4,5,5,6,6,7,7,8,8,9,9-octadecafluoroalkyl group, or perfluoroalkyl group.

9. The benzobis(thiadiazole) derivative according to claim 1, wherein the m is an integer of from 1 to 3.

10. The benzobis(thiadiazole) derivative according claim 1, wherein the benzobis(thiadiazole) derivative is soluble in an organic solvent.

11. An organic semiconductor ink comprising the benzobis(thiadiazole) derivative according to claim 1.

12. An organic semiconductor ink comprising two or more of organic semiconductors, wherein one or more of the organic semiconductors is the benzobis(thiadiazole) derivative according to claim 1.

13. An organic electronic device comprising an organic layer, which comprises the benzobis(thiadiazole) derivative according to claim 1.

14. An organic thin film transistor, comprising a gate electrode, a gate insulating layer, an organic semiconductor layer, a source electrode, and a drain electrode on a substrate, wherein
the organic semiconductor layer comprises the benzobis(thiadiazole) derivative according to claim 1.

15. An organic electroluminescence device, comprising an anode, a luminescent layer, a hole transport layer and/or an electron transport layer, and a cathode on a substrate, wherein
the hole transport layer and/or the electron transport layer comprise the benzobis(thiadiazole) derivative according to claim 1.

16. A display device, in which an organic electroluminescence device is driven/lighted using an organic thin film transistor, wherein
the organic thin film transistor is the organic thin film transistor according to claim 14.

17. An active-matrix display device, wherein
pixels are arranged in a matrix form, the pixel comprising the organic thin film transistor according to claim 14 and an organic electroluminescence device.

18. A display device in which an organic electroluminescence device is driven/lighted using an organic thin film transistor, wherein
the organic thin film transistor is an organic thin film transistor comprising a gate electrode, a gate insulating layer, an organic semiconductor layer, a source electrode, and a drain electrode, wherein the organic semiconductor layer comprises the benzobis(thiadiazole) derivative according to claim 1, and
the organic electroluminescence device is an organic electroluminescence device comprising an anode, a luminescent layer, a hole transport layer and/or an electron transport layer, and a cathode, wherein the hole transport layer and/or the electron transport layer comprise the benzobis(thiadiazole) derivative according to claim 1.

19. A display device, in which an organic electroluminescence device is driven/lighted using an organic thin film transistor, wherein
the organic electroluminescence device is the organic electroluminescence device according to claim 15.

20. An organic thin film photovoltaic cell, comprising an anode, a charge separation layer comprising a hole transport material and an electron transport material, and a cathode on a substrate, wherein
the charge separation layer comprises the benzobis(thiadiazole) derivative according to claim 1.

21. An organic thin film photovoltaic cell, comprising an anode, a charge separation layer comprising a hole transport material and an electron transport material, a hole transport layer and/or an electron transport layer, and a cathode on a substrate, wherein
the hole transport layer and/or the electron transport layer comprise the benzobis(thiadiazole) derivative according to claim 1.

22. The organic electronic device according to claim 13, further comprising a flexible substrate.

23. The An active-matrix display device according to claim 17, wherein:
pixels are arranged in a matrix form, the pixel comprising an organic thin film transistor and an organic electroluminescence device;
the organic thin film transistor is an organic thin film transistor comprising a gate electrode, a gate insulating layer, an organic semiconductor layer, a source electrode, and a drain electrode, wherein the organic semiconductor layer comprises the benzobis(thiadiazole) derivative according to claim 1; and the organic electroluminescence device is an organic electroluminescence device comprising an anode, a luminescent layer, a hole transport layer and/or an electron transport layer, and a cathode, wherein the hole transport layer and/or the electron transport layer comprise the benzobis(thiadiazole) derivative according to claim 1.

* * * * *